US011467158B2

(12) United States Patent
Bharti

(10) Patent No.: US 11,467,158 B2
(45) Date of Patent: Oct. 11, 2022

(54) BRCA1 MUTATIONS AS PREDICTIVE MARKERS FOR TOPOISOMERASE INHIBITIONS

(71) Applicant: BOSTON MEDICAL CENTER CORPORATION, Boston, MA (US)

(72) Inventor: Ajit Bharti, West Roxbury, MA (US)

(73) Assignee: BOSTON MEDICAL CENTER CORPORATION, Boston, MA (US)

(*) Notice: Subject to any disclaimer, the term of this patent is extended or adjusted under 35 U.S.C. 154(b) by 0 days.

(21) Appl. No.: 14/439,543

(22) PCT Filed: Mar. 14, 2013

(86) PCT No.: PCT/US2013/031337
§ 371 (c)(1),
(2) Date: Apr. 29, 2015

(87) PCT Pub. No.: WO2014/070233
PCT Pub. Date: May 8, 2014

(65) Prior Publication Data
US 2015/0285801 A1 Oct. 8, 2015

Related U.S. Application Data

(60) Provisional application No. 61/719,543, filed on Oct. 29, 2012.

(51) Int. Cl.
*G01N 33/574* (2006.01)
*C12Q 1/6886* (2018.01)

(52) U.S. Cl.
CPC ......... *G01N 33/574* (2013.01); *C12Q 1/6886* (2013.01); *G01N 33/57484* (2013.01); *C12Q 2600/106* (2013.01); *C12Q 2600/156* (2013.01); *G01N 2333/90* (2013.01); *G01N 2333/9015* (2013.01)

(58) Field of Classification Search
CPC .................................................. G01N 33/574
USPC ......................................................... 435/7.23
See application file for complete search history.

(56) References Cited

U.S. PATENT DOCUMENTS

| 4,031,098 | A | 6/1977 | Sugasawa |
| 4,473,692 | A | 9/1984 | Miyasaka et al. |
| 4,545,880 | A | 10/1985 | Miyasaka et al. |
| 4,604,463 | A | 8/1986 | Miyasaka et al. |
| 5,049,668 | A | 9/1991 | Wall et al. |
| 5,106,742 | A | 4/1992 | Wall et al. |
| 5,364,858 | A | 11/1994 | Wall et al. |
| 5,420,016 | A | 5/1995 | Boguslaski et al. |
| 5,468,754 | A | 11/1995 | Hausheer et al. |
| 5,604,233 | A | 2/1997 | Hausheer et al. |
| 5,674,873 | A | 10/1997 | Hausheer et al. |
| 5,731,316 | A | 3/1998 | Cao et al. |
| 5,807,874 | A | 9/1998 | Lavoie et al. |
| 6,660,861 | B1 | 12/2003 | Puri et al. |
| 6,790,636 | B1 | 9/2004 | Star et al. |
| 7,270,808 | B2 | 9/2007 | Cheng et al. |
| 8,993,309 | B2 | 3/2015 | Bharti |
| 9,644,036 | B2 | 5/2017 | Bharti |
| 2008/0280935 | A1 | 11/2008 | Naidu |
| 2009/0191547 | A1* | 7/2009 | Miron ................... C12Q 1/6827 435/6.11 |

(Continued)

FOREIGN PATENT DOCUMENTS

| EP | 0074256 B1 | 11/1986 |
| JP | 2005-029573 | 2/2005 |
| JP | 2006-038614 | 2/2006 |

(Continued)

OTHER PUBLICATIONS

Ruffner, H. et al., Proc. National Acad. Sci., 98(9): 5134-5135, 2001.*
Fedier, A., et al., International Journal of Oncology, 22: 1169-1173, 2003.*
Pommier, Y., Biochimie, 80: 255-270, 1998.*
Pommier, Y., Nature Review, 6: 789-802, 2006.*
Hollestelle, A., et al., Breast Cancer Res. Treat. 121: 53-64, 2010.*
Friedman, Nature Genetics, 8: 399-404, 1994.*
Dong, Y., et al. Methods Mol. Med, 108: 149-157, 2005; Abstract only.*
Grzybowska et al (Human Mutation, 2000, 16: 482-490).*
Zhang et al (Breast Cancer Res Treat, 2012, 134: 889-894).*

(Continued)

*Primary Examiner* — Sean E Aeder
(74) *Attorney, Agent, or Firm* — Nixon Peabody LLP; Ronald I. Eisenstein; Susanna C Benn

(57) ABSTRACT

The present invention generally relates to the fields of cancer therapy and cancer prevention. More particularly, the present invention generally relates to a diagnostic marker for predicting the efficacy of topoisomerase I (topo I) inhibitors in the treatment of cancers. More specifically, the present invention relates to methods, machines, computer systems, computable readable media and kits which can be used to identify and determine the effectiveness of topoisomerase I (topo I) inhibitors in the treatment of cancers, and in some embodiments, the level of sensitivity or resistance of a tumor cell to a topoisomerase I inhibitor, such as camptothecin (CPT), or CPT analogues such as topotecan and irinotecan and derivatives thereof. More specifically, the present invention related to methods, machines, computer systems, computable readable media and kits which can be used to determine a mutation in the BRCA1 gene, e.g., in the RING domain and/or BRCT domain of BRCA1, and where the presence of such mutation which interferes with the interaction of BRCA1 with phosphorylated Topo I indicates that the subject who has the mutation is likely to be responsive to a topo I inhibitor, Other aspect of the present invention relate to assays and methods to screening candidate compounds to interrupt or interfere with the interaction of BRCA1 with phospho-serine10 topoisomerase I, and uses thereof.

5 Claims, 15 Drawing Sheets
Specification includes a Sequence Listing.

(56) References Cited

U.S. PATENT DOCUMENTS

2011/0027277 A1  2/2011  Bharti

FOREIGN PATENT DOCUMENTS

| JP | 2007-223902 | 9/2007 |
|---|---|---|
| JP | 2008-045976 | 2/2008 |
| WO | 2006/081331 A2 | 8/2006 |
| WO | 2008/021549 A2 | 2/2008 |

OTHER PUBLICATIONS

Shih et al (Clin Cancer Res, 2000, 6: 4259-4264).*
Malander et al. (European Journal of Cancer 2004, 40: 422-428).*
Santarosa et al (Int J Cancer, 1998, 78: 581-586).*
Press et al (Implications of BRCA-loss of Phenotype in Epithelial Ovarian Carcinoma, 2006, University of British Columbia).*
Foretova et al (Human Mutation, Mutation in Brief#697, 2004, 1-8).*
Jalkh et al (Hereditary Cancer in Clinical Practice, 2012, 10:7).*
Brzovic et al., "Binding and recognition in the assembly of an active BRCA1/BARD1 ubiquitin-ligase complex" PNAS 100(10):5646-5651 (2003).
Clark et al., "Structure-function of the tumor suppressor BRCA1" Computational and Structural Biotechnology Journal 1(1):1-16 (2012).
Di Masi et al., "Cancer predisposing mutations in BRCT domains" IUBMB Life 63(7):503-512 (2011).
Ruffner et al., "Cancer-predisposing mutations within the RING domain of BRCAI: loss of ubiquitin protein ligase activity and protection from radiation hypersensitivity" 98(9):5134-5139 (2001).
Zander et al., "Sensitivity and acquired resistance of BRCA1: p53-deficient mouse mammary tumors to the topoisomerase I inhibitor topotecan" Cancer Research 70(4):1700-1710 (2010).
Atipairin et al., "In Vitro Enhanced Sensitivity to Cisplatin in D67Y BRCA1 RING Domain Protein", Breast Cancer Basic and Clinical Research, 5:201-208 (2011).
Atipairin et al., "The RING heterodimer BRCA1-BARD1 is a ubiquitin ligase inactivated by the platinum-based anticancer drugs", Breast Cancer Res. Treat., 126(1): Abstract (2011).
Bharti et al., "Identification of a Nucleolin Binding Site in Human Topoisomerase I" The Journal of Biological Chemistry, 271(4):1993-1997(1996).
Brzovic et al., "BRCA1 Ring Domain Cancer-predisposing Mutations", J. Biol. Chem., 276(44):41399-41406 (2001).
Brzovic et al., "Structure of a BRCA1-BARD1 heterodimeric RING-RING complex." Nat. Struct. Biol., 8(10):833-837 (2001).
Cardellini et al., "Human Topoisomerase I is Phosphorylated in vitro on its Amino Terminal Domain by Protein Kinase NII" Biol. Chem. Hoppe-Seler, 375:255-259 (1994).
Chikamori et al., "Phosphrylation of Serine 1106 in the Catalytic Domain of Topoisomerase II alpha Regulates Enzymatic Activity and Drug Sensitivity", J. Biol. Chem., 278(15):12696-12702 (2003).
Coderoni et al., "Phosphorylation Sites for Type N II Protein Kinase in DNA-Topoisomerase I From Calf Thymus." Int. J. Biochem., 22(7):737-746 (1990).
Coquelle et al., "Impact of BRCA1 Brct Domain Missense Substiutions on Phosphopeptide Recognition", Biochem., 50:4579-4589 (2011).
Corey et al. "A Total Synthesis of Natural 20(S)-Camptothecin" J. Org. Chem., 40(14):2140-41 (1975).
Desai et al.,"Ubiquitin-dependent Destruction of Topoisomerase I Is Stimulated by the Antitumor Drug Camptothecin", J. Biol. Chem., 272(39):24159-24164 (1997).
Figge et al.,"Missense Mutations in the BRCT Domain of BRCA-1 from High-Risk Women Frequently Perturb Strongly Hydrophobic Amino Acids Conserved among Mammals", Cancer Epidmiol Biomarkers Prev, 13(6):1037-1041 (2004).
Gallo et al.,"Studies on the Antitumor Activity, Mechanism of Action, and Cell Cycle Effects of Camptothecin" J Nat Cancer Inst, 46(4):789-795 (1971).
Giovanella et al., "Complete Growth Inhibition of Human Cancer Xenografts in Nude Mice by Treatment with (20-S)-Camptothecin" Cancer Res, 51:3052-3055 (1991).
Gloffke, "Detecting Protein Phosphorylation", The Scientist, pp. 52 (2002).
Kametani et al. "Studies on the Syntheses of Heterocyclic Compounds. Part 878. Synthesis of (±)-Camptothecin and (±)-10-Methoxycamptothecin via Enamine Annulation", J. Chem. Soc., Perkin Trans. 1, 1563-1568 (1981).
Kuriyama et al., "Monoclonal Anti-Dipeptide Antibodies Cross-React with Detyrosinated and Glutamylated Forms of Tubulins", Cell Motility and the Cytoskeleton, 30:171-182 (1995).
Masters, "HeLa cells 50 years on: the good, the bad and the ugly", Nature Reviews: Cancer, 2:315-318 (2002).
Pommier,"Topoisomerase I inhibitors: camptothecins and beyond", Nature Reviews: Cancer, 6:789-802 (2006).
Rasheed et al.,"Mechanisms of resistance to topoisomerase I-targeting drugs", Oncogene, 22:7296-7304 (2003).
Sanchez-Perez, "DNA repair inhibitors in cancer treatment", Clin Transl Oncol. 8(9):642-646 (2006).
Shanghai Institute of Materia Medica et al. "The Total Synthesis of dl-Camptothecin" Scientia Sinica, 21(1);87-98 (1978).
Sorlie et al."Gene expression patterns of breast carcinomas distinguish tumor subclasses with clinical implications" NAS. 98(19);10869-10874 (2001).
St-Amant et al., "Altered phosphorylation of topoisomerase I following overexpression in an ovarian cancer cell line", Biochem. Cell Biol. 84(1):55-66 (2006).
Wani et al. "Plant Antitumor Agents; Alkaloids; Synthesis of a Pentacyclic Camptothecin Precursor" Chemical Communications, 404-404 (1970).
Wani et al.,"Plant Antitumor Agents. IX. The Total Synthesis of dl-Camptothecin" J. Am. Chem. Soc., 94(10);3631-32 (1972).
Wani et al.,"Plant Antitumor Agents. 18. Synthesis and Biological Activity of Camptothecin Analogues" J. Med. Chem., 23(5):554-560 (1980).
Yu et al.,"Phosphorylation of DNA Topoisomerase I by the c-Abl Tyrosine Kinase Confers Camptothecin Sensitivity." J Biol Chem. 279(50):51851-51861 (2004).
Zhang et al. "Topotecan Inhibits Human Immunodeficiency Virus Type 1 Infection through a Topoisomerase-Independent Mechanism in a Cell Line with Altered Topoisomearse I", Antimicrobial Agents and Chemotherapy, 41(5):977-981 (1997).
Page 4 of Examination Report dated May 19, 2014, in connection with European Patent Application No. 09726814.8.
"Breast Cancer Information Core BRCA1 mutation database", http://research.nhgri.nih.gov/bic/. (2013).
Berglund et al., "The epitope space of the human proteome." Protein Sci. 17(4): 606-13 (2008).
Corada et al., "Monoclonal antibodies directed to different regions of vascular endothelial cadherin extracellular domain affect adhesion and clustering of the protein and modulate endothelial permeability." Blood 97(6): 1679-84 (2001).
Kulkarni-Kale et al., "CEP: a conformational epitope prediction server." Nucleic acids research 33.suppl_2 (2005):W168-W171.
Padlan "X-ray crystallography of antibodies." Adv Protein Chem 49:57-133 (1996).
Tzartos "Epitope mapping by antibody competition. Methodology and Evaluation of the validity of the technique.", Methods Mol Biol. 66: 55-66 (1996).

* cited by examiner

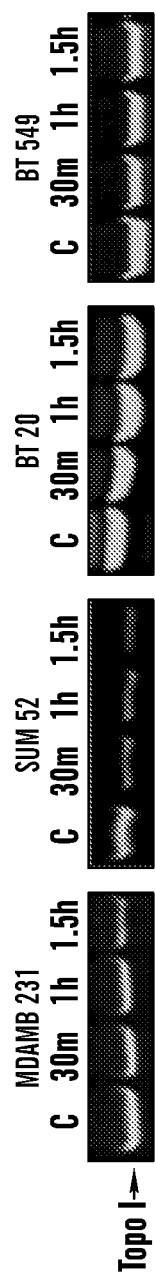
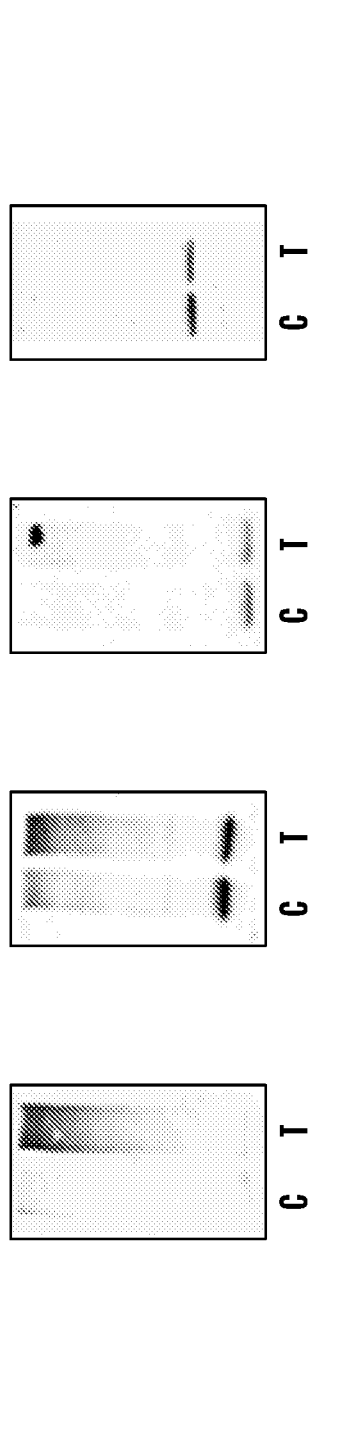
FIG. 3A
FIG. 3B

BRCA1 MUTATIONS AS PREDICTIVE MARKERS FOR TOPOISOMERASE INHIBITIONS

CROSS REFERENCE TO RELATED APPLICATIONS

This application is a 371 National Phase Entry of International Patent Application No. PCT/US2013/031337 filed on Mar. 14, 2013 which claims benefit under 35 U.S.C. § 119(e) of U.S. Provisional Patent Application Ser. No. 61/719,543 filed on Oct. 29, 2012, the contents of which are incorporated herein by reference in their entirety.

SEQUENCE LISTING

The sequence listing of the present application has been submitted electronically via EFS-Web as an ASCII formatted sequence listing with a file name "701586-075861-PCT_SL", creation date of Apr. 28, 2015 and a size of 37,956 bytes. The sequence listing submitted via EFS-Web is part of the specification and is herein incorporated by reference in its entirety.

FIELD OF THE INVENTION

The present invention relates generally to the fields of cancer therapy and cancer prevention. More particularly, the present invention generally relates to a diagnostic marker for predicting the efficacy of topoisomerase I (topo I) inhibitors in the treatment of cancers, and the level of sensitivity or resistance of a biological sample to topoisomerase I inhibitors.

BACKGROUND OF THE INVENTION

One of the main problems associated with cancer chemotherapy is that individual subjects with the same histology do not respond identically to a given agent or a given therapeutic protocol. The response range may vary in large proportions, even in chemosensitive tumors such as breast cancer. A number of determinants of drug sensitivity are well known, such as drug dose, drug combinations and schedule of administration, subject age and status, tumor localization etc., but the intrinsic sensitivity of a given tumor is a major factor in which remains difficult to evaluate.

One strategy to improve the effectiveness of treatment has been to individualize drug treatment as a function of the sensitivity of tumor cells. Methods to predict how effective a drug may be in a subject are typically based on in vitro or ex vivo testing of the tumor cells (taken during a biopsy) to a battery of drugs and chemotherapy agents. Such strategies have several limitations; they are often poor predictors of chemosensitivity in vivo, they are time-consuming, and both manually and cost expensive. The identification of novel cancer subtypes promises to provide more specific, more effective and less toxic therapies. This tumor subset is refractory to commonly used chemotherapeutic agents and therefore is associated with a poor prognosis (Sorlie, et al., 2001, Proc Natl Acad Sci USA 98:10869). To date little progress has been made in identifying specific molecular pathways associated with these refractory cancers that may be effectively targeted for therapeutic purposes.

Human topoisomerase I (topoI) is an essential and ubiquitous enzyme that is involved in various DNA transactions. The identification of topo I as the target of a new class of anti-neoplastic drug (camptothecin, also referred herein as "CPT") has led to the rapid development of topo I structure-function in the context of cancer therapy. Two CPT analogues, topotecan and irinotecan, are currently used in clinics for small cell lung cancer (SCLC), colon and ovarian cancer and in several refractory cancers, including breast and cervical. However, like most cancer drugs, not all patients respond, in this case only about 30% of patients respond to topo I inhibitors. The topo I protein level is high in most solid tumors, and thus topo I levels can not be used as a predictive marker. Additionally, although topo I is the specific target of CPT, the expression profile of topo I does not provide prognostic index. Based on the preclinical studies, it is likely that clinical resistance to these drugs might be the result of (1) inadequate accumulation of the drug in the tumor, or (2) post-translational modification of topoI. It has been demonstrated that topo I is ubiquitinated and degraded in cells in the response to CPT by ubiquitin proteosomal pathway (UPP). Importantly, the rate of UPP mediated degradation varies in different cancer cells and is correlated to the CPT sensitivity. However the mechanism of ubiquitination dependent proteosomal degradation of topo I in the response to CPT is not understood.

There is a significant need in the art for a satisfactory treatment of tumor subsets refectory or non-responsive to commonly used chemotherapeutic agents, (specifically in epithelial cell cancers such as breast, lung, ovarian, brain, colon and prostate cancers), which overcomes the non-responsiveness exhibited by subjects. Such a treatment could have a dramatic impact on the health of individuals, especially older individuals, among whom cancer is especially common, and females whom have a high incidence of breast cancer.

SUMMARY OF THE INVENTION

The present invention generally relates to diagnostic markers for predicting the efficacy of topoisomerase I (topo I) inhibitors in the treatment of cancers. In particular, the inventors have previously demonstrated that topo I is phosphorylated at S10 by DNA-PK and results in its ubiquitination by BRAC1/BARD1 heterodimer and its subsequent degradation (as disclosed in US Application 2011/0027277, which is incorporated herein in its entirety by reference). Importantly, the inventors have previously discovered that the presence of phosphorylation of topoI, in particular the phosphorylation of topo I on serine 10 (S10) indicates rapid topo I degradation and resistance to topo I inhibitors such as camptothecin (CPT), or CPT analogues such as topotecan and irinotecan and derivatives thereof.

Herein the inventors have demonstrated that a subject with one or more mutations in the BRCA1 protein, e.g., a mutation in any one or more of (i) the BRCA1 RING domain, (ii) the BRCT domain of BRCA1, or (iii) the E3 ligase domain and/or RING domain of BRCA1 which impairs the E3 ligase activity, will identify the subject to be responsive (e.g., sensitive) to topo I inhibitors such as camptothecin (CPT), or CPT analogues such as topotecan and irinotecan and derivatives thereof. Accordingly, the inventors have discovered that mutations in the BRCT domain of BRCA1 which disrupt or impair the interaction of BRCT with the phospho-topo I protein will reduce topo I degradation and thus increase sensitivity of the subject to topo I inhibitors. For example, without wishing to be bound by theory, the inventors have discovered that a mutation in the BRCA1 gene, e.g., in the RING domain and/or BRCT domain of BRAC1) which decreases the ability of BRCA1 to ubiquitinate phosphor-ser10-Topo I prevents its degradation, and thus the subject is sensitive or responsive to a topo I inhibitor.

Accordingly, one aspect of the present invention relates to detection of mutations in BRCA1 in a biological sample from a subject with cancer, as a prognostic determinant for drug efficacy with topo I inhibitors such as CPT and its analogues.

One aspect of the present invention relates to methods and compositions to determine if a topo isomerase I (topo I) inhibitor is effective in a subject with cancer. One aspect of the present invention relates to a method to determine the presence of one or more mutations in BRCA1 gene, e.g., in the RING domain, and/or BRCT domain and/or a mutation which disrupts E3 ligase activity of BRCA1, wherein the presence of such a mutation indicates that the subject having such cancer will likely be responsive (or sensitive) to a topo I inhibitor as compared to a subject with a cancer who does not have such mutations in the BRCA1 gene.

In some embodiments, a mutation in the BRCA1 RING domain between amino acids 1-109 of SEQ ID NO: 6 which interrupts (e.g., decreases the binding affinity) of the binding of RING domain of BRCA1 with its binding partner BARD1 and/or any BRCA1 E2 conjugating enzyme, including but not limited to UbCH5 and UbCH7, and/or decreases the E3 ligase activity of BRCA1, indicates that the subject carrying the mutation will be responsive to a topo I inhibitor, e.g., CPT or its analogues.

In another embodiment, a mutation in the BRCA1 BRCT domain between or inclusive of amino acids 1650-1863 of SEQ ID NO: 6 which interrupts the binding of BRCA1 (via the BRCT domain) with the topo I protein indicates that the subject carrying the mutation will be responsive to a topo I inhibitor, e.g., CPT or its analogues. In some embodiments, a mutation between, or inclusive of amino acids 1-109 or 1650-1863 which interrupts the BRCA1 binding with the topo I protein can be assessed by one of ordinary skill in the art using the fluorescence polarization assay as disclosed herein in the Examples.

In some embodiments, a mutation is any change of nucleic acid in BRCA1 gene (e.g., SEQ ID NO: 5) which changes the amino acid cysteine at position 39 (e.g., cystine39) of the BRAC1 protein (SEQ ID NO: 6), or changes the amino acid of the cysteine at position 61 (cysteine 61) in the RING domain of BRCA1 protein. In some embodiments, any mutation in the RING domain of the BRCA1 gene, which decreases the RING E3 ligase activity and/or decreases the RING binding affinity for BARD1, and/or decreases the binding affinity of BRCA1 for any BRCA1 E2 conjugating enzyme (e.g., including but not limited to UbCH5 and UbCH7), includes but are limited to the following mutations; M18, C24R, I26A, T37, C39A, C39Y, C44F/G, C44F, I31M, L51A, C61G, C64A, C64Y, T73R, C44F, C47F/G will identify a subject will likely be responsive to a topo I inhibitor and thus be amenable to treatment with a topo I inhibitor as disclosed herein. Other mutations in the RING domain of BRCA1 are encompassed herein, which include those disclosed in Brovic et al., "BRCA1 RING domain cancer-disposing mutations", J. Biol. Chem., 2001; 275(44); 41399-41406, and Serena et al., Comput. Struct. Biotech., J, June 2012, and Ruffner et al., "Cancer-predisposing mutations within the RING domain of BRCA1: Loss of ubiquitin protein ligase activity and protection from radiation hypersensitivity" PNAS, 2001, 98(a); 5134-5139, which are incorporated herein in their entireties by reference.

In some embodiments, the mutation is a change of nucleic acid which results in a change of the amino acid arginine at position 1699 (e.g., arginine 1699) in the BRCT domain of the BRCA1 protein, for example a nucleic acid change which results in arginine 1699 changing to tryptophan (R1699W). In some embodiments, the mutation is a change of nucleic acid which results in a change of the amino acid glutamic acid at position 1836 (e.g., glutamic acid 1836) in the BRCT domain, for example a change of glutamic acid 1836 to lysine (G1656D). In some embodiments, a mutation in the BRCT domain of BRCA1 which interrupt or decreases the binding affinity of BRCA1 to the Topo I protein can include, for example, but not limited to, G1656D, T1700A, R1699Q, R1699W, M1775R, M1775K, R1835P or E1836K.

Other mutations in the BRCT domain of BRCA1 are encompassed herein, which include BRCT missense substitutions as disclosed in Coquelle et al., "Impact of BRCA1 BRCT domain missense mutations substitutions on phosphopeptide recognition", Biochem, 2011; 50; 4579-4589, which is incorporated herein in its entirety by reference.

Another embodiment of this aspect and all other aspects disclosed herein, relate to the detection of a lack of a mutation in the BRCA1 RING domain (e.g., lack of a mutation in the RING domain which decreases the E3 ligase activity of BRCA1 and/or interrupts the binding of BRCA1 with its binding partner BARD1 or an E2 conjugating enzyme (e.g., including but not limited to UbCH5 and UbCH7), and/or lack of a mutation in the BRCT domain (e.g., lack of a mutation in the BRCT domain which decreases the binding affinity of BRCT domain with phosphor-ser10-topo I) and/or E3 ligase domain of BRCA1 gene in a subjects, and indicates that a subject with such a cancer is likely to be unresponsive (non-responsive) to a topo I inhibitor.

Another aspect of the present invention relates to methods, assays and kits to identify mutations in the RING and/or BRCT domain of BRCA1 which interrupt the binding of BRCA1 protein to the phospho-topo I protein, e.g., phospho-ser10-Topo I protein. In some embodiments, a mutation in the BRCA1 RING domain is a mutation which decreases the E3 ligase activity of BRCA1 and/or interrupts or decreases the binding affinity of RING domain of BRCA1 with its binding partner BARD1 or decreases its binding affinity to an E2 conjugating enzyme (e.g., including but limited to UbCH5 and UbCH7). In some embodiments, a mutation in the BRCT domain is a mutation in the BRCT domain which decreases the binding affinity of BRCT domain of BRCT1 with phosphor-ser10-topo I. As disclosed herein, one such assay is a fluorescent polarization (FP) assay, comprising a BRCT domain comprising a mutation of interest, and a topo I phosphopeptide, e.g., such as SEQ ID NO: 4. In some embodiments, the BRCT domain of BRCA1 (e.g., amino acids 1650-1863 of SEQ ID NO: 6 or a functional fragment thereof) is conjugated to a GST or other molecule.

In some embodiments, the binding affinity or interaction of a BRCT domain that comprises a mutation with the topo I phosphopeptide is assessed and compared with the binding affinity or interaction of a wild type BRCT domain with the topo I phosphopeptide to determine if the mutation in the BRCT domain decreases (e.g., interferes) the binding affinity of the BRCT domain with the topo I phosphopeptide. Detection of a decrease of binding affinity will indicate that the mutation interferes with the BRCT-phospho-S10 topo I polypeptide interaction and that a subject with such mutation will be responsive to treatment with topo I inhibitors, e.g., CPT or analogues or derivatives thereof.

In another embodiment, a similar fluorescent polarization (FP) assay can be performed, comprising the RING domain of BRCA1 comprising a mutation of interest, and a topo I phosphopeptide, e.g., such as SEQ ID NO: 4 or SEQ ID NO:1. In some embodiments, the RING domain of BRCA1 (e.g., amino acids 1-109 of SEQ ID NO: 6 or a functional fragment thereof) is conjugated to a GST or other molecule.

In some embodiments, the binding affinity or interaction of a RING domain comprising a mutation with the topo I phosphopeptide is assessed and compared with the binding affinity or interaction of a wild type RING domain with the topo I phosphopeptide to determine if the mutation in the RING domain decreases (e.g., interferes) the binding affinity of the RING domain with the topo I phosphopeptide (or decreases affinity for BARD1 or an E2 conjugating enzyme (e.g., including but limited to UbCH5 and UbCH7)), and/or decreases ubiquitination of the topo I phosphopeptide. Detection of a decrease of binding affinity, or decrease in ubiquitination of the phosphopeptide will indicate that the mutation interferes with the BRCA1-phospho-S10 topo I polypeptide interaction, or decreases E3 ligase function of BRCA1 and thus ubiquitination of phosphor-S10-Topo I protein and that a subject with such mutation will be responsive to treatment with topo I inhibitors, e.g., CPT or analogues or derivatives thereof.

Another aspect of the present invention relates to methods, assays and kits for high-throughput screening (HTS) of candidate molecules to identify compounds which interfere with the BRCA1-phospho-ser10 topo I polypeptide interaction. In some embodiments, an assay comprises a topo I polypeptide or a functional fragment thereof, which is phosphorylated on serine 10 (S10) by a kinase, e.g., DNA-PK kinase, then incubated with a ubiquitin mixture comprising a BRCT domain of BRCA1, or a functional fragment thereof, and then is pre-incubated with at least one test compound, where a decrease in fluorescence as compared to a negative control or absence of a test compound indicates that the test compound decreases the interaction of BRCT domain of BRCA1 with the phosphor-S10-topo I protein. Such a compound is thus useful to be used in conjunction or in combination with a topo I inhibitor, e.g., CPT or analogues thereof to increase the efficacy of the topo I inhibitor in the treatment of cancer.

Another aspect of the present invention relates to a method to treat cancer in a subject, the method comprising assessing a biological sample from the subject with cancer for the presence of a mutation in the BRCA1 RING domain (e.g., a mutation in the RING domain which decreases the E3 ligase activity of BRCA1 and/or interrupts or decreases the binding affinity of RING domain of BRCA1 with its binding partner BARD1 or an E2 conjugating enzyme (e.g., including but limited to UbCH5 and UbCH7)) and/or a mutation in the BRCT domain (e.g., a mutation in the BRCT domain which decreases the binding affinity of BRCT domain of BRAC1 with phosphor-ser10-topo I) or other mutation which affects the ubiquitination E3 ligase function of the BRCA1 gene; and if a mutation is detected which interrupts the binding of BRCA1 to the phospho-S10-topo I polypeptide, and/or decreases the ubiquitination of phosphor-ser10-topo I protein, the cancer is identified as being responsive to a topoisomerase I inhibitor. In one embodiment, the biological sample taken from a subject can be tested using the methods, kits, machines and computer systems and computer readable media as described herein.

In some embodiments, a cancer is identified as being responsive to a topoisomerase I inhibitor where the subject having the cancer has a mutation in the BRCA1 RING domain (e.g., a mutation in the RING domain which decreases the E3 ligase activity of BRCA1 by at least 10% as compared to wild type BRCA1 gene, and/or decreases the binding affinity of RING domain of BRCA1 with its binding partner BARD1 or an E2 conjugating enzyme (e.g., including but limited to UbCH5 and UbCH7) by at least 10% as compared to the wild type BRCA1 gene) and/or a mutation in the BRCT domain (e.g., a mutation in the BRCT domain which decreases the binding affinity of BRCT domain of BRCA1 with phosphor-ser10-topo I by at least 10% as compared to a wild type BRCA1 protein).

In another embodiment, the mutation in the RING domain causes a decreases in the E3 ligase activity of BRCA1 and/or a decrease in the binding affinity of the RING domain of BRCA1 with its binding partner BARD1 or an E2 conjugating enzyme (e.g., including but limited to UbCH5 and UbCH7) by a statistically significant amount, e.g., at least one standard deviation, more preferably by at least two standard deviations as compared to the wildtype BRCA1 gene.

In another embodiment, the mutation in the BRCT domain causes a decrease in the binding affinity of BRCT domain with phospho-ser10 topoI by a statistically significant amount, e.g., at least one standard deviation, more preferably by at least two standard deviations as compared to the binding affinity of BRCT domain with phospho-ser10 topo I by the wildtype BRCA1 gene.

In another embodiment, the absence or presence of a mutation in the human BRCA1 gene can be detected by analyzing gene product (e.g. RNA and/or protein). In one embodiment, a probe can specifically bind to a variant of BRCA1 gene product or protein. In some embodiments, a probe can bind to different variants of the BRCA1 protein. Alternatively, probes can also be used for screening for changes in the amino acid sequence of the BRCA1 protein of SEQ ID NO: 6. For example, but not limited to, one can screen for any changes in the amino acid sequence of BRCA1 (SEQ ID NO:6).

In some embodiments, a subject identified as being likely to be responsive to a topoisomerase I inhibitor by the methods as disclosed herein can be treated with a therapeutically effective amount of a topo I inhibitor, such as, but not limited to CPT, or analogues thereof such as topotecan and irinotecan, either alone or in combination with other therapeutic and/or anti-cancer drugs.

In some embodiments, a topo I inhibitor is a chemotherapy agent, for example but not limited to CPT, or analogues thereof such as topotecan and irinotecan and derivatives as these terms are defined herein. Another aspect of the present invention provides to methods for treating and/or preventing a subject affected with or at risk of developing cancer, the method comprising determining the presence of at least one mutation in the BRCA1 gene, and in particular embodiments, the method comprises determining the presence of a mutation in one or more of the RING domain, BRCT domain or E3 ligase domain of the BRCA1 gene. In other embodiments, the methods, kits, machines, computer systems and computer readable media are used to determine the presence of at least one mutation in the BRCA1 gene, e.g., a mutation in one or more of the RING domain, BRCT domain or E3 ligase domain of the BRCA1 gene in a biological sample.

In one embodiment, any means known to a skilled artisan to determine the presence of a mutation in the RING domain and/or BRCT domain of BRCA1 can be used. Accordingly, the present invention encompasses use of any in vivo detection method, any ex vivo detection method or any in vitro detection method to determine the presence of a mutation in the BRCA1 gene. In some embodiments, the method is a high throughput automated DNA sequencing or mutation detection methods commonly known by a one of ordinary skill in the art. In another embodiment, the output data from the detection module is analyzed using a computer system or computer readable media as disclosed herein, or in an alternative embodiment, the output data of the detection module is received by the storage module which is connected to the comparison module of a machine as described herein.

In another embodiment, the presence of a mutation in the RING domain and/or BRCT domain of BRCA1 can be determined in a biological sample taken from a subject, where a biological sample is placed into a detection module which determines the presence of a mutation in the RING domain and/or BRCT domain of the BRCA1 gene in the biological sample, where the output data of the detection module is received by the storage module which is connected to the comparison module of a machine as described herein, or in an alternative embodiment, the output data of the detection module is analyzed by the computer system and computer readable media as disclosed herein.

In some embodiments, a subject identified to be responsive to a topo I inhibitor by the methods, kits, machines, computer systems and computer readable media as disclosed herein (e.g., a subject who has a mutation in the BRCA1 RING domain (which decreases the E3 ligase activity of BRCA1 and/or interrupts or decreases the binding affinity of RING domain of BRCA1 with its binding partner BARD1 or an E2 conjugating enzyme (e.g., including but limited to UbCH5 and UbCH7)) and/or a mutation in the BRCT domain (e.g., a mutation in the BRCT domain which decreases the binding affinity of BRCT domain of BRCA1 with phosphor-ser10-topo I) can be administered a pharmaceutical composition comprising a topo I inhibitor as disclosed herein.

In some embodiments as disclosed herein, a machine can be used to determine the presence of a mutation in the RING domain and/or BRCT domain of the BRCA1 gene which interrupts its interaction with phosphor-ser10-topo I protein and/or decreases BRCA1 ubiquitination in a biological sample, for example, a machine for obtaining data regarding a biological sample from a subject comprising: a biological sample container to hold the biological sample; a determination module configured to detect the presence of a mutation in the RING domain and/or BRCT domain of the BRCA1 gene which interrupts its interaction with phosphor-ser10-topo I protein and/or decreases its ubiquitination, which produces output data, in some embodiments the output data in a computer readable media format; a storage device configured to store the output data from the determination module; a comparison module adapted to compare the output data from the determination module with data stored on the storage device, such as stored reference data and control data, and a display module for displaying a page of retrieved content for the user on a client computer, wherein the retrieved content comprises any one or a combination of the following; (i) the presence or absence of a mutation in the BRCA1 RING domain (e.g., a mutation in the RING domain which decreases the E3 ligase activity of BRCA1 and/or interrupts or decreases the binding affinity of RING domain of BRCA1 with its binding partner BARD1 or an E2 conjugating enzyme (e.g., including but limited to UbCH5 and UbCH7)) and/or a mutation in the BRCT domain (e.g., a mutation in the BRCT domain which decreases the binding affinity of BRCT domain of BRCA1 with phosphor-ser10-topo I); (ii) identification of a particular mutation in the RING domain and/or BRCT domain of the BRCA1 gene which interrupts its interaction with phosphor-ser10-topo I protein and/or decreases its ubiquitination (iii) a positive test result (i.e. the presence of a mutation in the RING domain and/or BRCT domain of the BRCA1 gene which interrupts its interaction with phosphor-ser10-topo I protein and/or decreases its ubiquitination) which indicates that the subject is likely to be responsive to a Topo I inhibitor than a subject having a cancer not having the mutation, (iv) a negative test result (i.e. an indication of the absence of a mutation in the RING domain and/or BRCT domain of the BRCA1 gene which interrupts its interaction with phosphor-ser10-topo I protein or decreases its ubiquitination) which indicates that the subject is more likely to be unresponsive to a Topo I inhibitor than a subject having a cancer with a mutation in the RING domain and/or BRCT domain of the BRCA1 gene which interrupts its interaction with phosphor-ser10-topo I protein.

One aspect of the present invention is a computer system that can be used to determine if a subject is responsive to a topo I inhibitor. In such an embodiment, a computer system is connected to a determination module and is configured to obtain output data from a determination module regarding a biological specimen, where a determination module is configured to detect the presence of a mutation in the RING domain and/or BRCT domain of the BRCA1 gene which interrupts its interaction with phosphor-ser10-topo I protein in a biological sample obtained from the subject; and where the computer system comprises (a) a storage device configured to store data output from the determination module as well as reference data; where the storage device is connected to (b) a comparison module which in one embodiment, is adapted to compare the output data stored on the storage device with stored reference data, and in alternative embodiments, adapted to compare the output data with itself, where the comparison module produces report data and is connected to (c) a display module for displaying a page of retrieved content (i.e. report data from the comparison module) for the user on a client computer, wherein the retrieved content comprises any one or a combination of the following; (i) the presence or absence of a mutation in the RING domain and/or BRCT domain of the BRCA1 gene which interrupts its interaction with phosphor-ser10-topo I protein; (ii) identification of a particular mutation in the RING domain and/or BRCT domain of the BRCA1 gene which interrupts its interaction with phosphor-ser10-topo I protein (iii) a positive test result (i.e. the presence of a mutation in the RING domain and/or BRCT domain of the BRCA1 gene which interrupts its interaction with phosphor-ser10-topo I protein or decreases its ubiquitination) which indicates that the subject is likely to be responsive to a Topo I inhibitor than a subject having a cancer not having the mutation, (iv) a negative test result (i.e. an indication of the absence of a mutation in the RING domain and/or BRCT domain of the BRCA1 gene which interrupts its interaction with phosphor-ser10-topo I protein or decreases its ubiquitination) which indicates that the subject is more likely to be unresponsive to a Topo I inhibitor than a subject having a cancer with a mutation in the RING domain and/or BRCT domain of the BRCA1 gene which interrupts its interaction with phosphor-ser10-topo I protein.

In some embodiments the comparison module compares the output data stored on the storage device with itself or stored reference data, and identifies the presence of a mutation in the RING domain and/or BRCT domain of the BRCA1 gene which interrupts its interaction with phosphor-ser10-topo I protein in a biological sample obtained from the subject which indicates a positive test result and generates report data to indicate that the subject is predicted to be responsive to a topo I inhibitor than a subject having a cancer with the absence of such a mutation, where the report data from the comparison module is retrieved from the display module and displayed on the display module.

One aspect of the present invention and all other aspect described herein, one can use a computer readable media to determine the presence of a mutation in the RING domain and/or BRCT domain of the BRCA1 gene which interrupts its interaction with phosphor-ser10-topo I protein or decreases its ubiquitination in a biological sample obtained from the subject having or at risk of having cancer, for example, a computer readable media having computer readable instructions recorded thereon to define software modules including a determination module and a comparison module for implementing a method on a computer, said method comprising: a storage device configured to store data reference data and output data from a determination module which has measured the presence or absence of a mutation in the RING domain and/or BRCT domain of the BRCA1 gene which interrupts its interaction with phosphor-ser10-topo I protein or decreases its ubiquitination; a comparison module which generates report data, where the comparison module is adapted to compare the data stored on the storage device, for example a comparison of output data from the determination module with itself or alternatively with reference data, and a display module for displaying a page of retrieved content which is the report data from the comparison module for the user on a client computer.

Another aspect of the present invention also relates to a method to predict if a subject with cancer will likely be responsive to a topoisomerase I inhibitor, the method comprising measuring for the presence of at least one mutation in the RING domain and/or BRCT domain of the BRCA1 gene which interrupts its interaction with phosphor-ser10-topo I protein or decreases its ubiquitination in a biological sample obtained from the subject, wherein the presence of such a mutation indicates that the subject with cancer is predicted to likely be responsive (e.g., sensitive) to a topoisomerase I inhibitor as compared to a subject where no mutation in the RING domain and/or BRCT domain of the BRCA1 gene which interrupts its interaction with phosphor-ser10-topo I protein or decreases its ubiquitination is detected.

Another aspect of the present invention relates to a method for treating cancer in a subject, the methods comprising: (i) measuring the presence of at least one mutation in the RING domain and/or BRCT domain of the BRCA1 gene which interrupts its interaction with phosphor-ser10-topo I protein or decreases its ubiquitination in a biological sample obtained from the subject; (ii) administering to the subject a topo I inhibitor where a mutation in the RING domain and/or BRCT domain of the BRCA1 gene which interrupts its interaction with phosphor-ser10-topo I protein or decreases its ubiquitination is detected, (iii) or alternatively, administering to the subject an anti-cancer agent other than a topoisomerase I inhibitor where a mutation in the RING domain and/or BRCT domain of the BRCA1 gene which interrupts its interaction with phosphor-ser10-topo I protein or decreases its ubiquitination is not detected.

In some embodiments, a topo I inhibitor is an antagonist of a topo I polypeptide of SEQ ID NO: 2 or a variant thereof, where an antagonist of a topo I polypeptide is any agent commonly known by one of ordinary skill in the art that inhibits the gene expression and/or the biological activity of a topo I polypeptide, and includes for example, but are not limited to agents such as antibodies, antibody fragments, small molecules, peptides, proteins, antisense nucleic acids, ribosomes, PNA, siRNA, oligonucleotides, aptamer, and peptide aptamer and derivatives and fragments thereof. In some embodiments, an antagonist of a topo I polypeptide useful in the methods of the present invention can be a nucleic acid-based inhibitor, nucleic acid construct, a peptide-based inhibitor or a small molecule inhibitor of topo I polypeptide or a polynucleotide encoding the same. In some embodiments a nucleic-acid inhibitor may be a RNAi (RNA interference) agent, such as for example a siRNA molecule or an antisense construct. Exemplary topo I inhibitors are disclosed herein, and include but are not limited to CPT, or analogues thereof such as topotecan and irinotecan. It is encompassed that the present invention provides methods, kits, machines, computer systems and computer readable media for determining if a subject is responsive to a topo I inhibitor regardless what the topo inhibitor is being used for. In some embodiments, the topo I inhibitor is being used as an anti-cancer treatment, including therapeutic and prophylactic anti-cancer treatment, however, a topo I inhibitor can be used for the treatment of non-cancer diseases or disorders where use of a topo I inhibitor is desired, for example any treatment strategy where cell death is the desired outcome.

In some embodiments, the disclosed methods, kits, machines, computer systems and computer readable media are useful for determining if a subject is likely to be responsive to a topo I inhibitor, and where a topo I inhibitor is used in the treatment of cancer, the present invention is useful in the prevention and/or treatment of cancers such as, but are not limited to, breast cancer, and ovarian cancer. In some embodiments, the cancer is any one of the following cancers, SCLC cancer, colon cancer, ovarian cancer, or a refractory cancer, for example, breast cancer or cervical cancer. In other embodiments, a cancer useful to be treated in the methods as disclosed herein is any cancer which can be treated, or is desirable to be treated with a topo I inhibitor and can be selected from any cancer in the group consisting of: gastrointestinal cancer, gastric cancer, squamous cell carcinomas (SCC), head and neck cancer, lung cancer, non-small cell lung cancer (NSCLC) and small-cell lung cancer (SCLC), lymphoma, sarcoma, primary and metastic melanoma, thymoma, non-Hodgkin's lymphoma, Hodgkin's lymphoma, cancer of the nervous system, brain cancer, bone-marrow cancer, bone cancer, kidney cancer, uterine cancer, cervical cancer, colon cancer, retina cancer, skin cancer, bladder cancer, colon cancer, esophageal cancer, testicular cancer, cervical cancer, liver cancer, renal cancer, pancreatic cancer, genital-urinary cancer, gastrointestinal, gum cancer, tongue cancer, kidney cancer, nasopharynx cancer, stomach cancer, endometrial cancer and bowel tumor cell cancer, adrenocarcinomas such as prostate cancer, ovarian cancer, breast cancer, and pancreatic cancer. In particular, the cancer is breast cancer, for example the triple-negative subtype of breast cancer. In one embodiment, a topo I inhibitor is used to treat cancer. In some embodiment the cancer is epithelial in origin, for example, the cancer is, but is not limited to; gastrointestinal cancer, prostate cancer, ovarian cancer, breast cancer, head and neck cancer, lung cancer, small-cell lung cancer, cancer of the nervous system, kidney cancer, retina cancer, skin cancer, liver cancer, pancreatic cancer, genital-urinary cancer and bladder cancer.

In some aspects of the invention, if a subject is identified to be responsive to a topo I inhibitor, a pharmaceutical composition comprising a topo I inhibitor as disclosed herein can be administered alone or with one or more other therapeutic agents. For example, in the treatment of cancer, the pharmaceutical composition can be administered substantially at the same time as, or subsequent to administration of an anti-cancer therapy, such as, for example, chemotherapy, radiotherapy, hormone therapy, thermal therapy, immunotherapy, surgical resection and alternative cancer therapies commonly known by persons of ordinary skill in the art. Such anti-cancer therapies can be administered prior to, during or after administration of the pharmaceutical composition as disclosed herein. In some embodiments, the anti-cancer therapy is administered once, or more than once to the subject.

It is contemplated that any methods or compositions described herein can be implemented with respect of any other methods or compositions. Other objects, features and advantages will become apparent from the following detailed description. It should be understood, however, that the detailed description and specific examples, while indicating specific embodiments of the invention, are given by way of illustration only, since various changes and modifications within the spirit and scope if the invention will become apparent to those skilled in the art from this detailed description.

BRIEF DESCRIPTION OF THE FIGURES

FIG. 1A shows HeLa cells were lysed and cell lysates were subjected to immunoprecipitation with anti-BRCA1 and IgG (control). After extensive washing, immunoprecipitates were analyzed by immunoblotting with anti-topoI. FIG. 1B. In a reciprocal immunoprecipitation, HCT15 cell lysates were subjected to immunoprecipitation with anti-topoI. After extensive washing, immunoprecipitates were analyzed by immunoblotting with anti-BRCA1. FIG. 1C. To determine the direct binding of topo I with the BRCA1-BRCT domain, HeLa cell nuclear lysates were incubated with GST (control) and GST-topo I bound to glutathione sepharose and after extensive washing with PBS, the adsorbates were analyzed by immunoblot analysis with anti-topoI.

FIG. 2A shows GST-topo I bound to glutathione beads were phosphorylated by DNA-PK. Phosphorylated GST-topo I was incubated with purified E1, UbcH5c (E2), and BRCA1/BARD1 (E3) (lane2). Phosphorylated topo I was also incubated with E1 and UbcH5c (E2) only as control (lane 1). Reactions were carried out in ubiquitination buffer at 37° C. for 30 min. The reaction products were analyzed by immunoblot analysis with anti-ubiquitin. FIG. 2B shows HCC1937 and HCC1937-BRCA1 cells were treated with SN-38, control cells treated with DMSO (C) and treated cells (T) were lysed and cell lysates were subjected to immunoprecipitation with anti-topoI. Immunoprecipitates were analyzed by immunoblot analysis with anti-ubiquitin. FIG. 2C shows HCC1937 and HCC1937-BRCA1 cells were treated with 5 uM CPT and harvested after 30 minutes, 1 hour and 1.5 hours. Control and treated cells were harvested and lysed. Cell lysates were analyzed by immunoblot analysis with anti-topo I (upper panel) and anti-β-actin (lower panel). FIG. 2D shows HCC1937 and HCC1937-BRCA1 cells were treated with different concentrations of SN-38 and were analyzed for percent cell growth inhibition by Celigo after 72 hours.

FIG. 3A-3C shows the rate of topo I degradation determines the cellular response to CPT in NBC cells. FIG. 3A shows that four TNBC cells (BT20, BT549, MDA-MB-231, and SUM52) were treated with SN38. Cells were harvested after designated time and lysed. The cell lysates were analyzed by immunoblot analysis with anti-topo I (upper panel) and anti-β-actin for equal protein loading (lower panel). An infrared secondary antibody was used and a LICOR system was used to visualize the florescence. FIG. 3B shows TNBC control (C) and treated (T) cells were also subjected to immunoprecipitation with anti-topoI. Immunoprecipitates were analyzed by immunoblot analysis with anti-Pan ubiquitin. FIG. 3C shows 5,000-7,000 TNBC cells were plated with Hoechst DNA dye in a 96 well plate. The cell number was counted after 12 hours using a Celigo system. The cells were treated with 10 and 25 nM SN-38 for 72 hours. The cells were counted again using the Celigo system and growth inhibition was determined using a formula described in the materials and methods section.

FIG. 4A shows BT474 cells were subjected to silencing of BRCA1 by shRNA delivered through viral transduction. FIG. 4B shows immunoblot analysis with anti-topo I of BRCA1-silenced and unsilenced BT474 cells showing treatment with CPT for 2 and 6 hours. Protein levels in FIGS. 4A and 4B were determined by immuno blot analysis of cell lysate with anti-βactin. FIG. 4C shows quantification of % topo I expression level in siRNA treated siBRCA1 cells as compared to control cells following treatment with CPT for 0, 3 and 6 hours (FIG. 5B)

FIG. 5A shows that due to the presence of CPT topo I fails to relegate the cleaved DNA during the relegation cycle. The collision of replication fork with cleaved DNA leads to DNA-double strand breaks (DNA-DSB). To repair the DNA-DSB topo I is removed by ubiquitination proteosomal pathway (UPP). The inventors have previously demonstrated, as shown by the schematic in FIG. 5B, that topo I associates with Ku-DNA-PK complex, and that DNA-DSB mediated activation of DNA-PK phosphorylates topo I at S10. FIG. 5C is a schematic demonstrating the phosphorylation of topo I at S10 ensures the ubiquitination of topo I by BRCA1/BARD1 heterodimer, and subsequent degradation of the ubiquitinated topo I by ubiquitin-proteosomal pathway.

FIG. 13A shows that HCC-1937 (BRCA1 mutant and deficient in E3 ligase function) and HCC1937-BRCA1 (wild type BRCA1 with efficient BRCA1-E3 ligase function) cells were treated with 5 µM CPT and harvested after 30 minutes, 1 hour and 1.5 hours. Control and treated cells were harvested and lysed. Cell lysates were analyzed by immunoblot analysis with anti-topo I (upper panel) and anti-β-actin (lower panel). FIG. 13B shows HCC1937 and HCC1937-BRCA1 cells were Control (C) and CPT treated (T) were lysed and cell lysates were subjected to immunoprecipitation with anti-topoI. Immunoprecipitates were analyzed by immunoblot analysis with anti-ubiquitin. FIG. 13C shows HCC1937 and HCC1937-BRCA1 cells were treated with different concentrations of SN-38 and were analyzed for percent cell growth inhibition after 72 hours.

DETAILED DESCRIPTION OF THE INVENTION

Figure 1A:
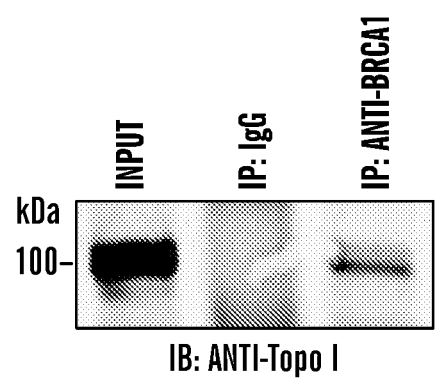
FIG. 1A-1C show BRCA1 associates with topoI.

The present invention generally relates to a diagnostic marker for predicting the efficacy of topoisomerase I (topo I) inhibitors in the treatment of cancers. In particular, one aspect of the present invention relates to methods to determine effectiveness of topoisomerase I (topo I) inhibitors in the treatment of cancer. The inventors have previously demonstrated that the topo I polypeptide is phosphorylated at serine 10 (S10) by the kinase DNA-PK and results in its ubiquitination by its interaction with the BRAC1/BARD1 heterodimer and its subsequent degradation, as disclosed in US Application 2011/0027277, which is incorporated herein in its entirety by reference. The presence of phosphorylation of a topo I polypeptide (herein referred to as "phospho-topo I"), in particular the phosphorylation at the serine 10 (S10) amino acid residue of a topo I polypeptide (herein referred to as "phospho-S10 topo I") in a biological sample indicates the resistance and/or unresponsiveness to a topo I inhibitor, such as camptothecin (CPT), or CPT analogues such as topotecan and irinotecan and derivatives thereof. Thus, the presence of phosphorylation of topoI, in particular the phosphorylation of topo I on serine 10 (S10) indicates rapid topo I degradation and resistance to topo I inhibitors such as camptothecin (CPT), or CPT analogues such as topotecan and irinotecan and derivatives thereof. This degradation is dependent on the BRCT domain on BRCA1 interacting with phospho-ser10-topo I.

The present invention is based on the discovery that mutations in the BRCA1 gene which interrupt and/or decrease the interaction of BRCA1 with phosphor-ser10-topo I polypeptide and/or decrease the ubiquitination of phospho-ser10 topo I, result in decreased degradation of phospho-ser10-topo I polypeptide and thus a subject with such mutations are predicted to be responsive (e.g., sensitive) to topo I inhibitors, such as such as camptothecin (CPT), or CPT analogues such as topotecan and irinotecan and derivatives thereof. Stated another way, when topo I is phosphorylated on serine 10, it is subsequently ubiquitinated by the BRCA1/BARD1 heterodimer and degraded. Consequently, this reduces the amount of the phosphor-ser10-topoI protein available for inhibition by topo I inhibitors, and thus such inhibitors are generally ineffective as therapeutic agents. The presence of a mutation in the BRCA1 RING domain (e.g., a mutation in the RING domain which decreases the E3 ligase activity of BRCA1 and/or interrupts or decreases the binding affinity of RING domain of BRCA1 with its binding partner BARD1 or an E2 conjugating enzyme (e.g., including but limited to UbCH5 and UbCH7)) and/or a mutation in the BRCT domain (e.g., a mutation in the BRCT domain which decreases the binding affinity of BRCT domain of BRCA1 with phosphor-ser10-topo I) thus reduces the ubiquitination of phospho-ser10 topo I by the BRCT/BARD1 domain, and this reduces is degradation, and thus topo I inhibitors will generally be affective, and the subject will be responsive to topo I inhibitors for therapeutic purposes.

Accordingly, herein the inventors have demonstrated that a subject with one or more mutations in the BRCA1 protein, e.g., a mutation in any one or more of (i) the BRCA1 RING domain, (ii) the BRCT domain of BRCA1, or (iii) the E3 ligase domain of BRCA1 which impairs the E3 ligase activity, will identify the subject to be responsive (e.g., sensitive) to topo I inhibitors such as camptothecin (CPT), or CPT analogues such as topotecan and irinotecan and derivatives thereof. Accordingly, the inventors have discovered that mutations in the BRCT domain of BRCA1 which disrupt or impair the interaction of BRCT with the phospho-topo I protein will reduce topo I protein degradation and thus increase the sensitivity of the subject to topo I inhibitors.

Accordingly, one aspect of the present invention relates to detection of mutations in BRCA1 in a biological sample from a subject with cancer, as a prognostic determinant for drug efficacy with topo I inhibitors such as CPT and its analogues.

One aspect of the present invention relates to methods and compositions to determine if a topoisomerase I inhibitor is effective in a subject with cancer. One aspect of the present invention relates to a method to determine the presence of one or more mutations in BRCA1 gene, e.g., in the RING domain, and/or BRCT domain and/or a mutation which disrupts E3 ligase activity of BRCA1, wherein the presence of such a mutation indicates that the subject having such cancer will likely be responsive (or sensitive) to a topo I inhibitor as compared to a subject with a cancer who does not have such mutations in the BRCA1 gene. In some embodiments, a mutation in the BRCA1 RING domain between amino acids 1-109 of SEQ ID NO: 6 which interrupt the binding of BRCA1 with BARD1 protein or an E2 conjugating enzyme (e.g., including but limited to UbCH5 and UbCH7) and/or decreases the E3 ligase activity of BRCA1 indicates that the subject carrying the mutation will be responsive to a topo I inhibitor, e.g., CPT or its analogues. In some embodiments, a mutation in the BRCA1 RING domain between amino acids 1-109 of SEQ ID NO: 6 is a mutation of a conserved amino acid residue which interrupt the binding of BRCA1 with BARD1 protein or an E2 conjugating enzyme (e.g., including but limited to UbCH5 and UbCH7) and/or decreases the E3 ligase activity of BRCA1.

In another embodiment, a mutation in the BRCA1 BRCT domain between or inclusive of amino acids 1650-1863 of SEQ ID NO: 6 which interrupts the binding of the BRCT1 domain of BRCA1 with the topo I phosphoprotein indicates that the subject carrying the mutation will be responsive to a topo I inhibitor, e.g., CPT or its analogues. In some embodiments, a mutation in the BRCA1 BRCT domain between or inclusive of amino acids 1650-1863 of SEQ ID NO: 6 is a mutation of a conserved amino acid residue which interrupts the binding of the BRCT1 domain of BRCA1 with the topo I phosphoprotein. In some embodiments, a mutation between, or inclusive of amino acids 1-109 or 1650-1863 which interrupts the BRCA1 binding with the topo I protein can be assessed by one of ordinary skill in the art using the fluorescence polarization assay as disclosed herein in the Examples.

In some embodiments, a mutation is any change of nucleic acid in BRCA1 gene (e.g., SEQ ID NO: 5) which changes the amino acid cysteine at position 39 (e.g., cystine39) of the BRAC1 protein (SEQ ID NO: 6), or changes the amino acid of the cysteine at position 61 (cystine61) in the RING domain of BRCA1 protein. In some embodiments, any mutation in the BRCA1 gene which results in C39A mutation, or a C64A will identify a subject will likely be responsive to a topo I inhibitor and thus be amenable to treatment with an topo I inhibitor as disclosed herein. In some embodiments, a mutation in the RING domain of the BRCA1, which decrease the RING E3 ligase activity and/or decrease the RING binding affinity for BARD1, and/or decreases the BRCA1 binding to an E2 conjugating enzyme (e.g., including but not limited to UbCH5 and UbCH7), can include, but not is limited to, mutations such as M18, C24R, I26A, T37, C39A, C39Y, C44F/G, C44F, I31M, L51A, C61G, C64A, C64Y, T73R, C44F, C47F/G.

In some embodiments, mutations in the RING domain of the BRCA1, which decrease the RING E3 ligase activity and/or decrease the RING binding affinity for BARD1 and/or BRCA1 binding affinity for an E2 conjugating enzyme (e.g., including but limited to UbCH5 and UbCH7), can include any mutation which decreases the E3 ligase activity of BRCA1 by at least 10% as compared to wild type BRCA1 gene, and/or decreases the binding affinity of RING domain of BRCA1 with its binding partner BARD1 by at least 10% as compared to the wild type BRCA1 gene and/or a decrease of about 10% of BRCA1 binding affinity for an E2 conjugating enzyme (e.g., including but limited to UbCH5 and UbCH7) as compared to the wild-type BRCA1 gene.

In another embodiment, the mutation in the RING domain causes a decreases in the E3 ligase activity of BRCA1 and/or a decrease in the binding affinity of the RING domain of BRCA1 with its binding partner BARD1 or an E2 conjugating enzyme (e.g., including but limited to UbCH5 and UbCH7) by a statistically significant amount, e.g., at least one standard deviation, more preferably by at least two standard deviations as compared to the E3 ligase activity of BRCA1 and/or binding affinity of the RING domain of BRCA1 with its binding partner BARD1 or an E2 conjugating enzyme of wildtype BRCA1 gene.

In some embodiments, a mutations in the BRCT domain for use in the methods and systems and assays as discussed herein include any mutation which decreases the binding affinity of BRCT domain of BRCA1 with phosphor-ser10-topo I by at least 10% as compared to a wild type BRCA1 protein.

In some embodiments, the mutation in the BRCT domain causes a decrease in the binding affinity of BRCT domain with phospho-ser10 topoI by a statistically significant amount, e.g., at least one standard deviation, more preferably by at least two standard deviations as compared to the binding affinity of BRCT domain with phospho-ser10 topoI by the wildtype BRCA1 gene.

In some embodiments, the mutation is a change of nucleic acid which results in a change of the amino acid arginine at position 1699 (e.g., arginine1699) in the BRCT domain of the BRCA1 protein, for example a nucleic acid change which results in arginine 1699 changing to tryptophan (R1699W). In some embodiments, the mutation is a change of nucleic acid which results in a change of the amino acid glutamic acid at position 1836 (e.g., glutamic acid 1836) in the BRCT domain, for example a change of glutamic acid 1836 to lysine (G1656D). In some embodiments, a mutation in the BRCT domain of BRCA1 which interrupt or decrease the binding of BRCA1 to the topo I protein can be any of the group selected from G1656D, T1700A, R1699Q, R1699W, M1775R, M1775K, R1835P or E1836K.

Accordingly, one aspect of the present invention relates to detection in a biological sample from a subject with cancer of at least one mutation in the RING domain and/or BRCT domain of BRCA1 gene which interrupts or decreases the interaction of BRCA1 with the phospho-ser10-topo I protein and/or decreases its ubiquitination, where the biological sample is taken from a subject having, or likely having cancer, as a prognostic determinant for drug efficacy with a topo I inhibitor such as CPT and analogues thereof.

Accordingly, one aspect of the present invention relates to methods, kits, machines, computer systems and computer readable media to detect and analyze, in a biological sample obtained from a subject, the presence of at least one mutation in the RING domain and/or BRCT domain of BRCA1 gene which interrupts or decreases the interaction of BRCA1 with the phospho-ser10-topo I protein and/or decreases its ubiquitination, and if the subject, or biological sample is determined to have at least one mutation in the RING domain and/or BRCT domain of BRCA1 gene which interrupts or decreases the interaction of BRCA1 with the phospho-ser10-topo I protein and/or decreases its ubiquitination, then the subject, or the subject from which the biological sample was obtained is identified as being likely to be responsive to a topo I inhibitor such as camptothecin (CPT), or CPT analogues such as topotecan and irinotecan and derivatives thereof, as compared to a subject not having a mutation in the RING domain and/or BRCT domain of BRCA1 gene which interrupts or decreases the interaction of BRCA1 with the phospho-ser10-topo I protein and/or decreases its ubiquitination.

Accordingly, another aspect of the present invention provides a method to identify a subject which is responsive to a topo I inhibitor, such as for example where the subject is currently undergoing or has been selected to be treated for cancer with a topo I inhibitor, for example but not limited to CPT or analogues such as topotecan and irinotecan and other analogues or derivatives thereof.

One aspect of the present invention relates to a method for identifying a subject responsive to a topo I inhibitor, the method comprising detecting at least one mutation in the RING domain and/or BRCT domain of BRCA1 gene which interrupts or decreases the interaction of BRCA1 with the phospho-ser10-topo I protein and/or decreases its ubiquitination, and if such mutation is detected, it indicates that the subject is likely to be responsive to a topoisomerase I inhibitor for the treatment of cancer as compared to a subject not having a mutation in the RING domain and/or BRCT domain of BRCA1 gene which interrupts or decreases the interaction of BRCA1 with the phospho-ser10-topo I protein and/or decreases its ubiquitination In some embodiments, a topo I inhibitor useful in the methods as disclosed herein is any agent or entity which inhibits the biological activity, such as protein activity of topoisomerase, including but not limited to camptothecin (CPT), or CPT analogues such as topotecan and irinotecan and derivatives thereof, CPT compounds, CPT metabolites, CPT derivatives and mimetics thereof.

In an alternative embodiment, a subject identified to be responsive to a topo I inhibitor can be administered a topo I inhibitor, such as for example but not limited to CPT or analogues thereof.

In one embodiment the cancer is SCLC, colon or ovarian cancer, or a refractory cancer, for example, breast cancer or cervical cancer. In other embodiments, a cancer useful to be treated in the methods as disclosed herein is any cancer which can be treated, or is desirable to be treated with a topo I inhibitor and includes, for example but are not limited to cancers comprising those of epithelial origin, including, but are not limited to, gastrointestinal cancer, prostate cancer, ovarian cancer, breast cancer, head and neck cancer, lung cancer, non-small cell lung cancer, cancer of the nervous system, kidney cancer, retina cancer, skin cancer, liver cancer, pancreatic cancer, genital-urinary cancer and bladder cancer. In one embodiment, the cancer is non-small cell lung cancer. In another embodiment, the cancer is triple-negative subtype of cancer, which lacks the expression of the progesterone receptor (PR), the estrogen receptor (ER) and also lacks Her-2 amplification.

Tumor cell types can also be selected from a group comprising of gastrointestinal cancer, gastric cancer, squamous cell carcinomas (SCC), head and neck cancer, lung cancer, non-small cell lung cancer (NSCLC) and small-cell lung cancer (SCLC), lymphoma, sarcoma, primary and metastatic melanoma, thymoma, non-Hodgkin's lymphoma, Hodgkin's lymphoma, cancer of the nervous system, brain cancer, bone-marrow cancer, bone cancer, kidney cancer, uterine cancer, cervical cancer, colon cancer, retina cancer, skin cancer, bladder cancer, colon cancer, esophageal cancer, testicular cancer, cervical cancer, liver cancer, renal cancer, pancreatic cancer, genital-urinary cancer, gastrointestinal, gum cancer, tongue cancer, kidney cancer, nasopharynx cancer, stomach cancer, endometrial cancer and bowel tumor cell cancer, adrenocarcinomas such as prostate cancer, ovarian cancer, breast cancer, and pancreatic cancer.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "topoisomerase I" is used interchangeably herein with "topo I" and refers to the polypeptide encoded by SEQ ID NO: 2 and variants and homologues thereof, including conservative substitutions, additions, deletions therein not adversely affecting the structure of function. Topoisomerase I is referred in the art as TOPI or TOP1. Human topo I is encoded by nucleic acid corresponding to GenBank Accession No: BC136297.1 (SEQ ID NO: 3) or GI:223460079 and the human topo I polypeptide corresponds to protein sequence corresponding to RefSeq ID No: NM_003286 or NP_003277.1. DNA topoisomerase is an enzyme that controls and alters the topologic states of DNA during transcription, and catalyzes the transient breaking and rejoining of a single strand of DNA which allows the strands to pass through one another, thus altering the topology of DNA. The gene for TOP1 is localized to chromosome 20 and has pseudogenes which reside on chromosomes 1 and 22. The biological activity of topo I polypeptide refers to the polypeptides enzymatic activity to catalyze the transient breaking and rejoining of a single strand of DNA, where one strand pass through one another, thus altering the topology of DNA.

The term "inhibitor" as used herein refers to any agent or entity which results in the inhibition of a proteins biological activity. By a "decrease" or "inhibition" used in the context of the level of activity of a gene refers to a reduction in protein or nucleic acid level or biological activity in a cell, a cell extract, or a cell supernatant. For example, such inhibition may be due to decreased binding of the polypeptide to its endogenous ligand, or by non-completive binding of an inhibitor to a polypeptide to reduce catalytic activity or affinity for target ligand etc., or alternatively to reduced RNA stability, transcription, or translation, increased protein degradation, or RNA interference. Preferably, a decrease is at least about 5%, at least about 10%, at least about 25%, at least about 50%, at least about 75%, at least about 80%, or even at least about 90% of the level of expression or activity under control conditions. The term "inhibiting" as used herein as it pertains to the inhibition of the activity of topoisomerase I protein or variants thereof does not necessarily mean complete inhibition of expression and/or activity. Rather, expression or activity of the protein, polypeptide or polynucleotide is inhibited to an extent, and/or for a time, sufficient to produce the desired effect.

The terms "lower", "reduced", "reduction" or "decrease" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased", "increase" or "enhance" or "higher" are all used herein to generally mean an increase by a statically significant amount; for the avoidance of any doubt, the terms "increased", "increase" or "enhance" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

By an "increase" in the expression or activity of a gene or protein is meant a positive change in protein or polypeptide or nucleic acid level or activity in a cell, a cell extract, or a cell supernatant. For example, such a increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

As used herein, the term "gene" includes a segment of DNA that contains all the information for the regulated biosynthesis of an RNA product, including promoters, exons, introns, and other untranslated regions that control expression. Those in the art will readily recognize that nucleic acid molecules can be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense) strand of a nucleic acid molecule is also intended to include the thymine (uridine), adenine, guanine, or cytosine (respectively) at the corresponding site on a minus (antisense) strand of a complementary strand of a nucleic acid molecule. Thus, reference can be made to either strand and still comprise the same polymorphic site and an oligonucleotide can be designed to hybridize to either strand. Throughout this specification, in identifying a polymorphic site, reference is made to the sense strand, only for the purpose of convenience. As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or RNA, the terms "adenosine", "cytosine", "guanosine", and "thymidine" are used. It is understood that if the nucleic acid is RNA, a nucleotide having a uracil base is uridine. The term "nucleotide" or nucleic acid as used herein is intended to refer to ribonucleotides, deoxyribonucleotides, acyclic derivatives of nucleotides, and functional equivalents thereof, of any phosphorylation state. Functional equivalents of nucleotides are those that act as substrates for a polymerase as, for example, in an amplification method. Functional equivalents of nucleotides are also those that can be formed into a polynucleotide that retains the ability to hybridize in a sequence specific manner to a target polynucleotide. As used herein, the term "polynucleotide" includes nucleotides of any number. A polynucleotide includes a nucleic acid molecule of any number of nucleotides including single-stranded RNA, DNA or complements thereof, double-stranded DNA or RNA, and the like.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A "polymorphic gene" refers to a gene having at least one polymorphic region.

The term "genotype" refers to the specific allelic composition of an entire cell or a certain gene, whereas the term "phenotype" refers to the detectable outward manifestations of a specific genotype.

The term "variant", "variance", "mutation" or "polymorphism" are used interchangeably herein and as used herein with respect to nucleic acid sequence refers to a difference in nucleic acid sequence in the population. Polymorphisms are sometimes referred to as "single nucleotide polymorphism" or "SNP" can be synonymous or non-synonymous. Synonymous polymorphisms when present in the coding region typically do not result in an amino acid change. Non-synonymous polymorphism when present in the coding region alter one or more codons resulting in an amino acid replacement in the amino acid chain. Such mutations and polymorphisms can be either heterozygous or homozygous within an individual. Homozygous individuals have identical alleles at one or more corresponding loci on homologous chromosomes. While heterozygous individuals have two different alleles at one or more corresponding loci on homologous chromosomes. A polymorphism is thus said to be "allelic," in that, due to the existence of the polymorphism, some members of a species carry a gene with one sequence (e.g., the original or wild-type "allele"), whereas other members can have an altered sequence (e.g., the variant or, mutant "allele"). In the simplest case, only one mutated variant of the sequence can exist, and the polymorphism is said to be diallelic. For example, if the two alleles at a locus are indistinguishable in their effects on the organism, then the individual is said to be homozygous at the locus under consideration. If the two alleles at a locus are distinguishable because of their differing effects on the organism, then the individual is said to be heterozygous at the locus. In the present application, typographically, alleles are distinguished "+" or "−". Using these symbols, homozygous individuals are +/+, or −/− or two of the same symbol, for example A/A, G/G, T/T and C/C. Heterozygous individuals are +/− or two different symbols, for example A/G, A/T. A/C, G/T etc. The occurrence of alternative mutations can give rise to tri-allelic and tetra-allelic polymorphisms, etc. An allele can be referred to by the nucleotide(s) that comprise the mutation. In some instances a "silent mutation" is a synonymous codon change, or silent SNP is one that does not result in a change of amino acid due to the degeneracy of the genetic code. A substitution that changes a codon coding for one amino acid to a codon coding for a different amino acid (i.e., a non-synonymous codon change) is referred to as a missense mutation. A nonsense mutation results in a type of non-synonymous codon change in which a stop codon is formed, thereby leading to premature termination of a polypeptide chain and a truncated protein. A read-through mutation is another type of non-synonymous codon change that causes the destruction of a stop codon, thereby resulting in an extended polypeptide product. While SNPs can be bi-, tri-, or tetra-allelic, the vast majority of the SNPs are bi-allelic, and are thus often referred to as "bi-allelic markers", or "di-allelic markers".

The term "BRCA1 protein" as used herein is intended to include all isoforms of the BRCA1 protein, which encompasses BRCA1 proteins with amino-acid sequence variations, as well as pre- and post-translationally modified BRCA1 proteins. Any post-translational modification is encompassed, for example but not limited to glycosylation, phosphorylation, sumoylation, truncation and ectodomain shedding etc. The term BRCA1 protein is also intended to encompass all isoforms of BRCA1, for example truncated forms of BRCA1 and mature BRCA1 as well as other BRCA1 isoforms and variants. Isoforms of BRCA1 protein useful in the present invention are fragments of the BRCA1 protein, and include, but is not limited to isoforms of the following sizes; between 140-170 kDa, 97 kDa, between 70-66 kDa, 50 kDa, 42 kDa, 35 kDa, 20 kDa and 6 kDa. The coding sequence for the wild type BRCA1 polypeptide is shown in SEQ ID NO:1, with the amino acid sequence for wild type BRCA1 protein is shown in SEQ ID NO:2. The amino acid sequence of BRCA1 is also identified by 5 different transcripts NP_009225.1 NP_009228.2 NP_009229.2 NP_009230.2 NP_009231.2.

The term "BRCA1 mRNA" as used herein is intended to include all BRCA1 mRNA species or variants and all post-transcription RNA products, for example mRNA products transcribed from the BRCA1 gene, such as but not limited to pre-mRNA and mature mRNA molecules. For example, the BRCA1 gene is transcribed into what is commonly referred to in the art as "preproBRCA1 mRNA", which is included in the term BRCA1 mRNA. Also encompassed in the term BRCA1 mRNA is pre-mRNA, mature mRNA molecules and alternatively spliced mRNA molecules of BRCA1.

The term "BRCA1 Allele" refers to normal alleles of the BRCA1 locus as well as alleles carrying variations that predispose individuals to develop cancer of many sites including, for example, breast, ovarian, colorectal and prostate cancer. Such predisposing alleles are also called "BRCA1 susceptibility alleles".

The term "BRCA1 Locus," "BRCA1 Gene," "BRCA1 Nucleic Acids" or "BRCA1 Polynucleotide" each refer to polynucleotides, all of which are in the BRCA1 region, that are likely to be expressed in normal tissue, certain alleles of which predispose an individual to develop breast, ovarian, colorectal and prostate cancers. Mutations at the BRCA1 locus may be involved in the initiation and/or progression of other types of tumors. The locus is indicated in part by mutations that predispose individuals to develop cancer. These mutations fall within the BRCA1 region described infra. The BRCA1 locus is intended to include coding sequences, intervening sequences and regulatory elements controlling transcription and/or translation. The BRCA1 locus is intended to include all allelic variations of the DNA sequence. These terms, when applied to a nucleic acid, refer to a nucleic acid which encodes a BRCA1 polypeptide, fragment, homolog or variant, including, e.g., protein fusions or deletions. The nucleic acids of the present invention will possess a sequence which is either derived from, or substantially similar to a natural BRCA1-encoding gene or one having substantial homology with a natural BRCA1-encoding gene or a portion thereof.

The term "BRCA1 Region" refers to a portion of human chromosome 17q21 bounded by the markers tdj 1474 and U5R. This region contains the BRCA1 locus, including the BRCA1 gene.

As used herein, the terms "BRCA1 locus," "BRCA1 allele" and "BRCA1 region" all refer to the double-stranded DNA comprising the locus, allele, or region, as well as either of the single-stranded DNAs comprising the locus, allele or region.

As used herein, a "portion" of the BRCA1 locus or region or allele is defined as having a minimal size of at least about eight nucleotides, or preferably about 15 nucleotides, or more preferably at least about 25 nucleotides, and may have a minimal size of at least about 40 nucleotides.

The term "BRCA1 protein" or "BRCA1 polypeptide" refer to a protein or polypeptide encoded by the BRCA1 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native BRCA1 sequence, preferably in excess of about 90%, and more preferably at least about 95% homologous. Also included are proteins encoded by DNA which hybridize under high or low stringency conditions, to BRCA1-encoding nucleic acids and closely related polypeptides or proteins retrieved by antisera to the BRCA1 protein(s).

The terms "BRCA1 polymorphism" as used herein refers to at least one polymorphic site in the polynucleotide or amino acid sequence of BRCA1 gene or gene product. For purposes of the present application, the wild-type polynucleotide encoding the BRCA1 is designated SEQ ID NO: 5 and the wild-type gene product comprising the BRCA1 molecule, is designated amino acid SEQ ID NO: 6.

The term "allele", which is used interchangeably herein with "allelic variant" refers to alternative forms of a gene or portions thereof and refers to a region of the gene of interest having one of a plurality of nucleotide sequences found in that region of the gene in other individuals. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions and insertions of nucleotides. An allele of a gene can also be a form of a gene containing a mutation.

The terms "polymorphic site with increased likelihood of developing cancer" includes associating the polymorphism which occurs at a higher allelic frequency or rate in individuals with the disease than individuals without the disease. Correlation of the disease with the polymorphism can be accomplished by bio-statistical methods known in the art, such as for example, by Chi-squared tests or other methods described by L. D. Fisher and G. vanBelle, Biostatistics: A Methodology for the Health Sciences, Wiley-Interscience (New York) 1993.

The term "wild-type allele" refers to an allele of a gene which, when present in two copies in a subject results in a wild-type phenotype. There can be several different wild-type alleles of a specific gene, since certain nucleotide changes in a gene can not affect the phenotype of a subject having two copies of the gene with the nucleotide changes The term "sample" as used herein generally refers to any material containing nucleic acid, either DNA or RNA or amino acids. Generally, such material will be in the form of a blood sample, stool sample, tissue sample, cells, bacteria, histology section, or buccal swab. Samples can be prepared, for example samples can be fresh, fixed, frozen, or embedded in paraffin.

The term "biological sample" as used herein refers to a cell or population of cells or a quantity of tissue or fluid from a subject. Most often, the sample has been removed from a subject, but the term "biological sample" can also refer to cells or tissue analyzed in vivo, i.e. without removal from the subject. Often, a "biological sample" will contain cells from the animal, but the term can also refer to non-cellular biological material, such as non-cellular fractions of blood, saliva, or urine, that can be used to measure gene expression levels. Biological samples include, but are not limited to, tissue biopsies, scrapes (e.g. buccal scrapes), whole blood, plasma, serum, urine, saliva, cell culture, or cerebrospinal fluid. Biological samples also include tissue biopsies, cell culture. A biological sample or tissue sample can refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the sample is from a resection, bronchoscopic biopsy, or core needle biopsy of a primary or metastatic tumor, or a cellblock from pleural fluid. In addition, fine needle aspirate samples are used. Samples can be either paraffin-embedded or frozen tissue. The sample can be obtained by removing a sample of cells from a subject, but can also be accomplished by using previously isolated cells (e.g. isolated by another person), or by performing the methods of the present invention in vivo. Biological sample also refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the biological samples can be prepared, for example biological samples can be fresh, fixed, frozen, or embedded in paraffin.

The term "isolated" as used herein refers to the state of being substantially free of other material such as nucleic acids, proteins, lipids, carbohydrates, or other materials such as cellular debris or growth media with which BRCA1 polynucleotide encoding BRCA1, primer oligonucleotide, or allele-specific oligonucleotide can be associated. Typically, the term "isolated" is not intended to refer to a complete absence of these materials. Neither is the term "isolated" generally intended to refer to water, buffers, or salts, unless they are present in amounts that substantially interfere with the methods of the present invention.

The term "expression" as used herein refers to interchangeably to the expression of a polypeptide or protein or expression of a polynucleotide or expression of a gene. Expression also refers to the expression of pre-translational modified and post-translationally modified proteins, as well as expression of pre-mRNA molecules, alternatively spliced and mature mRNA molecules. Expression of a polynucleotide can be determined, for example, by measuring the production of RNA transcript molecules, for example messenger RNA (mRNA) transcript levels. Expression of a protein or polypeptide can be determined, for example, by immunoassay using an antibody(ies) that bind with the polypeptide.

The term "encode" as it is applied to polynucleotides refers to a polynucleotide which is said to "encode" a polypeptide or protein if, in its native state or when manipulated by methods well known to those skilled in the art, it can be transcribed to produce the RNA which can be translated into an amino acid sequence to generate the polypeptide and/or a fragment thereof. The antisense strand is the complement of such a nucleic acid, and the encoding sequence can be deduced therefrom.

The term "endogenously expressed" or "endogenous expression" refers to the expression of a gene product at normal levels and under normal regulation for that cell type.

The term "interfere" or "interrupt" as disclosed herein as used in reference with a mutation or agent (e.g., test compound) which interrupts the binding of BRCA1 with phospho-ser10-topo I refers to an agent or mutation which decreases the binding affinity or binding interaction of BRCA1 with phospho-ser10-topo I by at least about 10%, or at least about 25%, or at least about 50%, or greater than 50%.

The term "binding affinity" refers to the strength of interaction between the two species or molecules. The binding affinity between the RING domain of BRCA1 and BARD1 and/or the binding affinity of BRCA1 for an E2 conjugating enzyme (e.g., including but limited to UbCH5 and UbCH7) can be assessed according to methods discussed in Ruffner et al., PNAS, 2001; 98 (9); 5134-5139, and the binding affinity of the BRCT domain of the BRAC1 can be assessed using the assays disclosed in the Examples, e.g., fluorescence polarization assays as disclosed herein.

As used herein, the terms "isoform", or "isoforms" or "variant of protein" are used interchangeably herein, refer to specific forms of the same protein, the specific form differing from other forms of the same protein in the sequence of at least one, and frequently more than one, amino acids. Isoforms are proteins produced from the same gene, due to, for example but not limited to, transcription from different promoters, alternative splicing, differential mRNA splicing and/or post-translational modification such as, for example, glycosylation, sumoylation, phosphorylation, truncation and ectodomain shedding.

The term "functional fragment" when used in conjunction with "derivative" or "variant" or "fragment" refers to a polypeptide which possess a biological activity that is substantially similar to a biological activity of the entity or molecule of which it is a derivative or variant or fragment thereof. By "substantially similar" in this context is meant that at least 25%, at least 35%, at least 50% of the relevant or desired biological activity of a corresponding wild-type peptide is retained. In the instance of a fragment of BRCA1 (e.g., SEQ ID NO: 2), would be a protein or peptide comprising a portion of SEQ ID NO: 2 which retained an activity for ubiquitinating phospho-ser10-topo I; preferably the fragment of SEQ ID NO: 2 that retains at least 25%, at least 35%, at least 50% at least 60%, at least 70%, at least 80%, at least 90%, at least 95%, at least 100% or even higher (i.e., the variant or derivative has greater activity than the wild-type), e.g., at least 110%, at least 120%, or more activity compared to the full length SEQ ID NO: 2 to ubiqutinate phospho-ser10-topo I. Such functional fragments can be assessed by assays well known in the art, e.g., and also discussed herein in the Examples.

The term "primer", as used herein, refers to an oligonucleotide which is capable of acting as a point of initiation of polynucleotide synthesis along a complementary strand when placed under conditions in which synthesis of a primer extension product which is complementary to a polynucleotide is catalyzed. Such conditions include the presence of four different nucleotide triphosphates or nucleoside analogs and one or more agents for polymerization such as DNA polymerase and/or reverse transcriptase, in an appropriate buffer ("buffer" includes substituents which are cofactors, or which affect pH, ionic strength, etc.), and at a suitable temperature, A primer must be sufficiently long to prime the synthesis of extension products in the presence of an agent for polymerase. A typical primer contains at least about 5 nucleotides in length of a sequence substantially complementary to the target sequence, but somewhat longer primers are preferred. Usually primers contain about 15-26 nucleotides, but longer primers can also be employed. Oligonucleotides, such as "primer" oligonucleotides are preferably single stranded, but can alternatively be double stranded. If double stranded, the oligonucleotide is generally first treated to separate its strands before being used for hybridization purposes or being used to prepare extension products. Primer oligonucleotides can be oligodeoxyribonucleotide. A primer will always contain a sequence substantially complementary to the target sequence which is the specific sequence to be amplified, to which it can anneal, A primer may, optionally, also comprise a promoter sequence.

In the context of this invention, the term "probe" refers to a molecule which can detectably distinguish between target molecules differing in structure. Detection can be accomplished in a variety of different ways depending on the type of probe used and the type of target molecule, thus, for example, detection can be based on discrimination of activity levels of the target molecule, but preferably is based on detection of specific binding. Examples of such specific binding include antibody binding and nucleic acid probe hybridization. Thus, for example, probes can include enzyme substrates, antibodies and antibody fragments, and preferably nucleic acid hybridization probes, for example DNA, RNA, PNA, pseudo-complementary PNA (pcPNA), locked nucleic acid (LNA) and nucleic acid analogues thereof.

Oligonucleotides can be used as "probes", and refer to such as genomic DNA, mRNA, or other suitable sources of nucleic acid oligonucleotides. For such purposes, the oligonucleotides must be capable of specifically hybridizing to a target polynucleotide or DNA nucleic acid molecule. As used herein, two nucleic acid molecules are said to be capable of specifically hybridizing to one another if the two molecules are capable of forming an anti-parallel, double-stranded nucleic acid structure under hybridizing conditions.

The term "allele-specific oligonucleotide" refers to an oligonucleotide that is able to hybridize to a region of a target polynucleotide spanning the sequence, mutation, or polymorphism being detected and is substantially unable to hybridize to a corresponding region of a target polynucleotide that either does not contain the sequence, mutation, or polymorphism being detected or contains an altered sequence, mutation, or polymorphism. As will be appreciated by those in the art, allele-specific is not meant to denote an absolute condition. Allele-specificity will depend upon a variety of environmental conditions, including salt and formamide concentrations, hybridization and washing conditions and stringency. Depending on the sequences being analyzed, one or more allele-specific oligonucleotides can be employed for each target polynucleotide. Preferably, allele-specific oligonucleotides will be completely complementary to the target polynucleotide. However, departures from complete complementarity are permissible. In order for an oligonucleotide to serve as a primer oligonucleotide, however, it typically need only be sufficiently complementary in sequence to be able to form a stable double-stranded structure under the particular environmental conditions employed. Establishing environmental conditions typically involves selection of solvent and salt concentration, incubation temperatures, and incubation times.

The term "hybridizing" as used herein, refers to the binding of one nucleic acid sequence to another by complementation or complementary base pair matching.

A nucleic acid molecule is said to be the "complement" of another nucleic acid molecule if it exhibits complete complementarity. As used herein, molecules are said to exhibit "complete complementarity" when every nucleotide of one of the molecules is complementary to a nucleotide of the other. Two molecules are said to be "substantially complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described, for example, by Sambrook, J., et al, in Molecular Cloning, a Laboratory Manual, 2nd Edition, Cold Spring Harbor Press, Cold Spring Harbor, N.Y. (1989), and by Haymes, B. D., et al. in Nucleic Acid Hybridization, A Practical Approach, IRL Press, Washington, D.C. (1985), both herein incorporated by reference). Departures from complete complementarity are therefore permissible, as long as such departures do not completely preclude the capacity of the molecules to form a double-stranded structure. For example, a non-complementary nucleotide fragment can be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith for the purposes employed. However, for detection purposes, particularly using labeled sequence-specific probes, the primers typically have exact complementarity to obtain the best results. Thus, for an oligonucleotide to serve as an allele-specific oligonucleotide, it must generally be complementary in sequence and be able to form a stable double-stranded structure with a target polynucleotide under the particular environmental conditions employed.

The term "real-time quantitative RT-PCR" or "quantitative RT-PCR" or "QRT-PCR" are used interchangeably herein, refers to reverse transcription (RT) polymerase chain reaction (PCR) which enables detection of gene transcription. The method is known to those ordinary skilled in the art and comprises of the reverse transcription and amplification of messenger RNA (mRNA) species to cDNA, which is further amplified by the PCR reaction. QRT-PCR enables a one skilled in the art to quantitatively measure the level of gene transcription from the test gene in a particular biological sample. The methods of RNA isolation, RNA reverse transcription (RT) to cDNA (copy DNA) and cDNA or nucleic acid amplification and analysis are routine for one skilled in the art and examples of protocols can be found, for example, in the Molecular Cloning: A Laboratory Manual (3-Volume Set) Ed. Joseph Sambrook, David W. Russel, and Joe Sambrook, Cold Spring Harbor Laboratory; 3rd edition (Jan. 15, 2001), ISBN: 0879695773. Particularly useful protocol source for methods used in PCR amplification is PCR (Basics: From Background to Bench) by M. J. McPherson, S. G. Møller, R. Beynon, C. Howe, Springer Verlag; 1st edition (Oct. 15, 2000), ISBN: 0387916008.

The term "multiplex" as used herein refers to the testing and/or the assessment of more than one gene within the same reaction sample.

The term "amplify" is used in the broad sense to mean creating an amplification product which can include, for example, additional target molecules, or target-like molecules or molecules complementary to the target molecule, which molecules are created by virtue of the presence of the target molecule in the sample. In the situation where the target is a nucleic acid, an amplification product can be made enzymatically with DNA or RNA polymerases or reverse transcriptases. The term "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu, D. Y. et al. (1989) Genomics 4:560-569 (for LCR).

The term "Homology" or "identity" or "similarity" refers to sequence similarity between two peptides or between two nucleic acid molecules. Homology can be determined by comparing a position in each sequence which can be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than about 40% identity, though preferably less than about 25% identity, with one of the sequences of the present invention.

The term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

The term "interact" as used herein is meant to include detectable interactions between molecules, such as can be detected using, for example, e. hybridization assay. The term interact is also meant to include "binding" interactions between molecules. Interactions can be, for example, protein-protein, protein-nucleic acid, protein-small molecule or small molecule-nucleic acid in nature.

The term "isolated" as used herein with respect to nucleic acids, such as DNA or RNA, refers to molecules separated from other DNAs or RNAs, respectively that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to, polypeptides which are isolated from other cellular proteins and is meant to encompass both purified and recombinant polypeptides.

The term "mismatches" refers to hybridized nucleic acid duplexes which are not 100% homologous. The lack of total homology can be due to deletions, insertions, inversions, substitutions or frame shift mutations.

The term "topo I inhibitor" as used herein refers to any entity which mediates some, all or part of its biological function, through acting directly or indirectly on the gene product or polynucleotide of topoisomerase I polypeptide. A topo I inhibitor can directly or indirectly inactivate topo I polypeptide. Exemplarily examples of topo I inhibitor include for example but not limited to, camptothecin (CTP) and analogues thereof including but not limited to irinotecan and topotecan, and derivatives thereof, as these terms are described herein.

The term "CTP" can include a "mimetic" of CPT or a derivative or analogue thereof, which includes compounds which may not be structurally similar to CPT but mimic the therapeutic activity or therapeutic mechanism of CPT or structurally similar CPT compound in vitro and in vivo.

As used herein, the terms "effective" and "effectiveness" or "responsive" or "sensitive" includes both pharmacological effectiveness and physiological safety of an agent, such as a topo I inhibitor. "Pharmacological effectiveness" refers to the ability of the treatment to result in a desired biological effect in the subject. "Physiological safety" refers to the level of toxicity, or other adverse physiological effects at the cellular, organ and/or organism level (often referred to as side-effects) resulting from administration of the treatment, "less effective" means that the treatment results in a therapeutically significant lower level of pharmacological effectiveness and/or a therapeutically greater level of adverse physiological effects.

The term "lack of effectiveness", "non-responsiveness", "refractory" or "unresponsiveness" are used interchangeably herein, and refer to the inability of an agent or treatment to result in a desired biological effect in the subject. Conversely, the term "sensitive" or "responsive" refers to where the desired results is achieved in the subject.

The term "activity" when used in reference to the activity of a protein as used herein, comprises the enzymatic activity, binding affinity and/or posttranslational activity, in particular phosphorylation.

The term "target" as used herein may mean a polynucleotide that may be bound by one or more probes under stringent hybridization conditions.

The term "entity" refers to any structural molecule or combination of molecules.

The term "drug", "agent" or "compound" as used herein refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "agent" refers to any entity which is normally absent or not present at the levels being administered, in the cell. Agent may be selected from a group comprising; chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The term "antagonist" refers to any agent or entity capable of inhibiting the expression or activity of a protein, polypeptide portion thereof, or polynucleotide. Thus, the antagonist may operate to prevent transcription, translation, post-transcriptional or post-translational processing or otherwise inhibit the activity of the protein, polypeptide or polynucleotide in any way, via either direct of indirect action. The antagonist may for example be a nucleic acid, peptide, or any other suitable chemical compound or molecule or any combination of these. Additionally, it will be understood that in indirectly impairing the activity of a protein, polypeptide of polynucleotide, the antagonist may affect the activity of the cellular molecules which may in turn act as regulators or the protein, polypeptide or polynucleotide itself. Similarly, the antagonist may affect the activity of molecules which are themselves subject to the regulation or modulation by the protein, polypeptide of polynucleotide.

The term "protein binding moiety" is used interchangeably herein with "protein binding molecule" or protein binding entity" and refers to any entity which has specific affinity for a protein. The term "protein-binding molecule" also includes antibody-based binding moieties and antibodies and includes immunoglobulin molecules and immunologically active determinants of immunoglobulin molecules, e.g., molecules that contain an antigen binding site which specifically binds (immunoreacts with) to the a BRCA1 protein containing a mutation in the RING and/or BRCT domain which decreases the interaction of BRCA1 with phosphor-ser10-topo I protein. The term "antibody-based binding moiety" is intended to include whole antibodies, e.g., of any isotype (IgG, IgA, IgM, IgE, etc), and includes fragments thereof which are also specifically reactive with the Psap proteins. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody-base binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In a preferred embodiment, the antibody-based binding moiety detectably labeled. In some embodiments, a "protein-binding molecule" is a co-factor or binding protein that interacts with the protein to be measured, for example a co-factor or binding protein to a topo I polypeptide protein.

The term "labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. The detection and quantification of Psap or Tsp-1 present in the tissue samples correlate to the intensity of the signal emitted from the detectably labeled antibody.

The term "specific affinity" or "specifically binds" or "specific binding" are used interchangeably herein refers to an entity such as a protein-binding molecule or antibody that recognizes and binds a desired polypeptide but that does not substantially recognize and bind other molecules in a sample, for example, a biological sample, which naturally includes a polypeptide of the invention, for example phospho-S10 topo I polypeptide.

The term "antibody" is meant to be an immunoglobulin protein that is capable of binding an antigen. Antibody as used herein is meant to include antibody fragments, e.g. F(ab')$_2$, Fab', Fab, capable of binding the antigen or antigenic fragment of interest.

The term "humanized antibody" is used herein to describe complete antibody molecules, i.e. composed of two complete light chains and two complete heavy chains, as well as antibodies consisting only of antibody fragments, e.g. Fab, Fab', F(ab')$_2$, and Fv, wherein the CDRs are derived from a non-human source and the remaining portion of the Ig molecule or fragment thereof is derived from a human antibody, preferably produced from a nucleic acid sequence encoding a human antibody.

The terms "human antibody" and "humanized antibody" are used herein to describe an antibody of which all portions of the antibody molecule are derived from a nucleic acid sequence encoding a human antibody. Such human antibodies are most desirable for use in antibody therapies, as such antibodies would elicit little or no immune response in the human subject.

The term "chimeric antibody" is used herein to describe an antibody molecule as well as antibody fragments, as described above in the definition of the term "humanized antibody." The term "chimeric antibody" encompasses humanized antibodies. Chimeric antibodies have at least one portion of a heavy or light chain amino acid sequence derived from a first mammalian species and another portion of the heavy or light chain amino acid sequence derived from a second, different mammalian species. In some embodiments, a variable region is derived from a non-human mammalian species and the constant region is derived from a human species. Specifically, the chimeric antibody is preferably produced from a 9 nucleotide sequence from a non-human mammal encoding a variable region and a nucleotide sequence from a human encoding a constant region of an antibody.

The term "label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

As used herein the term "reference data" when used in the context of mutations in BRCA1 refers to the sequence of wild type BRCA1 gene or mutations in the BRCA1 gene which do not interfere with, or decrease the BRCA1-phospho-ser10-topo I polypeptide interaction.

The term "support" refers to conventional supports such as beads, particles, dipsticks, fibers, filters, membranes and silane or silicate supports such as glass slides.

The term "cancer", as used herein refers to a cellular proliferative disease in a human or animal subject.

The terms "tumor" or "tumor cell" or "cancer cell" are used interchangeably herein refers to the tissue mass or tissue type or cell type that is undergoing uncontrolled proliferation.

The term "tissue" is intended to include intact cells, blood, blood preparations such as plasma and serum, bones, joints, muscles, smooth muscles, and organs.

The term "Triple-negative subtype" used herein refers to any subtype of cancer, particularly breast cancer, which lacks the expression of the progesterone receptor (PR), lacks the estrogen receptor (ER) and also lacks Her-2 amplification.

As used herein, the term "biological sample" also refers to a cell or population of cells or a quantity of tissue or fluid from a subject. Most often, the sample has been removed from a subject, but the term "biological sample" can also refer to cells or tissue analyzed in vivo, i.e. without removal from the subject. Often, a "biological sample" can contain cells from a subject, but the term can also refer to non-cellular biological material, such as non-cellular fractions of blood, saliva, or urine, that can be used to detect mutations in the BRCA1 gene. As used herein, a "biological sample" or "tissue sample" refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, a biological sample is from a resection, bronchoscopic biopsy, or core needle biopsy of a primary, secondary or metastatic tumor, or a cellblock from pleural fluid. In addition, fine needle aspirate biological samples are also useful. In some embodiments, a biological sample is primary ascite cells. Samples can be fresh, frozen, fixed or optionally paraffin-embedded, frozen or subjected to other tissue preservation methods, including for example methods to preserve the phosphorylation status of polypeptides in the biological sample. A biological sample can also mean a sample of biological tissue or fluid that comprises protein or cells. Such samples include, but are not limited to, tissue isolated from subjects or animals. Biological samples may also include sections of tissues such as biopsy and autopsy samples, frozen sections taken for histological purposes, blood, plasma, serum, sputum, stool, tears, mucus, hair, and skin. Biological samples also include explants and primary and/or transformed cell cultures derived from patient tissues.

A biological sample may be provided by removing a sample of cells from subject, but can also be accomplished by using previously isolated cells (e.g., isolated by another person, at another time, and/or for another purpose), or by performing the methods of the invention in vivo. Archival tissues, such as those having treatment or outcome history may also be used. Biological samples include, but are not limited to, tissue biopsies, scrapes (e.g. buccal scrapes), whole blood, plasma, serum, urine, saliva, cell culture, or cerebrospinal fluid. Biological samples also include tissue biopsies, cell culture. The sample can be obtained by removing a sample of cells from a subject, but can also be accomplished by using previously isolated cells (e.g. isolated by another person), or by performing the methods of the invention in vivo.

The term 'malignancy' and 'cancer' are used interchangeably herein, refers to diseases that are characterized by uncontrolled, abnormal growth of cells. Cancer cells can spread locally or through the bloodstream and lymphatic system to other parts of the body. The term "malignancy" or "cancer" are used interchangeably herein and refers to any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer.

The terms "patient", "subject" and "individual" are used interchangeably herein, and refer to an animal, particularly a human, to whom treatment including prophylaxic treatment is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term "effective amount" includes within its meaning a sufficient amount of a pharmacological composition to provide the desired effect. The exact amount required will vary depending on factors such as the level of phosphorylation (i.e. presence or absence of phosphorylation of topo I, such as phosphorylation of S10 of topo I), the type of tumor to be treated, the severity of the tumor, the drug resistance level of the tumor, the species being treated, the age and general condition of the subject, the particular topo I inhibitor being used as a treatment, the mode of administration and so forth. Thus, it is not possible to specify the exact "effective amount". However, for any given case, an appropriate "effective amount" may be determined by one of ordinary skill in the art using only routine experimentation. As used herein, the effective amount is the amount of an agent or treatment to reduce a symptom of the disease, for example, but not limited to, to reduce the size of a tumor, for example to reduce the size by about 10%, to attenuate the growth rate of the tumor, for example to reduce the rate at which a tumor grows by 10%. For example, an effective amount using the methods as disclosed herein would be considered as the amount sufficient to reduce a symptom of the cancer, for example at least one symptom of a cancer or malignancy by at least 10%. Further, an effective amount as used herein would also include an amount sufficient to prevent or delay the development of a symptom of the disease, alter the course of a symptom disease (for example but not limited to, slow the progression of a symptom of the disease), or reverse a symptom of the disease.

As used herein, the term "treating" includes reducing or alleviating at least one adverse effect or symptom of a condition, disease or disorder associated with cancer. As used herein, the term treating is used to refer to the reduction of a symptom and/or a biochemical marker of cancer, for example a reduction in at least one biochemical marker of cancer by at least 10%. For example but are not limited to, a reduction in a biochemical marker of cancer, for example a reduction in, as an illustrative example only, at least one of the following biomarkers; CD44, telomerase, TGF-α, TGF-β, erbB-2, erbB-3, MUC1, MUC2, CK20, PSA, CA125, FOBT, by 10%, or a reduction in the rate of proliferation of the cancer cells by 10%, would be considered effective treatments by the methods as disclosed herein. As alternative examples, a reduction in a symptom of cancer, for example, a slowing of the rate of growth of the cancer by at least 10% or a cessation of the increase in tumor size, or a reduction in the size of a tumor by at least 10% or a reduction in the tumor spread (i.e. tumor metastasis) by at least 10% would also be considered as affective treatments by the methods as disclosed herein.

The term "polynucleotide" as used herein, refers to single- or double-stranded polymer of deoxyribonucleotide, ribonucleotide bases or known analogies of natural nucleotides, or mixtures thereof. The term includes reference to the specified sequence as well as to the sequence complementary thereto, unless otherwise indicated.

The term "polypeptide" means a polymer made up of amino acids linked together by peptide bonds. The terms "polypeptide" and "protein" are used interchangeably herein, although for the purposes for the present invention, a polypeptide may constitute a portion or the full length protein.

The term "expression" as used herein refers to interchangeably to the expression of a polypeptide or protein and expression of a polynucleotide or gene. Expression of a polynucleotide may be determined, for example, by measuring the production of messenger RNA (mRNA) transcript levels. Expression of a protein or polypeptide may be determined, for example, by immunoassay using an antibody(ies) that bind with the polypeptide.

The term "endogenously expressed" or "endogenous expression" as used herein, refers to the expression of a gene product at normal levels and under normal regulation for that cell type.

In the context of this specification, the term "activity" as it pertains to a protein, polypeptide or polynucleotide means any cellular function, action, effect of influence exerted by the protein, polypeptide or polynucleotide, either by nucleic acid sequence or fragment thereof, or by the protein or polypeptide itself or any fragment thereof.

The term "nucleic acid" or "oligonucleotide" or "polynucleotide" used herein can mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe for a probe that can hybridize to the target sequence under stringent hybridization conditions. Thus, a nucleic acid also encompasses a probe that hybridizes under stringent hybridization conditions.

The term "RNAi" as used herein refers to RNA interference (RNAi) a RNA-based molecule that inhibits gene expression. RNAi refers to a means of selective post-transcriptional gene silencing by destruction of specific mRNA by small interfering RNA molecules (siRNA). The siRNA is typically generated by cleavage of double stranded RNA, where one strand is identical to the message to be inactivated. As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of downstream processing of the RNA (i.e. although siRNAs are believed to have a specific method of in vivo processing resulting in the cleavage of mRNA, such sequences can be incorporated into the vectors in the context of the flanking sequences described herein).

As used herein an "siRNA" refers to a nucleic acid that forms a double stranded RNA, which double stranded RNA has the ability to reduce or inhibit expression of a gene or target gene when the siRNA is present or expressed in the same cell as the target gene, for example where a target gene is for example DNA-PK. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The term "anti-cancer agent" or "anti-cancer drug" as used herein refers to any agent, compound or entity that would be capably of negatively affecting the cancer in the subject, for example killing cancer cells, inducing apoptosis in cancer cells, reducing the growth rate of cancer cells, reducing the number of metastatic cells, reducing tumor size, inhibiting tumor growth, reducing blood supply to a tumor or cancer cells, promoting an immune response against cancer cells or a tumor, preventing or inhibiting the progression of cancer, or increasing the lifespan of the subject with cancer. An anti-cancer therapy encompasses any immunotherapy or biological agent (biotherapy), chemotherapy agents, and radiotherapy agents. The combination of chemotherapy with biological therapy is known in the art as biochemotherapy.

The term "computer" can refer to any apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip.

The term "software" can refer to prescribed rules to operate a computer. Examples of software include: software; code segments; instructions; computer programs; and programmed logic.

The term a "computer system" may refer to a system having a computer, where the computer comprises a computer-readable medium embodying software to operate the computer.

The term "proteomics" may refer to the study of the expression, structure, and function of proteins within cells, including the way they work and interact with each other, providing different information than genomic analysis of gene expression.

The term "statistically significant" or "significantly" refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value.

The term "standard deviation" is a measure of the dispersion of a set of data from its mean. The more spread apart the data, the higher the deviation. Standard deviation is calculated as the square reboot of variance and can be calculated by one of ordinary skill in the art.

Compositions or methods "comprising" one or more recited elements may include other elements not specifically recited. For example, a composition that comprises a fibril component peptide encompasses both the isolated peptide and the peptide as a component of a larger polypeptide sequence. By way of further example, a composition that comprises elements A and B also encompasses a composition consisting of A, B and C. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination." In the context of the specification, the term "comprising" means "including principally, but not necessary solely". Furthermore, variation of the word "comprising", such as "comprise" and "comprises", have correspondingly varied meanings.

The use of the word "a" or "an" when used in conjunction with the term "comprising" in the claims and/or the specification may mean "one" but is also consistent with the meaning of "one or more", "at least one" and "one or more than one."

Other than in the operating examples, or where otherwise indicated, all numbers expressing quantities of ingredients or reaction conditions used herein should be understood as modified in all instances by the term "about." The term "about" when used in connection with percentages can mean±1%.

This invention is further illustrated by the following examples which should not be construed as limiting. The contents of all references cited throughout this application, as well as the figures and tables are incorporated herein by reference.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

BRCA1 Protein Structure

The BRCA1 protein contains the following domains: the RING finger domain (e.g., a Zinc finger, C3HC4 type) and the BRCA1 C Terminus (referred to as the "BRCT") domain. The BRCA1 protein also contains nuclear localization signal and nuclear export signal motifs. The human BRCA1 protein consists of four major protein domains; the RING domain, the BRCA1 serine domain and two BRCT domains. These domains encode approximately 27% of BRCA1 protein. There are six known isoforms of P38398 BRCA1, with isoforms 1 and 2 comprising 1863 amino acids each.

BRCA1 RING Domain

The RING motif, a Zn finger found in eukaryotic peptides, is 40-60 amino acids long and consists of eight conserved metal-binding residues, two quartets of cysteine or histidine residues that coordinate two zinc atoms. This motif contains a short anti-parallel beta-sheet, two zinc binding loops and a central alpha helix in a small domain. This RING domain interacts with associated proteins including BARD1, which also contains a RING motif, to form a heterodimer. The BRCA1 RING motif is flanked by alpha helices formed by residues 8-22 and 81-96 of the BRCA1 protein. It interacts with a homologous region in BARD1 (which also consists of a RING finger flanked by two alpha-helices formed from residues 36-48 and 101-116). These four helices combine to form a heterodimerization interface and stabilise the BRCA1-BARD1 heterodimer complex. Additional stabilisation is achieved by interactions between adjacent residues in the flanking region and hydrophobic interactions. The BARD1/BRCA1 interaction is disrupted by tumorigenic amino acid substitutions in BRCA1 (see: Brzovic P S, et al., (2001). "Structure of a BRCA1-BARD1 heterodimeric RING-RING complex". Nat. Struct. Biol. 8 (10): 833-7, which is incorporated herein in its reference in its entirety)

The RING domain is also an important element of ubiquitin E3 ligases which catalyse protein ubiquitination. Ubiquitin is a small regulatory protein found in all tissues which directs proteins to compartments within the cell. BRCA1 polypeptides, in particular Lys-48-linked polyubiquitin chains, are dispersed throughout within the resting cell nucleus but when DNA synthesis begins they gather in restrained groups that also contain BRCA2 and BARD1. BARD1 is thought to be involved in the recognition and binding of protein targets for ubiquitination. It attaches to proteins and labels them for destruction. Ubiquitination occurs via the BRCA1 fusion protein and is abolished by zinc chelation. The enzyme activity of the fusion protein is dependent on the proper folding of the ring domain.

Serine Cluster Domain

The BRCA1 serine cluster domain (SCD) spans amino acids 1280-1524. A portion of the domain is located in exons 11-13. High rates of mutation occur in exons 11-13. Reported phosphorylation sites of BRCA1 are concentrated in the SCD where they are phosphorylated by ATM/ATR kinases both in vitro and in vivo. ATM/ATR are kinases activated by DNA damage. Mutation of serine residues may affect localization of BRCA1 to sites of DNA damage and DNA damage response function. (see: Clark S L, et al., (2012). "Structure-Function Of The Tumor Suppressor BRCA1". Comput Struct Biotechnol J 1 (1))

BRCT Domains

The dual repeat BRCT domain of the BRCA1 protein is an elongated structure approximately 70 Å long and 30-35 Å wide. The 85-95 amino acid domains in BRCT can be found as single modules or as multiple tandem repeats containing two domains. Both of these possibilities can occur in a single protein in a variety of different conformations. The C-terminal BRCT region of the BRCA1 protein is essential for repair of DNA, transcription regulation and tumor suppressor function. In BRCA1 the dual tandem repeat BRCT domains are arranged in a head-to-tail-fashion in the three-dimensional structure, burying 1600 Å of hydrophobic, solvent accessible surface area in the interface. These all contribute to the tightly packed knob-in-hole structure that comprises the interface. These homologous domains interact to control cellular responses to DNA damage. Missense mutations at the interface of these two proteins can have devastating consequences on the cell cycle, resulting in protein dysfunction and a greater risk of developing cancer. The linker that joins these two homologs need also be considered, as its poorly defined electron density eludes to a possible complex function; the ability to flex.

Mutations in the RING Domain:

Mutations in the RING domain can include any mutations which lead to a decrease in the ubiquitination of the phospho-ser10 topoI protein, and/or decrease the binding affinity of BRCA1 with its binding partner BARD1 and/or an E2 conjugating enzyme (e.g., including but not limited to UbCH5 and UbCH7).

In some embodiments, a relevant mutation in the BRCA1 RING domain is a mutation which decreases the E3 ligase activity of BRCA1 by at least about 10%, or at least about 20%, or at least about 30%, or at least about 40%, or at least about 50%, or at least about 60%, or at least about 70% or more than 70% as compared to the E3 ligase activity of BRCA1 of a wild type BRCA1 gene, and/or decreases the binding affinity of RING domain of BRCA1 with its binding partner BARD1 or an E2 conjugating enzyme (e.g., including but not limited to UbCH5 and UbCH7) by at least about 10%, or at least about 20%, or at least about 30%, or at least about 40%, or at least about 50%, or at least about 60%, or at least about 70% or more than 70% as compared to the binding of the RING domain of a wild type BRCA1 gene (e.g., without the mutation) to BARD1 or the wild type BRCA1 an E2 conjugating enzyme (e.g., including but limited to UbCH5 and UbCH7).

In another embodiment, the mutation in the RING domain causes a decreases in the E3 ligase activity of BRCA1 and/or a decrease in the binding affinity of the RING domain of BRCA1 with its binding partner BARD1 or an E2 conjugating enzyme (e.g., including but limited to UbCH5 and UbCH7) by a statistically significant amount, e.g., at least one standard deviation, more preferably by at least two standard deviations as compared to the wildtype BRCA1 gene.

In some embodiments, a mutation in the RING domain mutations which decreases BRCA1's E3 ligase activity, include, but are not limited to M18, C24R, I26A, C39A, C39Y, C44F/G, C44F, C61A, C61G, C64A, C64Y, T73R, C44F, C47F/G. In some embodiments, a mutation is the RING domain is any mutation of amino acid residues of 18, 24, 26, 39, 44, 61, 64, 73, 44, 47 of BRCA1 of SEQ ID NO: 6.

In some embodiments, a mutation in the RING domain mutations which decreases BRCA1's E3 ligase activity, include, any mutation in a conserved amino acid residue in the RING domain of residues 1-109 of SEQ ID NO:6. Conserved amino acids are well known by persons of ordinary skill in the art and can be assessed by comparing the amino acid sequence of human BRCA1 against the amino acid sequences of the BRCA1 proteins of other species, e.g., mouse, rat, bovine and the like.

Not all mutations in the RING domain of BRCA1 affect BRCA1's ubiquitination E3 ligase Activity. In particular, RING mutations which do not impair E3 ligase activity include, for example, V11A, M18T, I21V, I31M, I42V, R71G (as disclosed in Ruffner et al., PNAS, 2001, 98; 5134-5139).

Mutations in the BRCT Domain:

Mutations in the BRCT domain which can be used in the methods, systems and kits as disclosed herein can include any mutations which lead to a decrease in the binding affinity of the BRCT domain of BRCA1 with phospho-ser10 topoI protein.

In some embodiments, a mutation in the BRCT domain is a mutation which decreases the binding affinity of BRCT domain of BRCA1 with phosphor-ser10-topo I by at least about 10%, or at least about 20%, or at least about 30%, or at least about 40%, or at least about 50%, or at least about 60%, or at least about 70% or more than 70% as compared to the binding affinity of the BRCT1 domain from a wild type BRCA1 protein (e.g., without such a mutation).

In another embodiment, the mutation in the BRCT domain causes a decrease in the binding affinity of BRCT domain with phospho-ser10 topoI by a statistically significant amount, e.g., at least one standard deviation, more preferably by at least two standard deviations as compared to the binding affinity of BRCT domain with phospho-ser10 topoI by the wildtype BRCA1 gene.

In some embodiments, a mutation in the BRCT domain is a mutation which decreases the binding affinity of the BRCT domain of BRCA1 with phosphor-ser10-topo I, includes, but are not limited to G1656D, T1700A, R1699Q, R1699W, M1775R, M1775K, R1835P or E1836K. In some embodiments, a mutation is the BRCT domain is any mutation of amino acids residues 1656, 1700, 1699, 1775, 1835 or 1836 of BRCA1 of SEQ ID NO: 6.

In some embodiments, a mutation in the BRCT domain of BRCA1 which decreases BRCA1's binding affinity to phosphor-ser10-topo I, includes any mutation of a conserved amino acid residue in the BRCT domain of residues 1650-1863 of SEQ ID NO:6. Conserved amino acids are well known by persons of ordinary skill in the art and can be assessed by comparing the amino acid sequence of human BRCA1 against the amino acid sequences of the BRCA1 proteins of other species, e.g., mouse, rat, bovine and the like.

Methods to Identify if a Subject is Responsive to a Topo I Inhibitor

The present invention features diagnostic and prognostic methods, which are based in part, on the identity of mutations or polymorphisms in the BRCA1 gene which results in a decrease in the binding (or binding-affinity) of BRCA1 protein to the phosphor-ser10-topo I protein, and/or decrease the ubiquitination of the phosphor-ser10-topo I protein, thus decrease phosho-ser10-topo I protein degradation. Such information is useful to determine if a subject having the mutation is likely to be responsive to a topo I inhibitor. Accordingly, the methods of the present invention relate to determining the presence of these mutations and/or polymorphisms in BRCA1, and based on the results, it can guide a clinician in recommending a treatment regimen to administer a topo I inhibitor to a subject to treat a cancer if the subject has been identified to have such a BRCA1 mutation that results in a decrease in the binding (or binding-affinity) of BRCA1 gene to phosphor-ser10-topo I, and/or decrease the ubiquitination of the phosphor-ser10-topo I protein, thus decrease phosho-ser10-topo I protein degradation.

In some embodiments, the methods and assays as disclosed herein encompass determining, in a biological sample obtained from a subject, the presence of at least one mutation in the BRCA1 gene which decreases the affinity of the BRCA1 protein for binding to phosphor-ser10-topo I protein, where the subject has, or is at risk for developing a cancer.

In some embodiments, the methods relate to determining the presence or absence of one or more mutations in the BRCA1 gene in a biological sample obtained from a subject, e.g., a mutation in the BRCA1 gene which results in an amino acid change in any one or more of (i) the BRCA1 RING domain, (ii) the BRCT domain of BRCA1, or (iii) the E3 ligase domain of BRCA1 which impairs the E3 ligase activity, where such a mutation results in a decrease in the binding (or binding-affinity) of BRCA1 protein to the phosphor-ser10-topo I protein, and/or decrease the ubiquitination of the phosphor-ser10-topo I protein, thus decrease phosho-ser10-topo I protein degradation. The presence of such a mutation will identify the subject to be responsive (e.g., sensitive) to topo I inhibitors such as camptothecin (CPT), or CPT analogues such as topotecan and irinotecan and derivatives thereof.

Any method to detect a mutation in the BRCA1 gene is encompassed in the methods and assays as disclosed herein, and are well known to one of ordinary skill in the art. In some embodiments, a method to identify a mutation in the BRCA1 gene is disclosed in U.S. Pat. No. 5,747,282 which is incorporated herein in its entirety by reference.

One aspect of the present invention relates to methods and compositions to determine if a topoisomerase I inhibitor is effective in a subject with cancer. One aspect of the present invention relates to a method to determine the presence of one or more mutations in BRCA1 gene, e.g., in the RING domain, and/or BRCT domain and/or a mutation which disrupts E3 ligase activity of BRCA1, wherein the presence of such a mutation indicates that the subject having such cancer will likely be responsive (or sensitive) to a topo I inhibitor as compared to a subject with a cancer who does not have such mutations in the BRCA1 gene. In some embodiments, a mutation in the BRCA1 RING domain between amino acids 1-109 of SEQ ID NO: 6 which interrupt the binding of BRCA1 with topo I protein indicates that the subject carrying the mutation will be responsive to a topo I inhibitor, e.g., CPT or its analogues. In another embodiment, a mutation in the BRCA1 BRCT domain between or inclusive of amino acids 1650-1863 of SEQ ID NO: 6 which interrupts the binding of BRCA1 with the topo I protein indicates that the subject carrying the mutation will be responsive to a topo I inhibitor, e.g., CPT or its analogues. In some embodiments, a mutation between, or inclusive of amino acids 1-109 or 1650-1863 which interrupts the BRCA1 binding with the topo I protein can be assessed by one of ordinary skill in the art using the fluorescence polarization assay as disclosed herein in the Examples.

In some embodiments, a mutation is any change of nucleic acid in BRCA1 gene (e.g., SEQ ID NO: 5) which changes the amino acid cysteine at position 39 (e.g., cystine39) of the BRAC1 protein (SEQ ID NO: 6), or changes the amino acid of the cysteine at position 61 (cystine61) in the RING domain of BRCA1 protein. In some embodiments, any mutation in the BRCA1 gene which results in C39A mutation, or a C64A will identify a subject will likely be responsive to a topo I inhibitor and thus be amenable to treatment with a topo I inhibitor as disclosed herein.

In some embodiments, the mutation is a change of nucleic acid which results in a change of the amino acid arginine at position 1699 (e.g., arginine1699) in the BRCT domain of the BRCA1 protein, for example a nucleic acid change which results in arginine 1699 changing to tryptophan (R1699W). In some embodiments, the mutation is a change of nucleic acid which results in a change of the amino acid glutamic acid at position 1836 (e.g., glutamic acid 1836) in the BRCT domain, for example a change of glutamic acid 1836 to lysine (G1656D). In some embodiments, a mutation in the BRCT domain of BRCA1 which interrupt or decrease the binding of BRCA1 to the topo I protein can be any of the group selected from G1656D, T1700A, R1699Q, R1699W, M1775R, M1775K, R1835P or E1836K. Also encompassed are the 120 distinct missense variations in the BRCT domain which are disclosed in Figge et al., Cancer Epidemiol Biomarkers Prev. 2004 June; 13(6):1037-41. "Missense mutations in the BRCT domain of BRCA-1 from high-risk women frequently perturb strongly hydrophobic amino acids conserved among mammals". Which is incorporated herein in its entirety by reference.

Accordingly, one aspect of the present invention relates to detection in a biological sample from a subject with cancer of at least one mutation in the RING domain and/or BRCT domain of BRCA1 gene which interrupts or decreases the interaction of BRCA1 with the phospho-ser10-topo I protein, where the biological sample is taken from a subject having, or likely having cancer, as a prognostic determinant for drug efficacy with a topo I inhibitor such as CPT and analogues thereof.

Sample nucleic acids for use in the methods as disclosed herein can be obtained from any cell type or tissue, if the sample nucleic acid is genomic DNA. If the sample nucleic acid is mRNA, the sample must be obtained from the cell type or tissue type in which the mRNA is expressed, e.g., in which BRCA1 mRNA is expressed. In some embodiments, a biological sample used to determine the presence of a BRCA1 mutation as disclosed herein is a subject's bodily fluid, (e.g., blood) which can be obtained by known techniques. In alternative embodiments, nucleic acid tests can be performed on dry samples (e.g., hair or skin) etc.

Methods for Detection of Mutations and Variances in BRCA1 Gene

The polynucleotide polymorphisms in the RING domain and/or BRCT domain associated with BRCA1 alleles which decrease the binding affinity of the BRCT domain to phosphor-ser10-topo I can be detected by hybridization with a polynucleotide probe which forms a stable hybrid with that of the target sequence, under stringent to moderately stringent hybridization and wash conditions. If it is expected that the probes will be perfectly complementary to the target sequence, stringent conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. Since such indications identify neutral DNA polymorphisms as well as mutations, these indications need further analysis to demonstrate detection of a BRCA1 susceptibility allele.

Probes for BRCA1 alleles may be derived from the sequences of the BRCA1 region or its cDNAs. The probes may be of any suitable length, which span all or a portion of the BRCA1 region, and which allow specific hybridization to the BRCA1 region. If the target sequence contains a sequence identical to that of the probe, the probes may be short, e.g., in the range of about 8-30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding BRCA1 are preferred as probes. The probes may also be used to determine whether mRNA encoding BRCA1 is present in a cell or tissue.

The polymorphisms of the present invention can be detected directly or indirectly using any of a variety of suitable methods including fluorescent polarization, mass spectroscopy, and the like. Suitable methods comprise direct or indirect sequencing methods, restriction site analysis, hybridization methods, nucleic acid amplification methods, gel migration methods, the use of antibodies that are specific for the proteins encoded by the different alleles of the polymorphism, or by other suitable means. Alternatively, many such methods are well known in the art and are described, for example in T. Maniatis et al., Molecular Cloning, a Laboratory Manual, 2nd Edition, Cold Spring Harbor Press, Cold Spring Harbor, N.Y. (1989), J. W. Zyskind et al., Recombinant DNA Laboratory Manual, Academic Press, Inc., New York (1988), and in R. Elles, Molecular Diagnosis of Genetic Diseases, Humana Press, Totowa, N.J. (1996), and Mamotte et al, 2006, Clin Biochem Rev, 27; 63-75) each herein incorporated by reference.

According to the present invention, any approach that detects mutations or polymorphisms in a gene can be used, including but not limited to single-strand conformational polymorphism (SSCP) analysis (Orita et al. (1989) Proc. Natl. Acad. Sci. USA 86:2766-2770), heteroduplex analysis (Prior et al. (1995) Hum. Mutat. 5:263-268), oligonucleotide ligation (Nickerson et al. (1990) Proc. Natl. Acad. Sci. USA 87:8923-8927) and hybridization assays (Conner et al. (1983) Proc. Natl. Acad. Sci. USA 80:278-282). Traditional Taq polymerase PCR-based strategies, such as PCR-RFLP, allele-specific amplification (ASA) (Ruano and Kidd (1989) Nucleic Acids Res. 17:8392), single-molecule dilution (SMD) (Ruano et al. (1990) Proc. Natl. Acad. Sci. USA 87:6296-6300), and coupled amplification and sequencing (CAS) (Ruano and Kidd (1991) Nucleic Acids Res. 19:6877-6882), are easily performed and highly sensitive methods to determine haplotypes of the present invention (Michalatos-Beloin et al. (1996) Nucleic Acids Res. 24:4841-4843; Barnes (1994) Proc. Natl. Acad. Sci. USA 91:5695-5699; Ruano and Kidd (1991) Nucleic Acids Res. 19:6877-6882).

Restriction Enzyme Analysis

In one embodiment, restriction enzymes can be utilized to identify variances or a polymorphic site using "restriction fragment length polymorphism" (RFLP) analysis (Lentes et al., Nucleic Acids Res. 16:2359 (1988); and C. K. McQuitty et al., Hum. Genet. 93:225 (1994)). In RFLP, at least one target polynucleotide is digested with at least one restriction enzyme and the resulting restriction fragments are separated based on mobility in a gel. Typically, smaller fragments migrate faster than larger fragments. Consequently, a target polynucleotide that contains a particular restriction enzyme recognition site will be digested into two or more smaller fragments, which will migrate faster than a larger fragment lacking the restriction enzyme site. Knowledge of the nucleotide sequence of the target polynucleotide, the nature of the polymorphic site, and knowledge of restriction enzyme recognition sequences guide the design of such assays. In another embodiment of the present invention, restriction site analysis of particular nucleotide sequence by restriction enzymes the identity of a nucleotide at a polymorphic site is determined by the presence or absence of a restriction enzyme site. A large number of restriction enzymes are known in the art and, taken together, they are capable of recognizing at least one allele of many polymorphisms.

Allele-Specific Amplification (ASA).

Allele-specific Amplification is also known as amplification refectory mutation system (ARMS) uses allele specific oligonucleotides (ASO) PCR primers and is an well established and known PCR based method for genotyping (Newton et al, J Med Genet, 1991; 28; 248-51). Typically, one of the two oligonucleotide primers used for the PCR binds to the mutation suite, and amplification only takes place if the nucleotide of the mutation is present, with a mismatch being refractory to amplification. The resulting PCR Products can be analyzed by any means known to persons skilled in the art. In a variation of the approach, termed mutagenically separated PCR (MS-PCR) the two ARMS primer of different lengths, one specific for the normal gene and one for the mutation are used, to yield PCR procures of different lengths for the normal and mutant alleles (Rust et al, Nucl Acids Res, 1993; 21; 3623-9). Subsequent gel electrophoresis, for example will show at least one of the two allelic products, with normal, mutant or both (heterozygote) genes. A further variation of this forms the basis of the Masscode System™ (www.bioserve.com) which uses small molecular weight tags covalently attached through a photo-cleavable linker to the ARMS primers, with each ARMS primers labeled with a tag of differing weight (Kokoris et al, 2000, 5; 329-40). A catalogue of numerous tags allows simultaneous amplification/genotyping (multiplexing) of 24 different targets in a single PCR reaction. For any one mutation, genotyping is based on comparison of the relative abundance of the two relevant mass tags by mass spectrometry.

Ligation Based Assays

A number of approaches use DNA ligase, an enzyme that can join two adjacent oligonucleotides hybridized to a DNA template. In Oligonucleotide ligation assay (OLA) the sequence surrounding the mutation site is first amplified and one strand serves as a template for three ligation probes, two of these are ASO (allele-specific oligonucleotides) and a third common probe. Numerous approaches cane be used for the detection of the ligated products, for example the ASOs with differentially labeled with fluorescent or hapten labels and ligated products detected by fluorogenic of colorimetric enzyme-linked immunosorbent assays (Tobe et al, Nucleic Acid Res, 1996; 24; 3728-32). For electrophoresis-based systems, use of a morbidity modifier taqgs or variation in probe length coupled with fluorescence detection enables the multiplex genotyping of several single nucleotide substitutions in a single tube (Baron et al, 1997; Clinical Chem., 43; 1984-6). When used on arrays, ASOs can be spotted at specific locations or addresses on a chip, PCR amplified DNA can then be added and ligation to labeled oligonucleotides at specific addresses on the array measured (Zhong et al, Proc Natl Acad Sci 2003; 100; 11559-64).

Single-Base Extension

Single base-extension or minisequencing involves annealing an oligonucleotide primer to the single strand of a PCR product and the addition of a single dideoxynucleotide by thermal DNA polymerase. The oligonucleotide is designed to be one base short of the mutation site. The dideoxynucleotide incorporated is complementary to the base at the mutation site. Approaches cans uses different fluorescent tags or haptens for each of the four different dideoxynucleotides (Pastinen et al, Clin Chem 1996, 42; 1391-7). The dideoxynucleotide differ in molecular weight and this is the basis for single-base extension methods utilizing mass-spectrometry, and genotyping based on the mass of the extended oligonucleotide primer, can be used, for example matrix-assisted laser adsorption/ionization time-of flight mass spectrometry or MALDI-TOF (Li et al, Electrophoresis, 1999, 20; 1258-65), which is quantitative and can be used to calculate the relative allele abundance making the approach suitable for other applications such as gene dosage studies (for example for estimation of allele frequencies on pooled DNA samples).

Minisequencing or Microsequencing by MALDI-TOF can be performed by means known by persons skilled in the art. In a variation of the MALDI-TOF technique, some embodiments can use the Sequenom's Mass Array Technology (www.sequenom.com) (Sauser et al, Nucleic Acid Res, 2000, 28; E13 and Sauser et al, Nucleic Acid Res 2000, 28: E100). and also the GOOD Assay (Sauer S et al, Nucleic Acid Res, 2000; 28, E13 and Sauer et al, Nucleic Acid Res, 2000; 28:E100).

In some embodiments, variations of MALDI-TOF can be performed for analysis of variances in the BRCA1 gene. For example, MALDI and electrospray ionization (ESI) (Sauer S. Clin Chem Acta, 2006; 363; 93-105) is also useful with the methods of the present invention.

Hybridization Based Genotyping

Normal or mutant alleles can also be genotypes by measuring the binding of allele-specific oligonucleotides (ASO) hybridization probes. In such embodiments, two ASO probes, one complementary to the normal allele and the other to the mutant allele are hybridized to PCR-amplified DNA spanning the mutation site. In some embodiments, the amplified products can be immobilized on a solid surface and hybridization to radiolabelled oligonucleotides such as known as a 'dot-blot' assay. In alternative embodiments, the binding of the PCR products containing a quantifiable label (eg biotin or fluorescent labels) to a solid phase allele-specific oligonucleotide can be measured. Alternatively, for a reverse hybridixation assay, or "reverse dot-blot" the binding of PCR products containing a quantifiable label (for example but not limited to biotin or fluorescent labels) to a solid phase allele-specific oligonucleotide can be measured. In some embodiments, the use of microarrays comprising hundreds of ASO immobilized onto a sold support surfaces to form an array of ASP can also be used for large scale genotyping of multiple single polymorphisms simultaneously, for example Affymetrix GeneChip® Mapping 10K Array, which can easily be performed by persons skilled in the art.

Homogenous Assays

Homogenous assays, also called "closed tube" arrays, genomic DNA and all the reagents required for the amplification and genotyping are added simultaneously. Genotyping can be achieved without any post-amplification processing. In some embodiments, one such homogenous assay is the 5' fluorogenic nuclease assay, also known as the TaqMan® Assay (Livak et al, Genet Anal, 1999; 14:143-9) and in alternative embodiments Melting curve analyses of FRET probes are used. Such methods are carried out using "real-time" theromcyclers, and utilize two dual-labeled ASO hybridization probes complementary to normal and mutant alleles, where the two probes have different reported labels but a common quencher dye. In such embodiments, the changes in fluorescence characteristics of the probes upon binding to PCR products of target genes during amplification enables "real-time" monitoring of PCR amplification and differences in affinity of the fluorogenic probes for the PCR products of normal and mutant genes enables differentiation of genotypes. The approach uses two dual-labeled ASO hybridization probes complementary to the mutant and normal alleles. The two probes have different fluorescent reported dyes but a common quencher dye. When intact, the probes do not fluoresces due to the proximity of the reporter and quencher dyes. During annealing phase of PCR, two probes compete for hybridization to their target sequences, downstream of the primer sites and are subsequently cleaved by 5' nuclease activity of *Thermophilis aquaticus* (Taq) polymerase as the primer is extended, resulting in the separation of the reporter dyes from the quencher. Genotyping is determined by measurement of the fluorescent intensity of the two reporter dyes after PCR amplification. Thus, when intact the probes do not fluoresce due to the proximity of the quencher dyes, whereas during the annealing phase of the PCR the probes compete for hybridization of the target sequences and the separation of one of the probes from the quencher which can be detected.

Melting-curve analysis of FRET hybridization is another approach useful in the method of the invention. Briefly, the reaction includes two oligonucleotide probes which when in close proximity forms a fluorescent complex, where one probe often termed the "mutant sensor" probe is designed to specifically hybridizes across the mutation site and the other probe (often referred to as the "anchor probe") hybridizes to an adjacent site. Fluorescent light is emitted by the "donor" excites the "acceptor" fluorophore creasing a unique fluorogenic complex, which only forms when the probes bind to adjacent sites on the amplified DNA. The "sensor" probe is complementary to either the normal or the mutant allele. Once PCR is complete, heating of the sample through the melting temperatures of the probe yields a fluorescent temperature curve which differs for the mutant and normal allele.

A variation of the FRET hybridization method is the LCGreen™ method, which obviates the requirement for fluorescent labeled probes altogether. LCGreen™ is a sensitive highly fluorogenic double-stranded DNA (dsDNA) binding dye that is used to detect the dissociation of unlabelled probes (Liew et al, Clin Chem, 2004; 50; 1156-64 and Zhou et al, Clin Chem, 2005; 51; 1761-2). The method uses unlabeled allele-specific oligonucleotides probes that are perfectly complementary either to the mutant or normal allele, and the mismatch of the ASO/template double strand DNA complex results in a lower melting temperature and an earlier reduction in fluorescent signal form the dsDNA binding dye with increasing temperature.

The OLA can also be used for FRET Probes (Chen et al, 1998; 8:549-56), for example, the PCR/ligation mixture can contain PCR primers, DNA polymerase without 5' nuclease activity, thermal stable DNA ligase and oligonucleotides for the ligation reaction. The ligation of the allele-specific oligonucleotides have a different acceptor fluorophore and the third ligation oligonucleotide, which binds adjacently to the ASO has a donor fluorophore, and the three ligation oligonucleotides are designed to have a lower melting temperature for the PCR primers to prevent their interference in the PCR amplification. Following PCR, the temperature is lowered to allow ligation to proceed, which results in FRET between the donor and acceptor dyes, and alleles can be disconcerted by comparing the fluorescence emission of the two dyes.

Alternatives to homogenous PCR- and hybridization-based techniques are also encompassed. For example, molecular beacons (Tyagi et al, Nat Biotech, 1998; 16:49-53) and Scopion® probes (Thelwell et al, Nucleic Acid Res, 2000; 28; 3752-610).

The OLA can also be performed by the use of FRET probes (Chen et al, Genome Res, 1998; 8:549-56). In such an embodiment, the PCR/ligation mix contains PCR primers, a thermostable DNA polymerase without 5' exonuclease activity (to prevent the cleavage of ligation probes during the ligation phase), a thermostable DNA ligase as well as the oligonucleotides for the ligation reaction. The ligation of the ASO each have a different acceptor fluorophore and the third ligation oligonucleotide which binds adjacently to the ASO has a donor fluorophore. The three ligation oligonucleotides are designed to have a lower melting temperature than the annealing temperature for the PCR primers prevent their interference in PCR amplification. Following PCR, the temperature is lowered to allow ligation to proceed. Ligation results in FRET between donor and acceptor dyes, and alleles can be discerned by comparing the fluorescence emission of the two dyes.

Further, variations of the homogenous PCR- and hybridization based techniques to detect polymorphisms are also encompassed in the present invention. For example, the use of Molecular Beacons (Tyagi et al, Nat Biotech 1998; 16; 49-53) and Scorpion® Probes (Thelwell et al, Nucleic Acid Res 2000; 28; 3752-61). Molecular Beacons are comprised of oligonucleotides that have fluorescent reporter and dyes at their 5' and 3' ends, with the central portion of the oligonucleotide hybridizing across the target sequence, but the 5' and 3' flanking regions are complementary to each other. When not hybridized to their target sequence, the 5' and 3' flanking regions hybridize to form a stem-loop structure, and there is little fluorescence because of the proximity of the reported and the quencher dyes. However, upon hybridization to their target sequence, the dyes are separated and there is a large increase in the fluorescence. Mismatched probe-target hybrids dissociate at substantially lower temperatures than exactly matched complementary hybrids. There are a number of variations of the "molecular Beacon" approach. In some embodiments, such a variation includes use of Scorpion® Probes which are similar but incorporate a PCR primer sequence as part of the probe (Thelwell et al, Nucleic Acid Res 2000; 28; 3752-61). In another variation, 'duplex' format gives a better fluorescent signal (Solinas et al, Nucleic Acid Res, 2001, 29; E96).

In another embodiment, polymorphisms can be detected by genotyping using a homogenous or real-time analysis on whole blood samples, without the need for DNA extraction or real-time PCR. Such a method is compatable with FRET and TaqMan™ (Castley et al, Clin Chem, 2005; 51; 2025-30) enabling extremely rapid screening for the particular polymorphism of interest.

Fluorescent Polarization (FP). In FP, the degree to which the emitted light remains polarized in a particular plane is proportional to the speed at which the molecules rotate and tumble in solution. Under constant pressure, temperature and viscosity, FP is directly related to the molecular weight of a fluorescent species. Therefore, when a small fluorescent molecule is incorporated into a larger molecule, there is an increase in FP. FP can be used in for genotyping of polymorphisms of interest (Chen et al, Genome Res, 1999; 9:492-8 and Latif et al, Genome Res, 2001; 11; 436-40). FP can be utilized in 5' nuclease assay (as described above), where the oligonucleotide probe is digested to a lower molecule weight species, for example is amenable to analysis by FP, but with the added benefit of not requiring a quencher. For example, Perlkin-Elmers AcycloPrime™-FP SNP Detection Kit can be used as a FP minisequencing method. Following PCR amplification, unincorporated primers and nucleotides are degraded enzymatically, the enzymes heat inactivated and a miniseqencing reaction using DNA polymerase and fluorescent-labelled dideoxynucleotides performed. FP is then measured, typically in a 96- to 386-well plate format on a FP-plate reader.

Pyrosequencing™. Pyrosequencing™ is a novel and rapid sequencing technique. It is a homogenous methods which is not based on chain termination, does not use dideoxynucleotides, nor does it require electrophoresis (Ahmadian et al, Anal Biochem, 2000, 280:103-10; Alderborn et al, Genome Res, 2000; 10:1249-58; and Ronaghi et al, Anal Biochem, 2000; 286:282-8). The approach is based on the generation of pyrophosphate whenever a deoxynucleotide is incorporated during polymerization of DNA, for example as nucleotides are added to the 3; end of a sequencing primer, or a primer extension: DNAn+dNTP→DNAn+1+pyrophosphate. The generation of pyrophosphate us coupled to a luciferase catalyzed reaction resulting in light emission if the particular deoxynucleotide added is incorporated, yielding a qualitative and distinctive program. Sample processing includes PCR amplification with a biotinylated primer, isolation of the biotinylated single stranded amplicon on streptavidin coated beads (or other solid phase) and annealing of a sequencing primer. Samples are then analyzed by a Pyrosequencer™ (www.pyrosequencing.com) which adds a number of enzymes and substrates required for indicator reaction, including sulfurylase and luciferase, as well as a pyrase for degradation of unincorporated nucleotides. The sample is then interrogated by addition of the four deoxynucleotides. Light emission is detected by a charge coupled device camera (CCD) and is proportional to the number of nucleotides incorporated. Results are automatically assigned by pattern recognition.

Other techniques known to persons skilled in the art are also incorporated for use with the present invention, for example see Kwok, Hum Mut 2002; 9; 315-323 and Kwok, Annu Rev Genomic Hum Genetics, 2001; 2; 235-58 for reviews, which are incorporated herein in their entirety by reference. Examples of other techniques to detect variances and/or polymorphisms are the Invader® Assay (Gut et al, Hum Mutat, 2001; 17:475-92, Shi et al, Clin Chem, 2001, 47, 164-92, and Olivier et al, Mutat Res, 2005; 573:103-110), the method utilizing FLAP endonucleases (U.S. Pat. No. 6,706,476) and the SNPlex genotyping systems (Tobler et al, J. Biomol Tech, 2005; 16; 398-406.

In one embodiment, a long-range PCR (LR-PCR) is used to detect mutations or polymorphisms of the present invention. LR-PCR products are genotyped for mutations or polymorphisms using any genotyping methods known to one skilled in the art, and haplotypes inferred using mathematical approaches (e.g., Clark's algorithm (Clark (1990) Mol. Biol. Evol. 7:111-122).

For example, methods including complementary DNA (cDNA) arrays (Shalon et al., Genome Research 6(7):639-45, 1996; Bernard et al., Nucleic Acids Research 24(8): 1435-42, 1996), solid-phase mini-sequencing technique (U.S. Pat. No. 6,013,431, Suomalainen et al. Mol. Biotechnol. June; 15(2):123-31, 2000), ion-pair high-performance liquid chromatography (Doris et al. J. Chromatogr. A can 8; 806(1):47-60, 1998), and 5' nuclease assay or real-time RT-PCR (Holland et al. Proc Natl Acad Sci USA 88: 7276-7280, 1991), or primer extension methods described in the U.S. Pat. No. 6,355,433, can be used.

In one embodiment, the primer extension reaction and analysis is performed using PYROSEQUENCING™ (Uppsala, Sweden) which essentially is sequencing by synthesis. A sequencing primer, designed directly next to the nucleic acid differing between the disease-causing mutation and the normal allele or the different SNP alleles is first hybridized to a single stranded, PCR amplified DNA template from the individual, and incubated with the enzymes, DNA polymerase, ATP sulfurylase, luciferase and apyrase, and the substrates, adenosine 5' phosphosulfate (APS) and luciferin. One of four deoxynucleotide triphosphates (dNTP), for example, corresponding to the nucleotide present in the mutation or polymorphism, is then added to the reaction. DNA polymerase catalyzes the incorporation of the dNTP into the standard DNA strand. Each incorporation event is accompanied by release of pyrophosphate (PPi) in a quantity equimolar to the amount of incorporated nucleotide. Consequently, ATP sulfurylase converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a PYROGRAM™. Each light signal is proportional to the number of nucleotides incorporated and allows a clear determination of the presence or absence of, for example, the mutation or polymorphism. Thereafter, apyrase, a nucleotide degrading enzyme, continuously degrades unincorporated dNTPs and excess ATP. When degradation is complete, another dNTP is added which corresponds to the dNTP present in for example the selected SNP. Addition of dNTPs is performed one at a time. Deoxyadenosine alfa-thio triphosphate (dATPS) is used as a substitute for the natural deoxyadenosine triphosphate (dATP) since it is efficiently used by the DNA polymerase, but not recognized by the luciferase. For detailed information about reaction conditions for the PYROSEQUENCING, see, e.g. U.S. Pat. No. 6,210,891, which is herein incorporated by reference in its entirety.

Molecular beacons also contain fluorescent and quenching dyes, but FRET only occurs when the quenching dye is directly adjacent to the fluorescent dye. Molecular beacons are designed to adopt a hairpin structure while free in solution, bringing the fluorescent dye and quencher in close proximity. Therefore, for example, two different molecular beacons are designed, one recognizing the mutation or polymorphism and the other the corresponding wildtype allele. When the molecular beacons hybridize to the nucleic acids, the fluorescent dye and quencher are separated, FRET does not occur, and the fluorescent dye emits light upon irradiation Unlike TaqMan probes, molecular beacons are designed to remain intact during the amplification reaction, and must rebind to target in every cycle for signal measurement. TaqMan probes and molecular beacons allow multiple DNA species to be measured in the same sample (multiplex PCR), since fluorescent dyes with different emission spectra can be attached to the different probes, e.g. different dyes are used in making the probes for different disease-causing and SNP alleles. Multiplex PCR also allows internal controls to be co-amplified and permits allele discrimination in single-tube assays. (Ambion Inc, Austin, Tex., TechNotes 8(1)—February 2001, Real-time PCR goes prime time).

Another method to detect mutations or polymorphisms is by using fluorescence tagged dNTP/ddNTPs. In addition to use of the fluorescent label in the solid phase mini-sequencing method, a standard nucleic acid sequencing gel can be used to detect the fluorescent label incorporated into the PCR amplification product. A sequencing primer is designed to anneal next to the base differentiating the disease-causing and normal allele or the selected SNP alleles. A primer extension reaction is performed using chain terminating dideoxyribonucleoside triphosphates (ddNTPs) labeled with a fluorescent dye, one label attached to the ddNTP to be added to the standard nucleic acid and another to the ddNTP to be added to the target nucleic acid.

Alternatively, an INVADER® assay can be used (Third Wave Technologies, Inc (Madison, Wis.)). This assay is generally based upon a structure-specific nuclease activity of a variety of enzymes, which are used to cleave a target-dependent cleavage structure, thereby indicating the presence of specific nucleic acid sequences or specific variations thereof in a sample (see, e.g. U.S. Pat. No. 6,458,535). For example, an INVADER® operating system (OS), provides a method for detecting and quantifying DNA and RNA. The INVADER® OS is based on a "perfect match" enzyme-substrate reaction. The INVADER® OS uses proprietary CLEAVASE® enzymes (Third Wave Technologies, Inc (Madison, Wis.)), which recognize and cut only the specific structure formed during the INVADER® process which structure differs between the different alleles selected for detection, i.e. the disease-causing allele and the normal allele as well as between the different selected SNPs Unlike the PCR-based methods, the INVADER® OS relies on linear amplification of the signal generated by the INVADER® process, rather than on exponential amplification of the target.

In the INVADER® process, two short DNA probes hybridize to the target to form a structure recognized by the CLEAVASE® enzyme. The enzyme then cuts one of the probes to release a short DNA "flap." Each released flap binds to a fluorescently-labeled probe and forms another cleavage structure. When the CLEAVASE® enzyme cuts the labeled probe, the probe emits a detectable fluorescence signal.

Mutations or polymorphisms can also be detected using allele-specific hybridization followed by a MALDI-TOF-MS detection of the different hybridization products. In the preferred embodiment, the detection of the enhanced or amplified nucleic acids representing the different alleles is performed using matrix-assisted laser desorption ionization/time-of-flight (MALDI-TOF) mass spectrometric (MS) analysis described in the Examples below. This method differentiates the alleles based on their different mass and can be applied to analyze the products from the various above-described primer-extension methods or the INVADER® process.

In one embodiment, a haplotyping method useful according to the present invention is a physical separation of alleles by cloning, followed by sequencing. Other methods of haplotyping, useful according to the present invention include, but are not limited to monoallelic mutation analysis (MAMA) (Papadopoulos et al. (1995) Nature Genet. 11:99-102) and carbon nanotube probes (Woolley et al. (2000) Nature Biotech. 18:760-763). U.S. Patent Application No. US 2002/0081598 also discloses a useful haplotyping method which involves the use of PCR amplification.

Computational algorithms such as expectation-maximization (EM), subtraction and PHASE are useful methods for statistical estimation of haplotypes (see, e.g., Clark, A. G. Inference of haplotypes from PCR-amplified samples of diploid populations. Mol Biol Evol 7, 111-22. (1990); Stephens, M., Smith, N.J. & Donnelly, P. A new statistical method for haplotype reconstruction from population data. Am J Hum Genet 68, 978-89. (2001); Templeton, A. R., Sing, C. F., Kessling, A. & Humphries, S. A cladistic analysis of phenotype associations with haplotypes inferred from restriction endonuclease mapping. II. The analysis of natural populations. Genetics 120, 1145-54. (1988)).

Other Assays

Other methods for genetic screening can be used within the scope of the present invention, for example, to detect mutations in genomic DNA, cDNA and/or RNA samples. Methods commonly used, or newly developed or methods yet unknown are encompassed for used in the present invention. Examples of newly discovered methods include for example, but are not limited to; SNP mapping (Davis et al, Methods Mol Biology, 2006; 351; 75-92); Nanogen Nano Chip, (keen-Kim et al, 2006; Expert Rev Mol Diagnostic, 6; 287-294); Rolling circle amplification (RCA) combined with circularable oligonucleotide probes (c-probes) for the detection of nucleic acids (Zhang et al, 2006: 363; 61-70), luminex XMAP system for detecting multiple SNPs in a single reaction vessel (Dunbar S A, Clin Chim Acta, 2006; 363; 71-82; Dunbar et al, Methods Mol Med, 2005; 114: 147-1471) and enzymatic mutation detection methods (Yeung et al, Biotechniques, 2005; 38; 749-758).

Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR (see above), single strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

In such embodiments, protection from cleavage agents (such as a nuclease, hydroxylamine or osmium tetroxide and with piperidine) can be used to detect mismatched bases in RNA/RNA DNA/DNA, or RNA/DNA heteroduplexes (see, e.g., Myers et al. (1985) Science 230:1242). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene of interest with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with 51 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249, Cotton et al. (1988) Proc. Natl. Acad. Sci. USA 85:4397; Saleeba et al. (1992) Methods Enzy. 217:286-295. In another embodiment, the control or sample nucleic acid is labeled for detection.

U.S. Pat. No. 4,946,773 describes an RNaseA mismatch cleavage assay that involves annealing single-stranded DNA or RNA test samples to an RNA probe, and subsequent treatment of the nucleic acid duplexes with RNaseA. For the detection of mismatches, the single-stranded products of the RNaseA treatment, electrophoretically separated according to size, are compared to similarly treated control duplexes. Samples containing smaller fragments (cleavage products) not seen in the control duplex are scored as positive.

Other investigators have described the use of RNaseI in mismatch assays. The use of RNaseI for mismatch detection is described in literature from Promega Biotech. Promega markets a kit containing RNaseI that is reported to cleave three out of four known mismatches.

In other embodiments, alterations in electrophoretic mobility is used to identify the particular allelic variant. For example, single strand conformation polymorphism (SSCP) can be used to detect differences in electrophoretic mobility between mutant and wild type nucleic acids (Orita et al. (1989) Proc Natl. Acad. Sol USA 86:2766; Cotton (1993) Mutat. Res. 285:125-144 and Hayashi (1992) Genet Anal Tech Appl 9:73-79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet. 7:5).

Gel Migration Single strand conformational polymorphism (SSCP; M. Orita et al., Genomics 5:874-879 (1989); Huinphfies et al., In: Molecular Diagnosis of Genetic Diseases, R. Elles, ed. pp 321-340 (1996)) and temperature gradient gel electrophoresis (TGGE; R. M. Wartell et al., Nucl. Acids Res. 18:2699-2706 (1990)) are examples of suitable gel migration-based methods for determining the identity of a polymorphic site. In SSCP, a single strand of DNA will adopt a conformation that is uniquely dependent of its sequence composition. This conformation is usually different, if even a single base is changed. Thus, certain embodiments of the present invention, SSCP can be utilized to identify polymorphic sites, as wherein amplified products (or restriction fragments thereof of the target polynucleotide are denatured, then run on a non-denaturing gel. Alterations in the mobility of the resultant products are thus indicative of a base change. Suitable controls and knowledge of the "normal" migration patterns of the wild-type alleles can be used to identify polymorphic variants.

In yet another embodiment, the identity of the allelic variant is obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to insure that it does not completely denature, for, example by adding a GC clamp of approximately 40 bp of high-melting GC rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Others have described using the MutS protein or other DNA-repair enzymes for detection of single-base mismatches. Alternative methods for detection of deletion, insertion or substitution mutations that can be used in the practice of the present invention are disclosed in U.S. Pat. Nos. 5,849,483, 5,851,770, 5,866,337, 5,925,525 and 5,928,870, each of which is incorporated herein by reference in its entirety.

Further Examples of SNP Screening Methods

Spontaneous mutations that arise during the course of evolution in the genomes of organisms are often not immediately transmitted throughout all of the members of the species, thereby creating polymorphic alleles that co-exist in the species populations. Often polymorphisms are the cause of genetic diseases. Several classes of polymorphisms have been identified. For example, variable nucleotide type polymorphisms (VNTRs), arise from spontaneous tandem duplications of di- or trinucleotide repeated motifs of nucleotides. If such variations alter the lengths of DNA fragments generated by restriction endonuclease cleavage, the variations are referred to as restriction fragment length polymorphisms (RFLPs). RFLPs are widely used in human and animal genetic analyses.

In one embodiment, restriction enzymes can be utilized in identifying a polymorphic site in "restriction fragment length polymorphism" (RFLP) analysis (Lentes et al., Nucleic Acids Res. 16:2359 (1988); and C. K. McQuitty et al., Hum. Genet. 93:225 (1994)). In RFLP, at least one target polynucleotide is digested with at least one restriction enzyme and the resultant "restriction fragments" are separated based on mobility in a gel. Typically, smaller fragments migrate faster than larger fragments. Consequently, a target polynucleotide that contains a particular restriction enzyme recognition site will be digested into two or more smaller fragments, which will migrate faster than a larger fragment lacking the restriction enzyme site. Knowledge of the nucleotide sequence of the target polynucleotide, the nature of the polymorphic site, and knowledge of restriction enzyme recognition sequences guide the design of such assays. In another embodiment of the present invention, restriction site analysis of particular nucleotide sequence by restriction enzymes the identity of a nucleotide at a polymorphic site is determined by the presence or absence of a restriction enzyme site. A large number of restriction enzymes are known in the art and, taken together, they are capable of recognizing at least one allele of many polymorphisms.

However, such single nucleotide polymorphisms (SNPs) rarely result in changes in a restriction endonuclease site. Thus, SNPs are rarely detectable by restriction fragment length analysis. SNPs are the most common genetic variations and occur once every 100 to 300 bases and several SNP mutations have been found that affect a single nucleotide in a protein-encoding gene in a manner sufficient to actually cause a genetic disease. SNP diseases are exemplified by hemophilia, sickle-cell anemia, hereditary hemochromatosis, late-onset Alzheimer's disease etc.

In context of the present invention, polymorphic mutations that affect the activity and/or levels of the BRCA1 gene products will be determined by a series of screening methods. In important embodiments of the present invention uses screening methods aimed at identifying SNPs that affect the inducibility, activity and/or level of the BRCA1 gene products in in vitro or in vivo assays. The other set of screening methods will then be performed to screen an individual for the occurrence of the SNPs identified above. To do this, a sample (such as blood or other bodily fluid or tissue sample) will be taken from a subject for genotype analysis.

SNPs can be the result of deletions, point mutations and insertions. In general any single base alteration, whatever the cause, can result in a SNP. The greater frequency of SNPs means that they can be more readily identified than the other classes of polymorphisms. The greater uniformity of their distribution permits the identification of SNPs "nearer" to a particular Gait of interest. The combined effect of these two attributes makes SNPs extremely valuable. For example, if a particular Gait (e.g., increased level of BRCA1 RNA) reflects a mutation at a particular locus, then any polymorphism that is linked to the particular locus can be used to predict the probability that an individual will be exhibit that Wait. In some cases, the SNP can be the cause of the Gait.

Several methods have been developed to screen polymorphisms and some examples are listed below. The reference of Kwok and Chen (2003) and Kwok (2001) provide overviews of some of these methods, both of these references are specifically incorporated by reference.

Examples of identifying polymorphisms and applying that information in a way that yields useful information regarding patients can be found, for example, in U.S. Pat. No. 6,472,157; U.S. Patent Application Publications 20020016293, 20030099960, 20040203034; WO 0180896, all of which are hereby incorporated by reference.

Linkage Disequilibrium

Polymorphisms or mutations in the BRCA1 gene can be identified using linkage disequilibrium. "Linkage disequilibrium" ("LD" as used herein, though also referred to as "LED" in the art) refers to a situation where a particular combination; of alleles (i.e., a variant form of a given gene) or polymorphisms at two loci appears more frequently than would be expected by chance. "Significant" as used in respect to linkage disequilibrium, as determined by one of skill in the art, is contemplated to be a statistical p or o value that can be 0.25 or 0.1 and can be 0.1, 0.05. 0.001, 0.00001 or less. The relationship between BRCA1 haplotypes and the expression level of the BRCA1 proteins can be used to correlate the genotype (i.e., the genetic make up of an organism) to a phenotype (i.e., the physical traits displayed by an organism or cell). "Haplotype" is used according to its plain and ordinary meaning to one skilled in the art. It refers to a collective genotype of two or more alleles or polymorphisms along one of the homologous chromosomes.

SNPs relating to the expression of BRCA1 function can be characterized by the use of any of these methods or suitable modification thereof. Such methods include the direct or indirect sequencing of the site, the use of restriction enzymes where the respective alleles of the site create or destroy a restriction site, or the use of allele-specific hybridization probes.

The term "allele-specific PCR" refers to PCR techniques where the primer pairs are chosen such that amplification is dependent upon the input template nucleic acid containing the polymorphism of interest. In such embodiments, primer pairs are chosen such that at least one primer is an allele-specific oligonucleotide primer. In some sub-embodiments of the present invention, allele-specific primers are chosen so that amplification creates a restriction site, facilitating identification of a polymorphic site. In other embodiments of the present invention, amplification of the target polynucleotide is by multiplex PCR (Wallace et al. (PCT Application WO89/10414)). Through the use of multiplex PCR, a multiplicity of regions of a target polynucleotide can be amplified simultaneously. This is particularly advantageous in embodiments where more than one SNP is to be detected.

If the polymorphic region is located in the coding region of the gene of interest, yet other methods than those described above can be used for determining the identity of the allelic variant. For example, identification of the allelic variant, which encodes a mutated signal peptide, can be performed by using an antibody specifically recognizing the mutant protein in, e.g., immunohistochemistry or immunoprecipitation. Antibodies to the wild-type or signal peptide mutated forms of the signal peptide proteins can be prepared according to methods known in the art.

In another embodiment, multiplex PCR procedures using allele-specific primers can be used to simultaneously amplify multiple regions of a target nucleic acid (PCT Application WO89/10414), enabling amplification only if a particular allele is present in a sample. Other embodiments using alternative primer-guided nucleotide incorporation procedures for assaying polymorphic sites in DNA can be used, and have been described (Komher, J. S. et al., Nucl. Acids. Res. 17:7779-7784 (1989); Sokolov, B. P., Nucl. Acids Res. 18:3671 (1990); Syvanen, A. C., et al., Genomics 8:684-692 (1990); Kuppuswamy, M. N. et al., Proc. Nad. Acad. Sci. (U.S.A) 88:1143-1147 (1991); Bajaj et al. (U.S. Pat. No. 5,846,710); Prezant, T. R. et al., Hum Mutat. 1: 159-164 (1992); Ugozzoli, L. et al., GATA 9:107-112 47 (1992); Nyr6n, P. et al., Anal. Biochem. 208:171-175 (1993)).

Other known nucleic acid amplification procedures include transcription-based amplification systems (Malek, L. T. et al., U.S. Pat. No. 5,130,238; Davey, C. et al., European Patent Application 329,822; Schuster et al.) U.S. Pat. No. 5,169,766; Miller, H. I. et al., PCT-Application WO89/06700; Kwoh, D. et al., Proc. Natl. Acad Sci. (U.S.A) 86:1173 Z1989); Gingeras, T. R. et al., PCT Application WO88/10315)), or isothermal amplification methods (Walker, G. T. et al., Proc. Natl. 4cad Sci. (U.S.A) 89:392-396 (1992)) can also be used.

Solid Supports

Solid supports containing oligonucleotide probes for identifying the alleles, including polymorphic alleles, of the present invention can be filters, polyvinyl chloride dishes, silicon or glass based chips, etc. Such wafers and hybridization methods are widely available, for example, those disclosed by Beattie (WO 95/11755). Any solid surface to which oligonucleotides can be bound, either directly or indirectly, either covalently or noncovalently, can be used. A preferred solid support is a high density array or DNA chip. These contain a particular oligonucleotide probe in a predetermined location on the array. Each predetermined location can contain more than one molecule of the probe, but each molecule within the predetermined location has an identical sequence. Such predetermined locations are termed features. There can be, for example, about 2, 10, 100, 1000 to 10,000; 100,000, 400,000 or 1,000,000 of such features on a single solid support. The solid support, or the area within which the probes are attached can be on the order of a square centimeter.

Oligonucleotide probe arrays can be made and used according to any techniques known in the art (see for example, Lockchart et al. (1996), Nat. Biotechnol. 14: 1675-1680; McGall et al. (1996), Proc. Nat. Acad. Sci. USA 93: 13555-13460). Such probe arrays can contain at least two or more oligonucleotides that are complementary to or hybridize to two or more of the SNPs described herein.

Databases

The present invention includes databases containing information concerning polymorphic alleles associated with mutations in BRCA1, and/or mutations in the RING domain and/or BRCT domain in BRCA1, e.g., that decrease the binding of BRCA1 to phospho-ser10-topoI and/or decrease ubiquitination of phospho-ser10-topoI and the like. Databases can also contain information associated with a given polymorphism such as descriptive information about the probability of association of the polymorphism with prediction of clinical phenotype, for example the likelihood of responsiveness to a topo I inhibitor as described herein. Other information that can be included in the databases of the present invention include, but is not limited to, SNP sequence information, descriptive information concerning the clinical status of a tissue sample analyzed for SNP haplotype, or the subject from which the sample was derived. The database can be designed to include different parts, for instance a SNP frequency database and a SNP sequence database. Methods for the configuration and construction of databases are widely available, for instance, see Akerblom et al., (1999) U.S. Pat. No. 5,953,727, which is herein incorporated by reference in its entirety.

The databases of the present invention can be linked to an outside or external database. In a preferred embodiment, the external database can be the HGBASE database maintained by the Karolinska Institute, The SNP Consortium (TSC)

and/or the databases maintained by the National Center for Biotechnology Information (NCBI) such as GenBank.

The databases of the present invention can also be used to present information identifying the polymorphic alleles in a subject and such a presentation can be used to predict the likelihood that the subject will be responsive to a topo I inhibitor as disclosed herein. Further, the databases of the present invention can comprise information relating to the expression level of one or more of the genes associated with the polymorphic alleles of the invention.

The detection of the mutations can be performed in situ directly on tissue samples or tissue sections (fixed or frozen) obtained from a subject, e.g., biopsy samples, such that no nucleic acid purification is necessary. Nucleic acid reagents can be used as probes and/or primers for in situ procedures (e.g., see Nuovo, 1992 "PCR In Situ Hybridization: Protocols and Applications. Raven Press, NY).

Method and Assays for Identifying Mutations the BRCA1 Gene which Decrease the BRCA1 Protein Binding with Phosphor-Ser10-Topo I Protein.

There have been over 1600 mutations discovered within the BRCA1 gene (collated in the Breast cancer Information Core Database (BIC); world-wide web at: research.nhgri.nih.gov/projects/bic). 570 distinct missense mutations or variations have been detected throughout the 1860 codons of BRCA1, but less than 2% of these have been conclusively associated with cancer. Here, the inventors provide a method to identify mutations in the BRCA1 gene, in particular in the RING domain and/or BRCT domain which decrease the binding affinity of the BRCA1 protein for the phospho-ser10-topoI and/or decrease ubiquitination of phospho-ser10-topo I.

Accordingly, another aspect of the present invention relates to an assay for identifying mutations in the BRCT domain and/or RING domain of the BRCA1 gene which interfere (e.g., decrease the binding affinity) of the BRCA1 protein binding with the phosphor-ser10-topo I protein and/or result in decreased ubiquitination of the phosphor-ser10-topo I protein by at least about 10% as compared to a wild type BRCA1 protein not comprising such mutations.

In some embodiments, the assay as disclosed herein is a fluorescent polarization assay, where a fluorescent phosphopeptide of topo I (e.g., SEQ ID NO: 1 or SEQ ID NO:4) is incubated with a BRCT domain or fragment thereof which comprises the mutation, and the binding affinity of the BRCT domain with the mutation of interest is evaluated in comparison with the binding affinity of the wild-type BRCT domain. In some embodiments the binding affinity of different protein concentrations of the BRCT domain (e.g., from 20 nM to 500 microM) is evaluated with a constant concentration of the topo I phosphopeptide (e.g., 1:1000, or 1:500, or 50 nM or 100 nM) in a reaction volume of 20 microliters. The fluorescence is recorded and a polarization change is plotted against the log of a protein concentration, and a Kd determined from the resulting curve. A mutation in the BRCT domain which decreases the fluorescence as compared to the fluorescence measured with the wild-type BRCT domain identifies a mutation in the BRCT domain which interferes with the BRCA1 protein interaction with the phosphor-ser10-topo I protein.

Another aspect of the present invention relates to methods, assays and kits to identify mutations in the RING and/or BRCT domain of BRCA1 which interrupt the binding of BRCA1 protein to the phospho-topo I protein, e.g., phosphor-ser10-topo I protein. In some embodiments, a mutation in the BRCT domain of BRCA1 which interrupts the binding of BRCA1 protein to the phospho-topo I protein, are mutations which decrease the binding affinity of the BRCA1 protein for the phosphorylated ser10 topo I protein. As disclosed herein, one such assay is a fluorescent polarization (FP) assay, comprising a BRCT domain comprising a mutation of interest, and a topo I phosphopeptide, e.g., such as SEQ ID NO: 4. In some embodiments, the BRCT domain of BRCA1 (e.g., amino acids 1650-1863 of SEQ ID NO: 6 or a functional fragment thereof) is conjugated to a GST or other molecule.

In some embodiments, the binding affinity or interaction of a BRCT domain harboring a mutation with the topo I phosphopeptide is assessed and compared with the binding affinity or interaction of a wild type BRCT domain with the topo I phosphopeptide to determine if the mutation in the BRCT domain decreases (e.g., interferes) the binding affinity of the BRCT domain with the topo I phosphopeptide by at least 10%, or at least about 20% or at least about 30% or at least about 40% as compared to a BRCT domain without such a mutation. Detection of a decrease of binding affinity will indicate that the mutation interferes with the BRCT-phospho-S10 topo I polypeptide interaction, and that a subject having such a mutation will be responsive to treatment with a topo I inhibitor, e.g., CPT or analogues or derivatives thereof.

In another embodiment, a similar fluorescent polarization (FP) assay can be performed, comprising the RING domain of BRCA1 comprising a mutation of interest, and a topo I phosphopeptide, e.g., such as SEQ ID NO: 4 or SEQ ID NO:1. In some embodiments, the RING domain of BRCA1 (e.g., amino acids 1-109 of SEQ ID NO: 6 or a functional fragment thereof) is conjugated to a GST or other molecule.

In some embodiments, the binding affinity or interaction of a RING domain that comprises a mutation with the topo I phosphopeptide is assessed and compared with the binding affinity or interaction of a wild type RING domain (e.g., without a mutation), and where a mutation in the RING domain which decreases (e.g., interferes) the binding affinity of the RING domain with the topo I phosphopeptide, and/or decreases ubiquitination of the topo I phosphopeptide by at least about 10% or at least about 20%, or at least about 30% or at least about 40% as compared to the binding affinity and/or ubiquitination by a RING domain without such a mutation, indicates that the subject having such a mutation will be responsive to a topo I inhibitor. Detection of a decrease of binding affinity, and/or a decrease in ubiquitination of the phosphopeptide will indicate that the mutation interferes with the ubiquitination E3 ligase function of BRCA1 and/or the BRCA1-phospho-S10 topo I polypeptide interaction, and/or the BRCA1/BARD1 interaction, and thus ubiquitination of phospho-S10-topo I protein. A subject that has such a mutation will be identified as being likely to be responsive to treatment with topo I inhibitors, e.g., CPT or analogues or derivatives thereof.

Methods and assays for identifying agents which interfere with the BRCA1-phospho-ser10-topo I protein interaction.

Another aspect of the present invention relates to methods, assays and kits for high-throughput screening (HTS) of candidate molecules to identify compounds which interfere with the BRCA1-phospho-ser10 topo I polypeptide interaction, In some embodiments, an assay comprises a topo I polypeptide or a functional fragment thereof, which is phosphorylated on serine 10 (S10) by DNA-PK kinase, then incubated with a ubiquitin mixture comprising a BRCT domain of BRCA1, or a functional fragment thereof, pre-incubated with at least one test compound. In some embodiments, a decrease in fluorescence in such an assay as compared to a negative control or absence of a test compound indicates that the test compound decreases the interaction of BRCT domain with the phosphor-S10-topo I protein. Such a compound is thus useful to be used in conjunction or in combination with a topo I inhibitor, e.g., CPT or analogues thereof to increase the efficacy of the topo I inhibitor in the treatment of cancer.

Another aspect of the present invention relates to a method to treat cancer in a subject, the method comprising assessing a biological sample from the subject with cancer for the presence of mutations in the RING domain and/or BRCT domain and/or E3 ligase domain of the BRCA1 gene; and if a mutation is detected which decreases the binding of BRCA1 to the phospho-S10-topo I polypeptide by at least 10%, and/or decreases the ubiquitination of phosphor-ser10-topo I protein by about 10% as compared to a wild-type BRCA1 (e.g., without a mutation), the cancer is identified as being responsive to a topoisomerase I inhibitor. In one embodiment, the biological sample taken from a subject can be tested using the methods, kits, machines and computer systems and computer readable media as described herein.

The inventors previously generated anti-phosho-ser10-topo I antibodies using an antigenic polypeptide MSGDHLHND(pS)QIEADFR (SEQ ID NO: 1) or ND(pS)QIEADFRLNDC (SEQ ID NO: 4), where the serine is phosphorylated (pS). In some embodiments, the phospho-ser10-topo I peptides useful in assays and methods for identifying compounds which interrupt, e.g., decrease the binding (or binding affinity) of the BRCA1 protein with the phosho-ser10-topo I protein include, but are not limited to, the phosphopeptides of SEQ ID NO: 1 and 2.

Agents or compounds identified using the HTS as disclosed herein can be used in combination with topo I inhibitors as disclosed herein, e.g., at the same time, prior to, after administration of a topo I inhibitor. e.g., function as "topo I inhibitor sensitivity agent" as disclosed herein.

Methods to Identify a Cancer Unresponsive to a Topo I Inhibitor

In another embodiment, the methods, kits, machines, computer systems and computer readable media as disclosed herein can be used to determine if a cancer in a subject is responsive to a topo I inhibitor such as CPT or analogues thereof, where the methods, kits, machines, computer systems or computer readable media assess a biological sample from a subject with cancer, and if a biological sample is determined to a mutation in the RING domain and/or BRCT domain of the BRCA1 protein which decreases the binding affinity of the BRCA1 protein for phospho-S10-topo I protein, and/or decreases the ubiquitination of the for phospho-S10-topo I protein by at least about 10% as compared to the binding affinity and/or ubiquitination of a wild type BRCA1 protein (e.g., without a mutation), it identifies a subject having or likely having a cancer which is responsive to a topo I inhibitor, such as CPT and derivatives and analogues thereof.

In some embodiments of this aspect and all aspect described herein, the presence a mutation in the RING domain and/or BRCT domain of the BRCA1 protein which decreases the binding affinity of the BRCA1 protein for phospho-S10-topo I protein, and/or decreases the ubiquitination of the for phospho-S10-topo I protein can be determined by a machine, computer system or computer readable media as described herein, wherein the presence a mutation in the RING domain and/or BRCT domain of the BRCA1 protein which decreases the binding affinity of the BRCA1 protein for phospho-S10-topo I protein, and/or decreases the ubiquitination of the for phospho-S10-topo I protein is determined by a determination module, followed by comparative analysis with a reference sample comparison with stored data, for instance in stored reference data in a comparison module and displaying the retrieved data with a display module method.

The term "biological sample" is intended to include tissues, cells and biological fluids isolated from a subject, as well as tissues, cells and fluids present within a subject. In some embodiments, the methods as disclosed herein provide for the detection of the presence or absence of a mutation can be performed using commonly known methods of ordinary skill in the art, which include for example but are not limited to; but not limited to, mass spectrometry systems including Matrix Assisted Laser Desorption Ionization—Time of Flight (MALDI-TOF) systems and SELDI-TOF-MS ProteinChip array profiling systems; systems for analyzing gene expression data (see, for example, published U.S. Patent Application, Pub. No. U.S. 2003/0194711, which is incorporated herein in its entirety by reference); systems for array based expression analysis: e.g., HT array systems and cartridge array systems such as GENECHIP® AUTOLOADER, COMPLETE GENECHIP® Instrument System, GENECHIP® Fluidics Station 450, GENECHIP® Hybridization Oven 645, GENECHIP® QC Toolbox Software Kit, GENECHIP® Scanner 3000 7G plus Targeted Genotyping System, GENECHIP® Scanner 3000 7G Whole-Genome Association System, GENETITAN™ Instrument, and GENECHIP® Array Station (each available from Affymetrix, Santa Clara, Calif.); automated ELISA systems (e.g., DSX® or DS2® (available from Dynax, Chantilly, Va.) or the TRITURUS® (available from Grifols USA, Los Angeles, Calif.), The MAGO® Plus (available from Diamedix Corporation, Miami, Fla.); Densitometers (e.g. X-Rite-508-SPECTRO DENSITOMETER® (available from RP IMAGING™, Tucson, Ariz.), The HYRYS™ 2 HIT densitometer (available from Sebia Electrophoresis, Norcross, Ga.); automated Fluorescence insitu hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACSVantage SE, (available from Becton Dickinson, Franklin Lakes, N.J.); and radio isotope analyzers (e.g. scintillation counters).

In some embodiments, the sequence of the RING domain and/or BRCT domain of the BRCA1n gene is compared against a reference sequence for the BRCA1 gene, e.g. the wild-type BRCA1 gene of SEQ ID NO: 5 using the methods, kits, machines, computer systems and computer readable media as disclosed herein.

In some embodiments, the methods as disclosed herein provide a diagnostic test for the activity of topo I inhibitors in the treatment of cancer, i.e. efficacy of a topo I inhibitor such as CPT to reduce cell viability. In one embodiment, a diagnostic test useful in the methods as disclosed herein can detect the presence of one or more mutations in the RING domain and/or BRCT domain of the BRCA1 protein which decreases the binding affinity of the BRCA1 protein for phospho-S10-topo I protein, and/or decreases the ubiquitination of the for phospho-S10-topo I protein by at least about 10% as compared to the binding affinity and/or ubiquitination of a wild type BRCA1 protein (e.g., without a mutation), which indicates that a topo I inhibitor is likely to be effective in the treatment of cancer in a subject when compared to a subject whom does not have the same mutation. Thus, in some embodiments, detection of a mutation in the RING domain and/or BRCT domain of the BRCA1 protein which decreases the binding affinity of the BRCA1 protein for phospho-S10-topo I protein, and/or decreases the ubiquitination of the for phospho-S10-topo I protein in a biological sample from a subject can be used as a diagnostic to identify cancers which are likely to be responsive to a topo I inhibitor treatment. In related embodiments, the comparison of the sequence of the RING domain and/or BRCT domain of the BRCA1 protein can be determined between treated and untreated biopsy samples, cell lines, transgenic animals, or extracts from any of these, to determine the effect of a given treatment topo I inhibitor as compared to an untreated control.

Automated Methods to Determine of the Phosphorylation Status of Topo I Using Machines, Computer Systems and Computer Readable Media.

In all aspects of the invention, methods to determine a mutation in the RING domain and/or BRCT domain of the BRCA1 protein which decreases the binding affinity of the BRCA1 protein for phospho-S10-topo I protein, and/or decreases the ubiquitination of the phospho-S10-topo I protein can be performed using an automated machine or system. Such machines and systems generate a report, such as displaying a report on a visible screen or a printable report which indicates the presence of a mutation in the RING domain and/or BRCT domain of the BRCA1 protein which decreases the binding affinity of the BRCA1 protein for phospho-S10-topo I protein, and/or decreases the ubiquitination of phospho-S10-topo I protein by at least about 10% as compared to a wild type BRCA1 (e.g., without such a mutation). In some embodiments, the report also indicates if the biological sample, or the subject from which the biological sample is obtained, is likely to be responsive to a topo I inhibitor respectively.

Accordingly, some embodiments of the invention also provide for a machine, computer systems and computer readable media for performing the steps of (i) determining the presence of a mutation in the RING domain and/or BRCT domain of the BRCA1 protein which decreases the binding affinity of the BRCA1 protein for phospho-S10-topo I protein, and/or decreases the ubiquitination of the for phospho-S10-topo I protein (ii) indicating or reporting whether a subject has a likelihood of being responsive to a topo I inhibitor, and thus provides a prognostic indicator if a topo I inhibitor is likely to be effective the treatment of cancer in the subject.

Embodiments of this aspect of the present invention are described through functional modules, which are defined by computer executable instructions recorded on computer readable media and which cause a computer to perform method steps when executed. The modules have been segregated by function for the sake of clarity. However, it should be understood that the modules need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

Computer Systems:

One aspect of the present invention is a computer system that can be used to determine if a subject is responsive to a topo I inhibitor. In such an embodiment, a computer system is connected to a determination module and is configured to obtain output data from a determination module regarding a biological specimen, where a determination module is configured to detect the sequence information of the BRCA1 gene and/or the presence of a mutation in the RING domain and/or BRCT domain of the BRCA1 protein which decreases the binding affinity of the BRCA1 protein for phospho-S10-topo I protein, and/or decreases the ubiquitination of the for phospho-S10-topo I protein from biological sample obtained from the subject; and where the computer system comprises (a) a storage device configured to store data output from the determination module as well as reference data; where the storage device is connected to (b) a comparison module which in one embodiment, is adapted to compare the output data stored on the storage device with stored reference data, and in alternative embodiments, adapted to compare the output data with itself, where the comparison module produces report data and is connected to (c) a display module for displaying a page of retrieved content (i.e. report data from the comparison module) for the user on a client computer, wherein the retrieved content can indicate the presence or absence of a mutation in the RING domain and/or BRCT domain of the BRCA1 protein which decreases the binding affinity of the BRCA1 protein for phospho-S10-topo I protein, and/or decreases the ubiquitination of the for phospho-S10-topo I protein.

As used herein, "sequence information" refers to any nucleotide and/or amino acid sequence, including but not limited to full-length nucleotide and/or amino acid sequences, partial nucleotide and/or amino acid sequences, or mutated sequences. Moreover, information "related to" the sequence information includes detection of the presence or absence of a sequence (e.g., detection of a mutation or deletion), determination of the concentration of a sequence in the sample (e.g. amino acid sequence expression levels, or nucleotide (RNA or DNA) expression levels), and the like.

As an example, determination modules for determining the sequence information or presence of absence of a mutation in the RING domain and/or BRCT domain of the BRCA1 protein which decreases the binding affinity of the BRCA1 protein for phospho-S10-topo I protein, and/or decreases the ubiquitination of the for phospho-S10-topo I protein may include known systems for automated sequence analysis including but not limited Mass Spectrometry systems including MALDI-TOF, or Matrix Assisted Laser Desorption Ionization—Time of Flight systems; SELDI-TOF-MS ProteinChip array profiling systems, e.g. Machines with Ciphergen Protein Biology System II™ software; systems for analyzing gene expression data (see for example U.S. 2003/0194711); systems for array based expression analysis, for example HT array systems and cartridge array systems available from Affymetrix (Santa Clara, Calif. 95051) AutoLoader, Complete GeneChip® Instrument System, Fluidics Station 450, Hybridization Oven 645, QC Toolbox Software Kit, Scanner 3000 7G, Scanner 3000 7G plus Targeted Genotyping System, Scanner 3000 7G Whole-Genome Association System, GeneTitan™ Instrument, GeneChip® Array Station, HT Array; an automated ELISA system (e.g. DSX® or DS2® form Dynax, Chantilly, Va. or the ENEASYSTEM III®, Triturus®, The Mago® Plus); Densitometers (e.g. X-Rite-508-Spectro Densitometer®, The HYRYS™ 2 densitometer); automated Fluorescence insitu hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACSVantage SE, Becton Dickinson); radio isotope analyzers (e.g. scintillation counters).

Storage Module

In some embodiments, the topo I phosphorylation information determined in the determination module can be read by the storage device. As used herein the "storage device" is intended to include any suitable computing or processing apparatus or other device configured or adapted for storing data or information. Examples of electronic apparatus suitable for use with the present invention include stand-alone computing apparatus; communications networks, including local area networks (LAN), wide area networks (WAN), Internet, Intranet, and Extranet; and local and distributed processing systems. Storage devices also include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon sequence information or expression level information. The data are typically provided in digital form that can be transmitted and read electronically, e.g., via the Internet, on diskette, or any other mode of electronic or non-electronic communication.

Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, other types of volatile and non-volatile memory, any other medium which can be used to store the desired information and which can accessed by a computer, and any suitable combination of the foregoing. The computer readable media does not encompass a data signal or a carrier wave, preferably the computer readable medium is of physical form.

In some embodiments of this aspect and all other aspects of the present invention, a computer readable media can be any available media that can be accessed by a computer. By way of example, and not a limitation, computer readable media may comprise computer storage media and communication media.

As used herein, "stored" refers to a process for encoding information on the storage device. Those skilled in the art can readily adopt any of the presently known methods for recording information on known media to generate manufactures comprising the sequence information or expression level information.

In some embodiments of this aspect and all other aspects of the present invention a variety of software programs and formats can be used to store the phosphorylation information or expression level information on the storage device. Any number of data processor structuring formats (e.g., text file or database) can be employed to obtain or create a medium having recorded thereon the sequence information or expression level information.

In some embodiments of this aspect and all other aspects of the present invention, the reference data stored in the storage device to be read by the comparison module is sequence information data obtained from a control biological sample of the same type as the biological sample to be tested. Alternatively, the reference data are a database, e.g., a part of the entire genome sequence of an organism, or a protein family of sequences, or an expression level profile (RNA, protein or peptide). In one embodiment the reference data are sequence information or expression level profiles that are indicative of a specific disease or disorder.

In some embodiments of this aspect and all other aspects of the present invention, the reference data are electronically or digitally recorded and annotated from databases including, but not limited to GenBank (NCBI) protein and DNA databases such as genome, ESTs, SNPS, Traces, Celara, Ventor Reads, Watson reads, HGTS, etc.; Swiss Institute of Bioinformatics databases, such as ENZYME, PROSITE, SWISS-2DPAGE, Swiss-Prot and TrEMBL databases; the Melanie software package or the ExPASy WWW server, etc., the SWISS-MODEL, Swiss-Shop and other network-based computational tools; the Comprehensive Microbial Resource database (The institute of Genomic Research). The resulting information can be stored in a relational data base that may be employed to determine homologies between the reference data or genes or proteins within and among genomes.

Comparison Module

By providing sequence information, e.g. the presence or absence of a mutation in the RING domain and/or BRCT domain of the BRCA1 protein which decreases the binding affinity of the BRCA1 protein for phospho-S10-topo I protein, and/or decreases the ubiquitination of the for phospho-S10-topo I protein in readable form in the comparison module, it can be used to compare a the reference data within the storage device. The comparison made in computer-readable form provides computer readable content which can be processed by a variety of means. The content can be retrieved from the comparison module, the retrieved content.

In some embodiments of this aspect and all other aspects of the present invention, the "comparison module" can use a variety of available software programs and formats for the comparison operative to compare sequence information determined in the determination module to reference data. In one embodiment, the comparison module is configured to use pattern recognition techniques to compare sequence information from one or more entries to one or more reference data patterns. The comparison module may be configured using existing commercially-available or freely-available software for comparing patterns, and may be optimized for particular data comparisons that are conducted. The comparison module provides computer readable information related to the sequence information that can include, for example, detection of the presence or absence of a sequence (e.g., detection of a mutation or deletion (protein or DNA), information regarding distinct alleles, or omission or repetition of sequences); determination of the concentration of a sequence in the sample (e.g. amino acid sequence/protein expression levels, or nucleotide (RNA or DNA) expression levels), or determination of an expression profile.

In one embodiment, the comparison module permits the comparison of the sequence information of the presence or absence of a mutation in the RING domain and/or BRCT domain of the BRCA1 protein which decreases the binding affinity of the BRCA1 protein for phospho-S10-topo I protein, and/or decreases the ubiquitination of the for phospho-S10-topo I protein from the output data of the determination module with reference data (e.g., wild type BRCA1 sequence information of SEQ ID NO: 5). In some embodiments, the comparison module detects for the presence of mutations in the RING domain previously determined to be associated with at least a 10% decrease in binding affinity and/or at least a 10% decrease E3 ligase activity of BRCA1 (as compared to wild type BRCA1). In some embodiments, the comparison module detects for the presence of mutations in the BRCT domain previously determined to be associated with at least a 10% decrease in binding affinity of the BRCT domain of BRCA1 with phosphr-ser10-topo I (as compared to a wild type BRCA1 protein without such a mutation). Therefore, in some embodiments, the comparison module identifies only those mutations which function to cause the effect of decreased ubiquitination of phosphor-ser10 topo I and/or decreased binding affinity of BRCA1 for phospho-ser10 topo I.

In one embodiment, the comparison module performs comparisons with mass-spectrometry spectra, for example comparisons of peptide fragment sequence information can be carried out using spectra processed in MATLB with script called "Qcealign" (see for example WO2007/022248, herein incorporated by reference) and "Qpeaks" (Spectrum Square Associates, Ithaca, N.Y.), or Ciphergen Peaks 2.1™ software. The processed spectra can then be aligned using alignment algorithms that align sample data to the control data using minimum entropy algorithm by taking baseline corrected data (see for example WO2007/022248, herein incorporated by reference). The retrieved content can be further processed by calculating ratios In one embodiment, the comparison module compares the protein phosphorylation profiles. In one embodiment, the comparison module compares gene expression profiles. For example, detection of gene expression profiles can be determined using Affymetrix Microarray Suite software version 5.0 (MAS 5.0) to analyze the relative abundance of a gene or genes on the basis of the intensity of the signal from probe sets and the MAS 5.0 data files can be transferred into a database and analyzed with Microsoft Excel and Gene-Spring 6.0 software (Silicon genetics). The detection algorithm of MAS 5.0 software can be used to obtain a comprehensive overview of how many transcripts are detected in given samples and allows a comparative analysis of 2 or more microarray data sets.

Any available comparison software can be used, including but not limited to, the Ciphergen Express (CE) and Biomarker Patterns Software (BPS) package, Ciphergen Biosystems, Inc., CA, USA. Comparative analysis can be done with protein chip system software (e.g. The Proteinchip suite for Bio-Rad Laboratories).

In one embodiment, computational algorithms such as expectation-maximization (EM), subtraction and PHASE are used in methods for statistical estimation of haplotypes (see, e.g., Clark, A. G. Inference of haplotypes from PCR-amplified samples of diploid populations. Mol Biol Evol 7, 111-22. (1990); Stephens, M., Smith, N.J. & Donnelly, P. A new statistical method for haplotype reconstruction from population data. Am J Hum Genet 68, 978-89. (2001); Templeton, A. R., Sing, C. F., Kessling, A. & Humphries, S. A cladistic analysis of phenotype associations with haplotypes inferred from restriction endonuclease mapping. II. The analysis of natural populations. Genetics 120, 1145-54. (1988)).

In some embodiments of this aspect and all other aspects of the present invention, the comparison module, or any other module of the invention, may include an operating system (e.g., UNIX) on which runs a relational database management system, a World Wide Web application, and a World Wide Web server. World Wide Web application includes the executable code necessary for generation of database language statements [e.g., Standard Query Language (SQL) statements]. Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware— as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

In some embodiments of this aspect and all other aspects of the present invention, a computer-readable data embodied on one or more computer-readable media may define instructions, for example, as part of one or more programs, that, as a result of being executed by a computer, instruct the computer to perform one or more of the functions described herein (e.g., in relation to computer system 150, or computer readable medium 260), and/or various embodiments, variations and combinations thereof. Such instructions may be written in any of a plurality of programming languages, for example, Java, J, Visual Basic, C, C#, or C++, Fortran, Pascal, Eiffel, Basic, COBOL, etc., or any of a variety of combinations thereof. The computer-readable media on which such instructions are embodied may reside on one or more of the components of either of computer system 150 [machine 10], or computer readable medium 260 described herein, may be distributed across one or more of such components, and may be in transition there between.

In some embodiments of this aspect and all other aspects of the present invention, a computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a processor to implement aspects of the present invention. The computer executable instructions may be written in a suitable computer language or combination of several languages. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Instructions can be provided to the computer systems 150 which refers to a number of computer-implemented steps for processing information in the system. Instructions can be implemented in software, firmware or hardware and include any type of programmed step undertaken by modules of the electronic financing system. The computer system 150 can be connected to a local network. One example of the Local Area Network may be a corporate computing network, including access to the Internet, to which computers and computing devices comprising the financing system are connected. In one embodiment, the LAN conforms to the Transmission Control Protocol/Internet Protocol (TCP/IP) industry standard. Transmission Control Protocol Transmission Control Protocol (TCP) is a transport layer protocol used to provide a reliable, connection-oriented, transport layer link among computer systems. The network layer provides services to the transport layer. Using a two-way handshaking scheme, TCP provides the mechanism for establishing, maintaining, and terminating logical connections among computer systems. TCP transport layer uses IP as its network layer protocol. Additionally, TCP provides protocol ports to distinguish multiple programs executing on a single device by including the destination and source port number with each message. TCP performs functions such as transmission of byte streams, data flow definitions, data acknowledgments, lost or corrupt data re-transmissions, and multiplexing multiple connections through a single network connection Finally, TCP is responsible for encapsulating information into a datagram structure.

In alternative embodiments, the LAN may conform to other network standards, including, but not limited to, the International Standards Organization's Open Systems Interconnection, IBM's SNA, Novell's Netware, and Banyan VINES. The computer system may comprise a microprocessor. A microprocessor may be any conventional general purpose single- or multi-chip microprocessor such as a Pentiumw processor, a PentiumX Pro processor, a 8051 processor, a MISS, processor, a Power PC'processor, or an ALPHAZ processor. In addition, the microprocessor may be any conventional special purpose microprocessor such as a digital signal processor or a graphics processor. The microprocessor typically has conventional address lines, conventional data lines, and one or more conventional control lines.

In some embodiments, the computer system 150 as described herein can include any type of electronically connected group of computers including, for instance, the following networks: Internet, Intranet, Local Area Networks (LAN) or Wide Area Networks (WAN). In addition, the connectivity to the network may be, for example, remote modem, Ethernet (IEEE 802.3), Token Ring (IEEE 802.5), Fiber Distributed Datalink Interface (FDDI) or Asynchronous Transfer Mode (ATM). Note that computing devices may be desktop, server, portable, hand-held, set-top, or any other desired type of configuration. As used herein, an Internet includes network variations such as public internet, a private internet, a secure internet, a private network, a public network, a value-added network, an intranet, and the like.

The computer systems and comparison module can use a variety of operating Systems. For example the computer system 150 can be used in connection with various operating systems such as: UNIX, Disk Operating System (DOS), OS/2, Windows 3. X, Windows 95, Windows 98, and Windows NT. The computer system 150 as described herein can be programmed in any programming language, for example the system may be written in any programming language such as C, C++, BASIC, Pascal, Java, and FORTRAN and ran under the well-known operating system. C, C++, BASIC, Pascal, Java, and FORTRAN are industry standard programming languages for which many commercial compilers can be used to create executable code.

In one embodiment of the invention, the computer system can comprise a pattern comparison software can be used to determine whether patterns of protein phosphorylation profiles are indicative of a subject being responsive to a topo I inhibitor, or the likelihood of efficacy of a topo I inhibitor in the treatment of a cancer.

In some embodiments of this aspect and all other aspects of the present invention, a comparison module provides computer readable data that can be processed in computer readable form by predefined criteria, or criteria defined by a user, to provide a retrieved content that may be stored and output as requested by a user using a display module.

In some embodiments of this aspect and all other aspects of the present invention, the retrieved content can be the identification of presence of a mutation in the RING domain and/or BRCT domain of the BRCA1 protein which decreases the binding affinity of the BRCA1 protein for phospho-S10-topo I protein, and/or decreases the ubiquitination of the for phospho-S10-topo I protein. In anther embodiment, the retrieved content is a positive indicator that the biological sample is responsive to a topo I inhibitor and in another embodiment the retrieved content is an indicator that the biological sample is likely to be responsive to a topo I inhibitor.

Display Module

In some embodiments of this aspect and all other aspects of the present invention, a page of the retrieved content which is the report data from the comparison module is displayed on a computer monitor 120. In one embodiment of the invention, a page of the retrieved content is displayed through printable media 130 and 140. The display module 120 can be any computer adapted for display of computer readable information to a user, non limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD), or any other type of processor. Other displays modules include; speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc In some embodiments of this aspect and all other aspects of the present invention, a World Wide Web browser is used for providing a user interface for display of the retrieved content. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars, etc. conventionally employed in graphical user interfaces. The requests so formulated with the user's Web browser are transmitted to a Web application which formats them to produce a query that can be employed to extract the pertinent information related to the sequence information, the retrieved content, e.g. display of an indication of the presence or absence of mutation or deletion (DNA or protein); display of expression levels of an amino acid sequence (protein); display of nucleotide (RNA or DNA) expression levels; or display of expression, SNP, or mutation profiles, or haplotypes. In one embodiment, the sequence information of the reference sample data is also displayed.

The display module 110 also displays whether the retrieved content is indicative of the subject being responsive or nonresponsive to a topo I inhibitor, e.g. whether the subject has a mutation in the RING domain and/or BRCT domain of the BRCA1 protein which decreases the binding affinity of the BRCA1 protein for phospho-S10-topo I protein, and/or decreases the ubiquitination of phospho-S10-topo I protein, and thus indicates if the subject is more likely to be responsive to a topo I inhibitor as compared to a control subject (e.g., without the BRCA1 mutation). In one embodiment, the retrieved content displays a positive or negative signal regarding the presence or absence of a mutation in the RING domain and/or BRCT domain of the BRCA1 protein which decreases the binding affinity of the BRCA1 protein for phospho-S10-topo I protein, and/or decreases the ubiquitination of the for phospho-S10-topo I protein. In some embodiments, a positive signal indicates that the subject has a mutation in the RING domain and/or BRCT domain of the BRCA1 protein which decreases the binding affinity of the BRCA1 protein for phospho-S10-topo I protein, and/or decreases the ubiquitination of the for phospho-S10-topo I protein, and thus is more likely to be more responsive to a topo I inhibitor. In some embodiments, a negative signal indicates the subject does not have such a mutation in BRCA1 and thus is more likely to be unresponsive to a topo I inhibitor.

Biological Sample

Accordingly in one embodiment of this aspect and all other aspects described herein, a biological sample as defined herein can include a human biological sample, preferably a microdissected human samples, are derived from a small tissue fraction, particularly from a tumor tissue fraction. In some embodiments, the tissue tumor fraction is from SCLC, colon or ovarian cancer, or from a refractory cancer, including but not limited to a breast or cervical cancer tissue fraction. In some embodiments, the human samples are preferably harvested by biopsy and/or surgical extraction, and in some embodiments, the human sample can be stored, for example as frozen biological sample prior to subjecting to the detection of phosphorylation status of topo I polypeptide using the methods, kits, machines, computer systems and media as disclosed herein.

Topoisomerase I Inhibitors

In some embodiments of all aspect of the invention described herein, a topo I inhibitor is any agent which substantially decreases the biological activity of the topo I polypeptide in vitro, in vivo or ex vivo. Exemplary topo I inhibitors are, for example but not limited to camptothecin (CTP) and analogues thereof including but not limited to irinotecan and topotecan, and derivatives thereof.

In one aspect of the present invention, topoisomerase I inhibitors can be any topoisomerase I inhibitor commonly known by persons of ordinary skill in the art. For example, Camptothecin (CPT) represents the most extensively studied mammalian topoisomerase I inhibitor. See R. C. Gallo et al., J. Natl. Cancer Inst., 46, 789 (1971) and B. C. Giovanella et al., Cancer Res., 51 3052 (1991). The broad spectrum of potent antineoplastic activity observed for camptothecin has prompted further efforts to identify other agents which can effectively poison mammalian topoisomerase I. For instance camptothecin analogues are disclosed in U.S. Pat. Nos. 5,364,858, 5,106,742, 5,468,754; 5,604,233; 5,674,873; which are incorporated herein in their entirety by reference.

Camptothecin is a pentacyclic alkaloid initially isolated from the wood and bark of *Camptotheca acuminata* by Wall et al (M. E. Wall, M. C. Wani, C. E. Cook, K. H. Palmer, A. T. McPhail, and G. A. Sim, J. Am. Chem. Soc., 94, 388 (1966). Camptothecin is highly biologically active and displays strong inhibitory activity toward the biosynthesis of nucleic acids. Additionally, camptothecin exhibits potent anti-tumor activity against experimentally transplanted carcinoma such as leukemia L-1210 in mice or Walker 256 tumor in rats. Several methods for the synthesis of camptothecin and camptothecin analogs are known. These synthetic methods include (i) methods in which naturally occurring camptothecin is synthetically modified to produce a number of analogs and (ii) totally synthetic methods. U.S. Pat. Nos. 4,604,463; 4,545,880; and 4,473,692, which are incorporated herein by reference, as well as European Patent Application 0074256 are examples of the former type of synthetic strategy. Additional examples of this strategy can be found in Japanese Patents 84/46,284; 84/51,287; and 82/116,015. These methods required naturally occurring camptothecin which is difficult to isolate and hence these methods are not suitable for the production of large quantities of camptothecin or analogs.

Examples of a variety of totally synthetic routes to camptothecin and camptothecin analogs can be found in the following references: Sci. Sin. (Engl. Ed), 21(1), 87-98 (1978); Fitoterpapia, 45(3), 87-101 (1974); Yakugaku Zashi, 92(6), 743-6 (1972); J. Org. Chem., 40(14), 2140-1 (1975); Hua Hsueh Hsueh Pao, 39(2), 171-8 (1981); J. Chem. Soc., Perkin Trans 1, (5), 1563-8 (1981); Heterocycles, 14(7), 951-3 (1980); J. Amer. Chem. Soc., 94(10), 3631-2 (1972); J. Chem. Soc. D, (7), 404 (1970) and U.S. Pat. No. 4,031,098, which is incorporated herein in its entirety by reference. Wani et al, J. Med. Chem., 23, 554 (1980) discloses a synthesis of camptothecin and camptothecin analogs which involves the reaction of a tricyclic compound with a suitably substituted orthoaminoaldehyde to yield desoxycamptothecin. Desoxycamptothecin is then treated with oxygen to give camptothecin analogs.

Camptothecin and camptothecin analogs are agents that target and inhibit the intranuclear enzyme topoisomerase I. Camptothecin includes but is not limited to 20 (S)-camptothecin, an analog of 20 (S)-camptothecin, a derivative of 20 (S)-camptothecin, a predrug of 20 (S)-camptothecin or pharmaceutical active metabolites thereof, are collectively referred to herein as CPT.

According to any one of the aspects of the invention as disclosed herein, CPT may be 20 (S)-camptothecin or any analog or derivative of 20 (S)-camptothecin. Examples of 20 (S)-camptothecin analogs include, but are not limited to 9-nitro-20 (S)-camptothecin and 9-amino-20 (S)-camptothecin. Examples of 20 (S)-camptothecin derivatives include, but are not limited to 9-methyl-camptothecin, 9-chloro-camptothecin, 9-fluoro-camptothecin, 7-ethyl camptothecin, 10-methyl-camptothecin, 10-chloro-camptothecin, 10-bromo-camptothecin, 10-fluoro-camptothecin, 9-methoxy-camptothecin, 11-fluoro-camptothecin, 7-ethyl-10-hydroxy camptothecin, 10,11-methylenedioxy camptothecin, 10,11-ethylenedioxy camptothecin, 7-(4-methylpiperazinomethylene)-10,11-methylenedioxy camptothecin, camptothecin 20-0-propionate, camptothecin 20-0-butyrate, camptothecin 20-O-valerate, camptothecin 20-O-heptanoate, camptothecin 20-O-nonanoate, camptothecin 20-O-crotonate, camptothecin 20-0-2',3'-epoxy-butyrate, nitrocamptothecin 20-0-acetate, nitrocamptothecin 20-0-propionate, and nitrocamptothecin 20-0-butyrate.

"Camptothecin", as it is referred to in the present invention, includes the plant alkaloid 20 (S)-camptothecin, water insoluble or soluble analogs and derivatives of 20 (S)-camptothecin, prodrugs of camptothecin, and metabolites of 20 (S)-camptothecin. Examples of camptothecin derivatives include, but are not limited to, 9-nitro-20 (S)-camptothecin, 9-amino-20 (S)-camptothecin, 9-methyl-camptothecin, 9-chloro-camptothecin, 9-fluoro-camptothecin, 7-ethyl camptothecin, 10-methyl-camptothecin, 10-chloro-camptothecin, 10-bromo-camptothecin, 10-fluoro-camptothecin, 9-methoxy-camptothecin, 11-fluoro-camptothecin, 7-ethyl-10-hydroxy camptothecin, 10,11-methylenedioxy camptothecin, and 10,11-ethylenedioxy camptothecin, and 7-(4-methylpiperazinomethylene)-10,11-methylenedioxy camptothecin.

Prodrugs of camptothecin include, but are not limited to, esterified camptothecin derivatives as described in U.S. Pat.

No. 5,731,316, such as camptothecin 20-0-propionate, camptothecin 20-0-butyrate, camptothecin 20-O-valerate, camptothecin 20-O-heptanoate, camptothecin 20-O-nonanoate, camptothecin 20-O-crotonate, camptothecin 20-0-2',3'-epoxy-butyrate, nitrocamptothecin 20-O-acetate, nitrocamptothecin 20-0-propionate, and nitrocamptothecin 20-0-butyrate.

Native, unsubstituted, camptothecin can be obtained by purification of the natural extract, or may be obtained from the Stehlin Foundation for Cancer Research (Houston, Tex.). Substituted camptothecins can be obtained using methods known in the literature, or can be obtained from commercial suppliers. For example, 9-nitro-camptothecin may be obtained from SuperGen, Inc. (San Ramon, Calif.), and 9-amino-camptothecin may be obtained from Idec Pharmaceuticals (San Diego, Calif.). Camptothecin and various of its analogs and derivatives may also be obtained from standard fine chemical supply houses, such as Sigma Chemicals.

Camptothecin and camptothecin derivatives useful in all aspect described herein can be modified for optimal delivery. For instance, for optimal delivery methods camptothecin and camptothecin derivatives can be conjugated to any molecule, for example, IT 101 is a conjugate of CYCLOSERT™, and the potent anti-cancer compound camptothecin, which is disclosed in U.S. Pat. No. 7,270,808, which is incorporated herein in its entirety by reference. TOCOSOL Camptothecin is a camptothecin compound that is a conjugate of SN-38. SN-38 is the active ingredient in irinotecan, a camptothecin analog. Preclinical data suggest that TOCOSOL Camptothecin may be more effective and better tolerated than irinotecan, and will be easier and more convenient to administer. TOCOSOL camptothecin is disclosed in U.S. Pat. No. 7,223,770 which is incorporated herein in its entirety by reference.

Figure 1B:
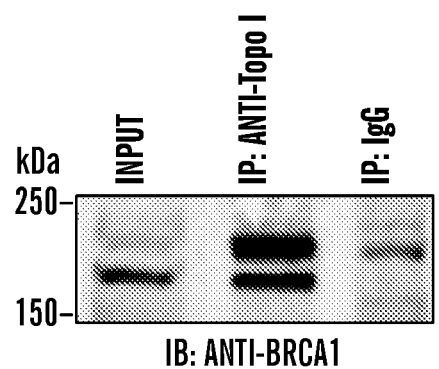

Second-generation camptothecin derivatives have been optimized for improved water solubility to facilitate intravenous drug administration. Highlights resulting from various programs at different companies and institutions are irinotecan 2 and topotecan 3, two compounds which are successfully used in clinical practice, and SN-384, exatecan 5, liposomal lurtotecan 6 (OSI-211) and CKD-602 7, which are in advanced stages of clinical development. The chemical structures of these compounds are shown in FIGS. 1A and 1B of U.S. Patent Application US20080280935, which is incorporated herein in its entirety by reference.

SN-38 is a camptothecin derivative that contains a hydroxyl group at the C10 position and an ethyl group at the C7 position. Irinotecan is a camptothecin derivative (it may also be viewed as a derivative of SN-38) that contains a sidechain at the C10 position and an ethyl group at the C7 position. Irinotecan was discovered at Yakult Honsha and was first approved in Japan in 1994 (CAMPTOTESIN®) for lung, cervical and ovarian cancer. Today it is marketed in the U.S. by Pharmacia (CAMPTOSAR®) and by Aventis in Europe (CAMPTO®). Irinotecan is a prodrug which is cleaved in vivo by carboxylic esterases, particularly by hCE-2, to release the active metabolite SN-38.

The synthesis of irinotecan has been described in the chemical literature and in patents. A common approach to the synthesis of irinotecan is to form SN-38 and then add a sidechain to the C10 position of SN-38, to thereby form irinotecan. U.S. Pat. No. 4,604,463, which is incorporated herein by reference in its entirety, is one example of a patent that describes this approach, wherein either an activated form of the sidechain is separately formed and then reacted with SN-38, or the C10 hydroxyl group is activated and then in a separate reaction the sidechain is added. Another method to synthesis of irinotecan has been described in U.S. Patent Application US20080280935, which is incorporated herein in its entirety by reference.

Topotecan topoisomerase I inhibitor can be produced as described in U.S. Pat. No. 6,660,861, which is incorporated herein by reference. Other topoisomerase I inhibitors can be used, for example, Hoechst 33342 (1), 2'-(4-ethoxyphenyl)-5-(4-methyl-1-piperazinyl)-2,5'-bi-1H-benzimidazole is an inhibitor of topoisomerase I, and is disclosed in U.S. Pat. No. 5,807,874 which is incorporated herein in its entirety by reference.

Topotecan, a semisynthetic analog of camptothecin, was shown to inhibit both acute and chronic HIV-1 infections in vitro. J. L. Zhang, et al. "Topoisomerase inhibits human immunodeficiency virus type 1 infection through a topoisomerase-independent mechanism in a cell line with altered topoisomerase I" Antimicrob. Agents Chemother. 41: 977-981 (1997). The antiviral effects of topotecan were observed not only in the topoisomerase-mutated CPT-K5 cell line but also in peripheral blood mononuclear cells (PBMC) acutely infected with clinical isolates and in OM10.1 cells latently infected with HIV and activated by tumor necrosis factor alpha (TNF-a). It was again hypothesized that this camptothecin targets factors in virus replication other than cellular topoisomerase I and inhibits cytokine-mediated activation in latently infected cells by means other than cytotoxicity.

Other topo I inhibitors include, for example, but not limited to, antibodies (polyclonal or monoclonal), neutralizing antibodies, antibody fragments, peptides, proteins, peptide-mimetics, aptamers, oligonucleotides, hormones, small molecules, nucleic acids, nucleic acid analogues, carbohydrates or variants thereof that function to inactivate the nucleic acid and/or protein of the gene products identified herein, and those as yet unidentified. Nucleic acids include, for example but not limited to, DNA, RNA, oligonucleotides, peptide nucleic acid (PNA), pseudo-complementary-PNA (pcPNA), locked nucleic acid (LNA), RNAi, microRNAi, siRNA, shRNA etc. Topo I inhibitors can also be chemicals, small molecules, chemical entities, nucleic acid sequences, nucleic acid analogues or protein or polypeptide or analogue or fragment thereof. In some embodiments, a nucleic acid topo I inhibitor is DNA or RNA, and nucleic acid analogues, for example can be PNA, pcPNA and LNA. A nucleic acid topo I inhibitor can be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc.

Alternatively, a topo I inhibitor can be a protein and/or peptide topo I inhibitor or functional fragment thereof, as that term is defined herein. For example, topo I inhibitor can be, for example but not limited to mutated proteins; therapeutic proteins and recombinant proteins. Proteins and peptides inhibitors can also include for example; mutated proteins, genetically modified proteins, peptides, synthetic peptides, recombinant proteins, chimeric proteins, antibodies, humanized proteins, humanized antibodies, human antibodies, single chain antibodies and Fab fragments, chimeric antibodies, modified proteins and fragments thereof.

In some embodiments, a topo I inhibitor is a nucleic acid, nucleic acid analogues, peptides, phage, phagemids, polypeptides, peptidomimetics, ribosomes, aptamers, antibodies, small or large organic or inorganic molecules, or any combination thereof.

Methods to Treat a Subject Identified to be Responsive to a Topo I Inhibitor.

Exemplarily examples of topo I inhibitors are for example but not limited to, camptothecin (CTP) and analogues thereof including but not limited to irinotecan and topotecan, and derivatives thereof disclosed in the section entitled "topo I inhibitors" herein.

Another aspect of the present invention relates to increasing the efficacy of topoisomerase I inhibitors. Accordingly, in some embodiments, where a subject is identified to have a mutation in the RING domain and/or BRCT domain which decreases the BRCA1 binding affinity for phosphor-ser10 topo I and/or decreases ubiquitination, the subject will likely be responsive to topo I inhibitors, and thus can be administered a topo I inhibitor for therapeutic purposes, e.g., for the treatment of cancer. In alternative embodiments and all other aspects described herein, where a biological sample obtained from the subject has been determined not to have a mutation in the BRCA1 gene which results in a decrease in the binding (or binding-affinity) of BRCA1 protein to the phosphor-ser10-topo I protein, and/or decrease the ubiquitination of the phosphor-ser10-topo I protein, and thus an increase in the degradation of phosho-ser10-topo I protein degradation, a subject from which the biological sample was obtained can be administered an agent which decreases the phosphorylation of topo I, for example the subject can be administered an agent which is not a topo I inhibitor. Alternatively, the subject can be administered an agent which dephosphorylates S10 of the topo I polypeptide, which can be administered concurrently with the administration of a topo I inhibitor. In some embodiments, an agent which dephosphorylates topo I, such as an agent which dephosphorylates S10 of topo I can be administered prior to, concurrent with, or subsequent to the administration of a topo I inhibitor as that term is defined herein.

In another embodiment, the subject can be administered an agent which has been identified to decrease (e.g., decrease the binding affinity) or interfere with the BRCA1-phosphor-ser10-topo I protein interaction, for example, a compound which inhibits the BRCT domain interaction with phospho-ser10 topo I y at least about 10%, or at least about 20% or at least about 30% or at least about 40% or more than 40%, as discovered, for example, using the HTS assay as disclosed herein in the Examples.

Accordingly, another aspect of the present invention relates to administering to a subject an agent which increases the sensitivity (i.e. decreases the non-responsiveness) of a subject to a topoisomerase I inhibitor, where an agent which increases the sensitivity to a topo I inhibitor (i.e. a topo I inhibitor sensitivity agent) is for example an agent which results in the dephosphorylation of topo I, preferably the dephosphorylation of S10 of topo I, or alternatively, decreases the binding affinity of the BRCA1 protein for the phosphor-ser10-topo I protein. Such methods are particularly useful when a subject has been identified to likely be non-responsive to a topoisomerase I inhibitor (e.g., does not comprise a mutation in the RING domain and/or BRCT domain that decreases the BRCA1-phospho-ser10 topo I interaction and/or decreases ubiquitination of phospho-ser10-topo I, as disclosed herein) using the methods, kits, machines, computer systems and media as disclosed herein. As discussed above, a topo I inhibitor which can be administered subsequent to, concurrent with or prior to administration of an agent which results in the dephosphorylation of topo I, preferably the dephosphorylation of S10 of topo I is camptothecin (CPT), or CPT analogues such as topotecan and irinotecan and derivatives thereof, including but not limited CPT compounds, CPT metabolites, derivatives or analogues thereof having a skeleton similar to CPT.

Those skilled in the art will appreciate that a topo I inhibitor to which the present invention refers are not limited to the above-mentioned specific agents but include any compound or entity that functions as a topo I inhibitor, i.e. any agent which decreases the biological activity of the topo I polypeptide.

Antagonists or Inhibitor Agents of DNA-PK

In some embodiments of this aspect of the invention which relates to increasing the efficacy of topoisomerase I inhibitors, an agent which increases the sensitivity (i.e. decreases the non-responsiveness and is referred to herein as a topo I inhibitor sensitivity agent) of the subject to a topoisomerase I inhibitor is an anti-phospho-S10 topo I antibody. In an alternative embodiment, a topo I inhibitor sensitivity agent is an inhibitor of the kinase DNA-PK. In some embodiments, an inhibitor of the kinase DNA-PK is NU7026, 2-morpholin-4-yl)-benzo[h]chromen-4-one, or derivatives or analogues thereof, as disclosed herein in the examples. Other examples of such inhibitors of DNA-PK include those disclosed in U.S. Pat. Nos. 7,402,607, 7,226,918, and in U.S. Applications US2007/238729, US2004/192687, US2008,0242664, US2008/0038277, US2007/0167441 and US2009/0035394 which are all incorporated herein in their entirety by reference. Other examples of such inhibitors of DNA-PK include, for example, but not limited to, antibodies (polyclonal or monoclonal), neutralizing antibodies, antibody fragments, peptides, proteins, peptide-mimetics, aptamers, oligonucleotides, hormones, small molecules, nucleic acids, nucleic acid analogues, carbohydrates or variants thereof that function to inactivate the nucleic acid and/or protein of the gene products identified herein, and those as yet unidentified. Nucleic acids include, for example but not limited to, DNA, RNA, oligonucleotides, peptide nucleic acid (PNA), pseudo-complementary-PNA (pcPNA), locked nucleic acid (LNA), RNAi, microRNAi, siRNA, shRNA etc. The inhibitors can be selected from a group of a chemical, small molecule, chemical entity, nucleic acid sequences, nucleic acid analogues or protein or polypeptide or analogue or fragment thereof. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide inhibitor or fragment thereof, can be, for example, but not limited to mutated proteins; therapeutic proteins and recombinant proteins. Proteins and peptides inhibitors can also include for example; mutated proteins, genetically modified proteins, peptides, synthetic peptides, recombinant proteins, chimeric proteins, antibodies, humanized proteins, humanized antibodies, chimeric antibodies, modified proteins and fragments thereof.

Accordingly, in some embodiments of this aspect and all other aspects described herein, a topo I inhibitor is administered in combination with an agent which increases the sensitivity of a cell to said topo I inhibitor, wherein in one embodiment an agent is an agent which increases dephosphorylation of topo I polypeptide, such as decreases phosphorylation at serine 10 of topo I polypeptide, and in an alternative embodiment, the agent is an agent which inhibits the biological activity of DNA-PK, thus inhibiting phosphorylation of topo I by DNA-PK. In some embodiments, inhibition of DNA-PK can occur via inhibition of nucleic acid transcripts encoding DNA-PK, for example inhibition of messenger RNA (mRNA). In alternative embodiments, inhibition of DNA-PK is inhibition of the expression and/or inhibition of activity of the gene product of DNA-PK, for example the polypeptide or protein of DNA-PK. As used herein, the term "gene product" refers to RNA transcribed from a gene, or a polypeptide encoded by a gene or translated from RNA.

In some embodiments, inhibition of DNA-PK is by an agent. One can use any agent, for example but are not limited to nucleic acids, nucleic acid analogues, peptides, phage, phagemids, polypeptides, peptidomimetics, ribosomes, aptamers, antibodies, small or large organic or inorganic molecules, or any combination thereof. In some embodiments, agents useful in methods of the present invention include agents that function as inhibitors of DNA-PK, for example inhibitors of mRNA encoding DNA-PK.

Agents useful in the methods as disclosed herein can also inhibit gene expression (i.e. suppress and/or repress the expression of the gene). Such agents are referred to in the art as "gene silencers" and are commonly known to those of ordinary skill in the art. Examples include, but are not limited to a nucleic acid sequence, for an RNA, DNA or nucleic acid analogue, and can be single or double stranded, and can be selected from a group comprising nucleic acid encoding a protein of interest, oligonucleotides, nucleic acids, nucleic acid analogues, for example but are not limited to peptide nucleic acid (PNA), pseudo-complementary PNA (pc-PNA), locked nucleic acids (LNA) and derivatives thereof etc. Nucleic acid agents also include, for example, but are not limited to nucleic acid sequences encoding proteins that act as transcriptional repressors, antisense molecules, ribozymes, small inhibitory nucleic acid sequences, for example but are not limited to RNAi, shRNAi, siRNA, micro RNAi (miRNA), antisense oligonucleotides, etc.

As used herein, agents useful in the method as inhibitors of DNA-PK can be any type of entity, for example but are not limited to chemicals, nucleic acid sequences, nucleic acid analogues, proteins, peptides or functional fragments thereof. In some embodiments, the agent is any chemical, entity or moiety, including without limitation, synthetic and naturally-occurring non-proteinaceous entities. In certain embodiments, an agent is a small molecule having a chemical moiety. For example, in some embodiments, the chemical moiety is a pyrimidinone-based compound as disclosed herein.

In alternative embodiments, agents useful in the methods as disclosed herein are proteins and/or peptides or fragment thereof, which inhibit the gene expression of DNA-PK or the function of the DNA-PK protein. Such agents include, for example but are not limited to protein variants, mutated proteins, therapeutic proteins, truncated proteins and protein fragments. Protein agents can also be selected from a group comprising mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof.

Alternatively, agents useful in the methods as disclosed herein as inhibitors of DNA-PK can be a chemicals, small molecule, large molecule or entity or moiety, including without limitation synthetic and naturally-occurring non-proteinaceous entities. In certain embodiments the agent is a small molecule having the chemical moieties as disclosed herein.

In particular embodiments the antagonist is a nucleic-acid based inhibitor of expression of polynucleotide encoding DNA-PK or fragments thereof. Suitable molecules include small interfering RNA (siRNA) species, antisense constructs, such as antisense oligonucleotides, and catalytic antisense nucleic acid constructs. Suitable molecules can be manufactured by chemical synthesis, recombinant DNA procedures or, in the case of antisense RNAi by transcription in vitro or in vivo when linked to a promoter, by methods known to those skilled in the art.

One suitable technology for inhibiting gene expression, known as RNA interference (RNAi), (see, e.g. Chuang et al. (2000) PNAS USA 97: 4985) may be used for the purposes of the present invention, according to known methods in the art (for example Fire et al. (1998) Nature 391: 806-811; Hammond, et al. (2001) Nature Rev, Genet. 2: 110-1119; Hammond et al. (2000) Nature 404:293-296; Bernstein et al. (2001) Nature 409: 363-366; Elbashir et al (2001) Nature 411: 494-498; WO 99/49029 and WO 01/70949, the disclosures of which are incorporated herein by reference), to inhibit the expression of DNA-PK. RNAi refers to a means of selective post-transcriptional gene silencing by destruction of specific mRNA by small interfering RNA molecules (siRNA). The siRNA is typically generated by cleavage of double stranded RNA, where one strand is identical to the message to be inactivated. Double-stranded RNA molecules may be synthesized in which one strand is identical to a specific region of the mRNA transcript of DNA-PK and introduced directly. Alternatively corresponding double stranded DNA (dsDNA) can be employed, which can be converted into dsRNA. Methods for the synthesis of suitable siRNA molecules for use in RNAi and for achieving post-transcriptional gene silencing are known to those of skill in the art. Those skilled in the art will also appreciate that a range of suitable siRNA constructs capable of inhibiting the expression of DNA-PK can be identified and generated based on knowledge of the sequence of the gene in question using routine procedures known to those skilled in the art without undue experimentation.

The isolated inhibitory nucleic acid construct comprising a nucleic acid sequence specific to a least a portion of the polynucleotide encoding DNA-PK, wherein the nucleic acid construct substantially inhibits the expression of DNA-PK in tumor cells. Alternatively, inhibitory nucleic acid constructs may comprise of a nucleic acid sequences specific to at least a portion of a polynucleotide encoding one or more genes which regulate the expression of DNA-PK. Genes that regulate the expression of DNA-PK comprise, for example, but not limited to, transcription factors, co-activators, activators, enhancers and cofactors of DNA-PK.

Those skilled in the art will appreciate that there need not necessarily be 100% nucleotide sequence match between the target sequence and the siRNA sequence. The capacity for mismatch there between is dependent largely on the location of the mismatch within the sequences.

In particular embodiments of the invention suitable inhibitory nucleic acid molecules may be administered to the tumor cells in a vector. The vector may be a plasmid vector, a viral vector, or any other suitable vehicle adapted for the insertion and foreign sequence and for the introduction into eukaryotic cells. The vector can be an expression vector capable of directing the transcription of the DNA sequence of inhibitory nucleic acid molecules into RNA. Viral expression vectors can be selected from a group comprising, for example, retroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the inhibitory nucleic add molecule in the tumor cells in high copy number extra chromosomal DNA thereby eliminating potential effects of chromosomal integration.

A further means of substantially inhibiting the expression of DNA-PK may be achieved by introducing catalytic antisense nucleic acid constructs, such as ribozymes, which are capable of cleaving RNA transcripts and thereby preventing the production of wildtype protein. Ribozymes are targeted to and anneal with a particular sequence by virtue of two regions of sequence complementary to the target flanking the ribozyme catalytic site. After binding the ribozyme cleaves the target in a site specific manner. The design and testing of ribozymes which specifically recognize and cleave sequences of isoforms of DNA-PK can be achieved by techniques well known to those in the art (for example Lleber and Strauss, (1995) Mol Cell Biol 15:540.551, the disclosure of which is incorporated herein by reference).

Alterative antagonists of DNA-PK may include antibodies. Suitable antibodies include, but are not limited to polyclonal antibodies, monoclonal antibodies, chimeric antibodies, humanized antibodies, human antibodies, single chain antibodies and Fab fragments.

Antibodies may be prepared from discrete regions of fragments of the polypeptide of interest. An antigenic polypeptide contains at least about 5, and preferably at least about 10 amino acids.

Methods for the generation of suitable antibodies will be readily appreciated by those skilled in the art. For example, a suitable monoclonal antibody, typically containing Fab portions, may be prepared using the hybridoma technology described in Antibodies—A Laboratory Manual Harlow and Lane, Eds. Cold Spring Harbor Laboratory, N.Y. (1988), the disclosure of which is incorporated herein by reference.

Similarly, there are various procedures known in the art which may be used for the production of polyclonal antibodies to polypeptides of interest as disclosed herein. For the production of polyclonal antibodies, various host animals, including but not limited to rabbit mice, rats, sheep, goats, etc, can be immunized by injection with a polypeptide, or fragment or analogue thereof. Further, the polypeptide or fragment or analogue thereof can be conjugated to an immunogenic carrier, e.g., bovine serum albumin (BSA) or keyhole limpet hemocyanin (KLH). Also, various adjuvants may be used to increase the immunological response, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*Bacillus* Calmette-Guerin) and *Corynebacterium parvum*.

Screening for the desired antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and Immunoelectrophoresis assays, and the like (see, for example, Ausubel et al., eds, 1994, Current Protocols in Molecular Biology, Vol. 1, John Wiley & Sons, Inc., New York). Antibody binding may be detected by virtue of a detectable label on the primary antibody. Alternatively, the primary antibody may be detected by virtue of its binding with a secondary antibody or reagent which is appropriately labeled. Numerous methods are known by persons of ordinary skill in the art to detecting binding in an immunoassay and are within the scope of the present invention.

Also included within the scope of the present invention are alternative forms to inhibit the expression of DNA-PK, including, for example, small molecule or other non-nucleic acid or non-proteinaceous inhibitors. Such inhibitors may be identified by those skilled in the art by screening using routine techniques.

Selection of Subjects Amenable to Determining their Responsiveness to a Topo I Inhibitor Treatment.

Embodiments of the invention provide methods for predicting if a topo I inhibitor treatment will be effective in a subject, based on the discovery that the presence of specific mutations in the BRCA1 gene, e.g., particular BRCA1 mutations in the RING domain and/or BRCT domain which result in a decreased binding affinity of the BRCA1 protein for the phospho-ser10-topo I protein, and/or decreased ubiquitination of phospho-ser10-topo I, and identify an increased likelihood that the topo I inhibitor will be effective in a subject where the topo I inhibitor is being used for the treatment of cancer. Subjects amenable to testing for the presence of mutations in the BRCA1 gene using the methods, kits, machines, computer systems and media as disclosed herein include subjects at risk of a cancer, as well as subjects with cancer.

In one embodiment, the cancer is breast cancer of the triple-negative subtype. In some embodiments, the cancer is ovarian cancer. Embodiments of the invention also provide methods for altering the sensitivity (i.e. increasing the sensitivity) of a subject not having the mutations as disclosed herein to a topo I inhibitor treatments, in particular CPT or analogues thereof, by co-administering an agent which dephosphorylates S10 on the topo I polypeptide and/or inhibits phosphorylation at S10 of topo I, for example an antagonists to DNA-PK.

Accordingly, the methods of the invention relate to the analysis and treatment of a variety of tumor cell types, to a topo I inhibitor treatment. For example, the tumor cell types can be selected from a group comprising of gastrointestinal cancer, gastric cancer, squamous cell carcinomas (SCC), head and neck cancer, lung cancer, non-small cell lung cancer (NSCLC) and small-cell lung cancer (SCLC), lymphoma, sarcoma, primary and metastatic melanoma, thymoma, non-Hodgkin's lymphoma, Hodgkin's lymphoma, cancer of the nervous system, brain cancer, bone-marrow cancer, bone cancer, kidney cancer, uterine cancer, cervical cancer, colon cancer, retina cancer, skin cancer, bladder cancer, colon cancer, esophageal cancer, testicular cancer, cervical cancer, liver cancer, renal cancer, pancreatic cancer, genital-urinary cancer, gastrointestinal, gum cancer, tongue cancer, kidney cancer, nasopharynx cancer, stomach cancer, endometrial cancer and bowel tumor cell cancer, adrenocarcinomas such as prostate cancer, ovarian cancer, breast cancer, and pancreatic cancer.

In some embodiments, subjects amenable to testing for the mutations in the RING domain and/or BRCT domain of BRCA1 gene which result in a decreased binding affinity of the BRCA1 protein for the phospho-ser10-topo I protein, and/or decreased ubiquitination of phospho-ser10-topo I using the methods, kits, machines, computer systems and media as disclosed herein include subjects with breast cancer, in particular the triple negative subtype breast cancer, which is characterized by ER/PR-negative also lacking HER2 expression. In alternative embodiments, subjects amenable to testing using the methods as disclosed herein are subjects with ovarian cancer, squamous cell carcinomas (SCC) or prostate cancer.

In some embodiments, subjects amenable to testing for mutations in the RING domain and/or BRCT domain of BRCA1 gene which result in a decreased binding affinity of the BRCA1 protein for the phospho-ser10-topo I protein, and/or decreased ubiquitination of phospho-ser10-topo I using the methods, kits, machines, computer systems and media as disclosed herein include any subject currently being administered or about to be administered a topo I inhibitor based treatment, such as such as CPT or an analogue, mimetic or derivatives thereof. In alternative embodiments, subjects amenable to the diagnostic tests as disclosed herein to detect the presence of mutations in the RING domain and/or BRCT domain of BRCA1 gene which result in a decreased binding affinity of the BRCA1 protein for the phospho-ser10-topo I protein, and/or decreased ubiquitination of phospho-ser10-topo I using the methods, kits, machines, computer systems and media as disclosed herein, include any subject that has been administered a topo I inhibitor, such as CPT or analogues or derivatives thereof, in the past and was found that such treatment was not effective, or the subject is, or has had cancer remission. Testing of such subjects using the methods, kits, machines, computer systems and media as disclosed herein is useful to determine if the failure of the prior administration of a topo I inhibitor treatment was due to the absence of the mutations as disclosed herein, and thus identifies a subject likely to be unresponsive to such a topo I inhibitor treatment. Accordingly, a physician can direct such subjects to be administered an alternative treatment regime not involving a topo I inhibitor in future cancer treatments or prophylactic cancer treatments, or can administer an agent which interferes with (e.g., inhibits) with the BRCA1-phospho-ser10-topo I interaction, for example an agent identified using the HTS as disclosed in the Examples.

In some embodiments, subjects amenable to testing for mutations in the RING domain and/or BRCT domain of BRCA1 gene which result in a decreased binding affinity of the BRCA1 protein for the phospho-ser10-topo I protein, and/or decreased ubiquitination of phospho-ser10-topo I include adult and pediatric oncology subjects which have cancers such as solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, askocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Kaposi's sarcoma.

In some embodiments, subjects amenable to testing for mutations in the RING domain and/or BRCT domain of BRCA1 gene which result in a decreased binding affinity of the BRCA1 protein for the phospho-ser10-topo I protein, and/or decreased ubiquitination of phospho-ser10-topo I using the methods, kits, machines, computer systems and media as disclosed herein include subjects with cancers such as, but are not limited to, bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor.

In some embodiments, subjects amenable to testing for mutations in the RING domain and/or BRCT domain of BRCA1 gene which result in a decreased binding affinity of the BRCA1 protein for the phospho-ser10-topo I protein, and/or decreased ubiquitination of phospho-ser10-topo I using the methods, kits, machines, computer systems and media as disclosed herein include subjects identified with or having increased risk of cancer, for example subjects identified to carry a genetic mutation or polymorphism associated with an increase risk of developing cancer. Such mutations and genetic susceptibility genes and loci are commonly known by persons skilled in the art, for example some of the more commonly known genes where a mutation is associated with increase in cancer include, but are not limited to; BRAC1, BRAC2, EGFR, EIF4A2, ERBB2, RB1, CDKN2A, P53, INK4a, APC, MLH1, MSH2, MSH6, WTI, NF1, NF2, and VHL (see world wide web at: "cancer.org/docroot/ETO/content/ETO_1_4x_oncogenes_and_tumor_suppressor_genes.asp").

In some embodiments, subjects amenable to determination of the presence of mutations in the RING domain and/or BRCT domain of BRCA1 gene which result in a decreased binding affinity of the BRCA1 protein for the phospho-ser10-topo I protein, and/or decreased ubiquitination of phospho-ser10-topo I using the methods, kits, machines, computer systems and media as disclosed have been identified to have cancer as determined by a number of cancer screens commonly known by persons of ordinary skill in the art, for example a number of biochemical and genetic markers or other biomarkers. Biomarkers are defined as cellular, biochemical, molecular or genetic alterations by which a normal, abnormal or simply biologic process can be recognized or monitored. Biomarkers are measurable in biological media, such as human tissues, cells or fluids. Biomarkers could be used to identify pathological processes before individuals become symptomatic or to identify individuals who are responsive to cancer.

Several classes of biomarkers in cancer cells and bodily fluids have been studied, mostly in laboratories examining specific observations but also in limited clinical settings. Several biomarkers have shown only limited utility: e.g., CD44, telomerase, transforming growth factor-α (TGF-α)3, transforming growth factor-β (TGF-β), epidermal growth factor receptor erbB-2 (erbB-2), epidermal growth factor receptor erbB-3 (erbB-3), mucin 1 (MUC1), mucin 2 (MUC2) and cytokeratin 20 (CK20). Other biomarkers are used in clinical practice and include, for example Prostate specific antigen (PSA) and cancer antibody or tumor marker 125 (CA125). Several protein markers can be used as cancer biomarkers, for example but not limited to, Fecal occult blood test (FOBT), which is a protein biomarker shown to decrease cause-specific mortality in cancer screens.

In some embodiments, the biological sample obtained from the subject is from a biopsy tissue sample, and in some embodiments, the sample is from a tumor or cancer tissue sample. The testing for the phosphorylation status of topo I protein, and in particular the level of phospho-S10 topo I polypeptide can be determined using the methods, kits, machines, computer systems and media as disclosed herein and include, without limitation known, any automated method operated by the skilled artisan, for example by automated immunohistochemical methods, or machines such as mass spectrometry.

Application of the Methods, Kits, Machines, Computer Systems, Computer Readable Media:

In the research context, embodiments of the invention may provide a method for drug screening and reporting of drug effects in preclinical and clinical trials. The inventive methods can be used to identify which subjects are likely to be responsive to a topo I inhibitor, assess the effectiveness of topo I inhibitors in a population of subjects alone or in combination with other anticancer drugs and other therapeutic agents, improve the quality and reduce costs of clinical trials, discover the subset of positive responders to a particular class of topoisomerase I inhibitor (i.e. stratifying patient populations), improve therapeutic success rates, and/or reduce sample sizes, trial duration and costs of clinical trials.

In the health care context, embodiments of the invention may provide a service to physicians that will enable the physicians to tailor optimal personalized patient therapies. For example, a biological sample taken from a subject can be sent by the pathologist and/or clinical oncologist to a laboratory facility, for example, one such lab is operated by Theranostics Health, LLC. The laboratory may analyze for the presence of mutations in the RING domain and/or BRCT domain of BRCA1 gene which result in a decreased binding affinity of the BRCA1 protein for the phospho-ser10-topo I protein, and/or decreased ubiquitination of phospho-ser10-topo I in a biological sample from a subject and provide a report to the physician or health care provider. The laboratory may provide the treating pathologist or clinical oncologist with a report indicating if the subject from which the biological sample was taken is responsive or unresponsive to a topo I inhibitor and optionally provide a listing the topo I inhibitors which can be used should the subject be identified as being responsive, or alternative anti-cancer agents which are not topo I inhibitors, or a list of topo I inhibitor sensitivity agents to be used in combination with a topo I inhibitor should the subject be identified to be unresponsive to a topo I inhibitor. This may enable a physician to tailor the therapy of the subject, e.g., prescribe the right therapy to the right patient at right time, provide a higher treatment success rate, spare the patient unnecessary toxicity and side effects, reduce the cost to patients and insurers of unnecessary or ineffective medication, and improve patient quality of life, eventually making cancer a managed disease, with follow up assays as appropriate. For example, if the laboratory results indicate that the subject has a mutation in the RING domain and/or BRCT domain of BRCA1 which decreases the BRCA1 binding affinity for phosphor-ser10 topo I and/or decreases ubiquitination of phosphor-ser10 topoI, the physician can administer the topo I alone or in conjunction with other agents, e.g., other anti-cancer agents and/or phosphatases which reduce the phosphorylation (e.g., at the serine residue) of phosphor-ser10 topo I. Alternatively, in some embodiments, if the laboratory results indicate that the subject has does not have a mutation in the RING domain and/or BRCT domain of BRCA1 which decreases the BRCA1 binding affinity for phosphor-ser10 topo I and/or decreases ubiquitination of phosphor-ser10 topoI, the physician can administer an anti-cancer agent which is not a topo I inhibitor.

Accordingly, physicians can use the reported information to tailor optimal personalized patient therapies instead of the current "trial and error" or "one size fits all" methods used to prescribe chemotherapy under current systems. The inventive methods may establish a system of personalized medicine with resect to the treatment of cancer with topo I inhibitors.

In Some Embodiments, the Present Invention May be Defined in any of the Following Numbered Paragraphs:

1. An assay to determine if a subject with cancer will benefit from treatment with an a topoisomerase I inhibitor, the assay comprising:
   i. contacting a biological sample obtained from the subject with at least one probe to detect the presence of a mutation in the RING domain and/or BRCT domain of the BRCA1 gene;
   ii. measuring the presence of at least one mutation in the RING domain and/or BRCT domain of the BRCA1 gene, wherein the mutation in the RING domain and/or BRCT domain decreases the binding affinity of the BRCA1 protein for the phosphorylated serine 10 topoisomerase protein or decreases the E3 ligase activity of BRCA1 and/or decreases the binding affinity of BRCA1 for BARD1 and/or a E2 conjugating enzyme;
   iii. wherein the presence of a mutation in the RING domain and/or BRCT domain which decreases the binding affinity of the BRCA1 protein for the phosphorylated serine 10 topoisomerase protein or decreases the E3 ligase activity of BRCA1 and/or decreases the binding affinity of BRCA1 for BARD1 and/or a E2 conjugating enzyme identifies a subject who would be predicted to benefit from the treatment with a topoisomerase inhibitor.

2. An assay, the assay comprising:
   a. subjecting a biological sample from a human subject diagnosed with having cancer to determine a treatment regimen, to at least one genotyping assays which determines the presence of at least one mutation in the RING domain and/or BRCT domain of the BRCA1 gene, wherein the mutation in the RING domain and/or BRCT domain decreases the binding affinity of the BRCA1 protein for the phosphorylated serine 10 topoisomerase protein or decreases the E3 ligase activity of BRCA1 and/or decreases the binding affinity of BRCA1 for BARD1 and/or a E2 conjugating enzyme, and
   b. selecting a treatment regimen that comprises administration of a topoisomerase inhibitor when at least one or a combination of the following mutations is determined to be present:
      i. a mutation in the BRCT domain which decreases the binding affinity of the BRCA1 protein for the phosphorylated serine 10 topoisomerase protein;
      ii. a mutation in the RING domain which decreases the E3 ligase activity of BRCA1;
      iii. a mutation in the RING domain which decreases the binding affinity of BRCA1 for BARD1; or
      iv. a mutation in the RING domain which decrease the binding affinity of BRCA1 for an E2 conjugating enzyme.
3. The assay of paragraph 1 or 2, wherein at least one mutation in the RING domain and/or BRCT domain of the BRCA1 results in at least a 10% decrease the binding affinity of the BRCA1 protein for the phosphorylated serine 10 topoisomerase protein or results in at least a 10% decrease in the E3 ligase activity of BRCA1 and/or results in at least a 10% decrease in the binding affinity of BRCA1 for BARD1 and/or results in a E2 conjugating enzyme as compared to a wild type BRCA1 gene identifies a subject who would be predicted to benefit from the treatment of a topoisomerase inhibitor.
4. The assay of paragraph 1 or 2, wherein at least one mutation in the RING domain and/or BRCT domain of the BRCA1 that results in a statistically significant decrease the binding affinity of the BRCA1 protein for the phosphorylated serine 10 topoisomerase protein or a statistically significant decrease in the E3 ligase activity of BRCA1 and/or in a statistically significant decrease in the binding affinity of BRCA1 for BARD1 and/or a E2 conjugating enzyme as compared to a wildtype BRCA1 gene identifies a subject who would be predicted to benefit from the treatment of a topoisomerase inhibitor.
5. The assay of paragraph 4, wherein the statistically significant decrease is a decrease of at least one standard deviation.
6. The assay of paragraph 4, wherein the statistically significant decrease is a decrease of at least two standard deviation.
7. The assay of any of paragraphs 1-6, further comprising the step of treating a subject with a topoisomerase inhibitor when a subject is determined to have the presence of a mutation in the RING domain and/or BRCT domain which decreases the binding affinity of the BRCA1 protein for the phosphorylated serine 10 topoisomerase protein or decreases the E3 ligase activity of BRCA1 and/or decreases the binding affinity of BRCA1 for BARD1 and/or a E2 conjugating enzyme, and not administration a topoisomerase inhibitor when the subject does not have a mutation in the RING domain and/or BRCT domain which decreases the binding affinity of the BRCA1 protein for the phosphorylated serine 10 topoisomerase protein or decreases the E3 ligase activity of BRCA1 and/or decreases the binding affinity of BRCA1 for BARD1 and/or a E2 conjugating enzyme
8. The assay of paragraph 1, wherein the probe comprises a detectable label or means of generating a detectable signal.
9. The assay of any of paragraphs 1-8, wherein the mutation in the RING domain results in C39A or C64A amino acid change in the BRCA1 protein.
10. The assay of any of paragraphs 1-9, wherein the mutation in the RING domain is selected from any one or a combination of the following mutations: M18, C24R, I26A, T37, C39A, C39Y, C44F/G, C44F, I31M, L51A, C61G, C64A, C64Y, T73R, C44F or C47F/G.
11. The assay of any of paragraphs 1-10, wherein the mutation in the BRCT domain results in G1656D, T1700A, R1699Q, R1699W, M1775R, M1775K, R1835P or E1836K amino acid change in the BRCA1 protein.
12. The assay of any of paragraphs 1-11, wherein the topoisomerase I inhibitor is as camptothecin (CPT), or CPT analogues such as topotecan and irinotecan and derivatives thereof.
13. A computer system for determining if a subject with cancer has a probability of being responsive to a topoisomerase I inhibitor, the system comprising:
   i. a measuring module configured to detect the presence of at least one mutation in the RING domain and/or BRCT domain of the BRCA1 gene, wherein the mutation in the RING domain and/or BRCT domain decreases the binding affinity of the BRCA1 protein for the phosphorylated serine 10 topoisomerase protein or decreases the E3 ligase activity of BRCA1 and/or decreases the binding affinity of BRCA1 for BARD1 and/or a E2 conjugating enzyme;
   ii. a storage module configured to store output data from the measuring module;
   iii. a comparison module adapted to compare the data stored on the storage module with a reference sequence data of BRCA1 gene, and to provide a retrieved content, and
   iv. a display module for displaying whether there is the presence or absence of at least one mutation in the RING domain and/or BRCT domain of the BRCA1 gene, wherein the mutation in the RING domain and/or BRCT domain decreases the binding affinity of the BRCA1 protein for the phosphorylated serine 10 topoisomerase protein or decreases the E3 ligase activity of BRCA1 and/or decreases the binding affinity of BRCA1 for BARD1 and/or a E2 conjugating enzyme and/or displaying the identity of the mutations in the RING domain and/or BRCT domain measured present in the biological sample.
14. The system of 13, wherein if the comparison module determines the presence of a mutation in the RING domain and/or BRCT domain which decreases the binding affinity of the BRCA1 protein with any of (i) BARD1, (ii) any BRCA1 E2 conjugating enzyme, or (ii) phosphorylated serine 10 topoisomerase I protein or decreases the ubiquitination of the phosphorylated serine 10 topoisomerase I protein in the biological sample obtained from a subject, the display module displays a positive signal indicating that the subject is likely to be responsive to a topoisomerase I inhibitor, as compared to a subject who does not have the presence of said mutations.

15. The system of any of paragraphs 13-14, wherein if the comparison module determines the absence of a mutation in the RING domain and/or BRCT domain which decreases the binding affinity of the BRCA1 protein for the phosphorylated serine 10 topoisomerase I protein or decreases the ubiquitination of the phosphorylated serine 10 topoisomerase I protein in the biological sample obtained from a subject, the display module displays a negative signal indicating the subject is likely to be unresponsive to a topoisomerase I inhibitor.

16. The system of any of paragraphs 13-15, further comprising creating a report based on the presence or absence of a mutation in the RING domain and/or BRCT domain which decreases the binding affinity of the BRCA1 protein for the phosphorylated serine 10 topoisomerase I protein or decreases the ubiquitination of the phosphorylated serine 10 topoisomerase I protein.

17. An assay to identify variances in the BRCT domain which decrease the binding affinity of BRCT domain of the BRCA1 protein for the phospho-ser10-topoisomerase I protein, the assay comprising:
    i. contacting a BRCT domain protein comprising a mutation with a topoisomerase I phosphopeptide comprising a detectable signal;
    ii. measuring the level of detectable signal from topoisomerase I phosphopeptide,
    iii. comparing the measured detectable signal with a reference detectable signal, wherein the reference detectable signal is from the interaction of a wild-type BRCT domain without the mutation with the same topoisomerase I phosphopeptide,
    iv. wherein a decreased detectable signal from the mutant BRCT domain as compared to a reference detectable signal indicates the mutation decreases the binding affinity of the BRCT domain for the phospho-ser10-topoisomerase I protein.

18. The assay of paragraph 17, wherein the topoisomerase I phosphopeptide comprise SEQ ID NO: 1 or SEQ ID NO: 4 or a functional fragment thereof.

19. The assay of paragraph 17, wherein the BRCT domain protein comprises amino acids 1650-1865 of BRCA1 protein of SEQ ID NO: 6, or a functional fragment thereof.

20. The assay of paragraph 17, wherein the detectable label is a fluorescent label.

21. The assay of paragraph 17, wherein the BRCT domain protein is immobilized to a solid support.

22. The assay of paragraph 17, wherein the assay is a fluorescent polarization assay.

23. An assay to identify variances in the RING domain which decrease the ubiquitination of phospho-ser10-topoisomerase I protein, the assay comprising:
    1. contacting a RING domain protein comprising a mutation with a topoisomerase I phosphopeptide comprising a detectable signal;
    2. measuring the level of detectable signal from topoisomerase I phosphopeptide,
    ii. comparing the measured detectable signal with a reference detectable signal, wherein the reference detectable signal is from the interaction of a wild-type RING domain without the mutation with the same topoisomerase I phosphopeptide,
    1. wherein a decreased detectable signal from the mutant RING domain as compared to a reference detectable signal indicates the mutation decreases the ubiquitination of phospho-ser10-topoisomerase I protein.

24. The assay of paragraph 23, wherein the topoisomerase I phosphopeptide comprise SEQ ID NO: 1 or SEQ ID NO: 4 or a functional fragment thereof.

25. The assay of paragraph 23, wherein the RING domain protein comprises amino acids 1-109 of BRCA1 protein of SEQ ID NO: 6, or a functional fragment thereof.

26. The assay of paragraph 23, wherein the detectable label is a fluorescent label.

27. The assay of paragraph 23, wherein the RING domain protein is immobilized to a solid support.

28. The assay of paragraph 23, wherein the assay is a fluorescent polarization assay.

29. An assay to identify agents which decrease the binding affinity of the BRCA1 protein for the phospho-ser10-topoisomerase I protein, comprising
    a. contacting a phosphorylated ser10-topoisomerase I protein, or a functional fragment thereof with test compound in the presence of a BRCT domain protein and ubiquitin comprising a detectable label;
    b. measuring the level of detectable signal from the ubiquitin,
    c. comparing the measured detectable signal with a reference detectable signal, wherein the reference detectable signal is from the absence of the test compound,
    d. wherein a decreased detectable signal as compared to a reference detectable signal indicates the test compound decreases the binding affinity BRCA1 protein for the phospho-ser10-topoisomerase I protein.

30. An assay to identify agents which inhibit the interaction of the BRCA1 protein with the phospho-ser10-topoisomerase I protein, comprising
    a. contacting a phosphorylated ser10-topoisomerase I protein, or a functional fragment thereof with at least one test compound in the presence of a BRCT domain protein and ubiquitin comprising a detectable label;
    b. measuring the level of detectable signal from the ubiquitin,
    c. comparing the measured detectable signal with a reference detectable signal, wherein the reference detectable signal is from the absence of the test compound,
    d. wherein a decreased detectable signal as compared to a reference detectable signal indicates the test compound decreases the interaction of the BRCA1 protein with the phospho-ser10-topoisomerase I protein.

31. The assay of paragraph 29 or 30, wherein the BRCT domain protein and ubiquitin comprising a detectable label is incubated with the test compound prior to contacting with the BRCT domain protein.

32. The assay of paragraph 29 or 30, wherein the BRCT domain comprises amino acids 1650-1865 of BRCA1 protein of SEQ ID NO: 6, or a functional fragment thereof.

33. The assay of any of paragraphs 29 to 32, wherein the BRCT domain is immobilized directly or indirectly on a solid support.

34. The assay of any of paragraphs 29 to 33, wherein the topoisomerase I protein is immobilized directly or indirectly on a solid support.

35. The assay of any of paragraphs 29 to 34, wherein the topoisomerase I protein is phosphorylated by DNA-PK.

36. The assay of any of paragraphs 29 to 35, wherein the topoisomerase I protein is phosphorylated by DNA-PK prior to contacting with the test compound, BRCT domain protein and ubiquitin comprising a detectable label.

37. An assay for selecting therapy for a cancer having cancer, the assay comprising:
   a. subjecting a biological sample from the subject to a genotyping assay to determine at least one or a combination of the following mutations:
      i. a mutation in the BRCT domain which decreases the binding affinity of the BRCA1 protein for the phosphorylated serine 10 topoisomerase protein;
      ii. a mutation in the RING domain which decreases the E3 ligase activity of BRCA1;
      iii. a mutation in the RING domain which decreases the binding affinity of BRCA1 for BARD1; or
      iv. a mutation in the RING domain which decrease the binding affinity of BRCA1 for an E2 conjugating enzyme.
   b. detecting the determine at least one or a combination of the following mutations:
      i. a mutation in the BRCT domain which decreases the binding affinity of the BRCA1 protein for the phosphorylated serine 10 topoisomerase protein;
      ii. a mutation in the RING domain which decreases the E3 ligase activity of BRCA1;
      iii. a mutation in the RING domain which decreases the binding affinity of BRCA1 for BARD1; or
      iv. a mutation in the RING domain which decrease the binding affinity of BRCA1 for an E2 conjugating enzyme.
   c. selecting a topo isomerase inhibitor for the subject when there is a mutation in the BRCT domain which decreases the binding affinity of the BRCA1 protein for the phosphorylated serine 10 topoisomerase protein or a mutation in the RING domain which decreases the E3 ligase activity of BRCA1, or a mutation in the RING domain which decreases the binding affinity of BRCA1 for BARD1; or a mutation in the RING domain which decrease the binding affinity of BRCA1 for an E2 conjugating enzyme; and selecting a non-topoisomerase inhibitor when there is not the presence of a mutation in the BRCT domain which decreases the binding affinity of the BRCA1 protein for the phosphorylated serine 10 topoisomerase protein or a mutation in the RING domain which decreases the E3 ligase activity of BRCA1, or a mutation in the RING domain which decreases the binding affinity of BRCA1 for BARD1; or a mutation in the RING domain which decrease the binding affinity of BRCA1 for an E2 conjugating enzyme.

38. The assay of paragraph 37, wherein at least one mutation in the RING domain and/or BRCT domain of the BRCA1 results in at least a 10% decrease the binding affinity of the BRCA1 protein for the phosphorylated serine 10 topoisomerase protein or results in at least a 10% decrease in the E3 ligase activity of BRCA1 and/or results in at least a 10% decrease in the binding affinity of BRCA1 for BARD1 and/or a E2 conjugating enzyme as compared to a wild type BRCA1 gene identifies a subject who would be predicted to benefit from the treatment of a topoisomerase inhibitor.

39. The assay of paragraph 37, wherein at least one mutation in the RING domain and/or BRCT domain of the BRCA1 results in a statistically significant decrease the binding affinity of the BRCA1 protein for the phosphorylated serine 10 topoisomerase protein or results in a statistically significant decrease in the E3 ligase activity of BRCA1 and/or results in a statistically significant decrease in the binding affinity of BRCA1 for BARD1 and/or a E2 conjugating enzyme as compared to a wildtype BRCA1 gene identifies a subject who would be predicted to benefit from the treatment of a topoisomerase inhibitor.

40. The assay of paragraph 39, wherein the statistically significant decrease is a decrease of at least one standard deviation.

41. The assay of paragraph 39, wherein the statistically significant decrease is a decrease of at least two standard deviation.

42. The assay of paragraph 39, further comprising the step of treating a subject with the selected therapy.

43. The assay of any of paragraphs 37-42, wherein the mutation in the RING domain is selected from any one or a combination of the following mutations: M18, C24R, I26A, T37, C39A, C39Y, C44F/G, C44F, I31M, L51A, C61G, C64A, C64Y, T73R, C44F or C47F/G.

44. The assay of any of paragraphs 37-42, wherein the mutation in the BRCT domain results in G1656D, T1700A, R1699Q, R1699W, M1775R, M1775K, R1835P or E1836K amino acid change in the BRCA1 protein.

45. The assay of any of paragraphs 37-44, wherein the topoisomerase I inhibitor is as camptothecin (CPT), or CPT analogues such as topotecan and irinotecan and derivatives thereof.

46. A method for selecting a topo isomerase therapy for a subject having cancer comprising:
   a. subjecting a biological sample from the subject to a genotyping assay to determine at least one or a combination of the following mutations:
      i. a mutation in the BRCT domain which decreases the binding affinity of the BRCA1 protein for the phosphorylated serine 10 topoisomerase protein;
      ii. a mutation in the RING domain which decreases the E3 ligase activity of BRCA1;
      iii. a mutation in the RING domain which decreases the binding affinity of BRCA1 for BARD1; or
      iv. a mutation in the RING domain which decrease the binding affinity of BRCA1 for an E2 conjugating enzyme.
   b. selecting a topo isomerase inhibitor for the subject when there is a mutation in the BRCT domain which decreases the binding affinity of the BRCA1 protein for the phosphorylated serine 10 topoisomerase protein or a mutation in the RING domain which decreases the E3 ligase activity of BRCA1, or a mutation in the RING domain which decreases the binding affinity of BRCA1 for BARD1; or a mutation in the RING domain which decrease the binding affinity of BRCA1 for an E2 conjugating enzyme; and selecting a non-topoisomerase inhibitor when there is not the presence of a mutation in the BRCT domain which decreases the binding affinity of the BRCA1 protein for the phosphorylated serine 10 topoisomerase protein or a mutation in the RING domain which decreases the E3 ligase activity of BRCA1, or a mutation in the RING domain which decreases the binding affinity of BRCA1 for BARD1; or a mutation in the RING domain which decrease the binding affinity of BRCA1 for an E2 conjugating enzyme.

47. The method of paragraph 46, wherein at least one mutation in the RING domain and/or BRCT domain of the BRCA1 that results in at least a 10% decrease the binding affinity of the BRCA1 protein for the phosphorylated serine 10 topoisomerase protein or at least a 10% decrease in the E3 ligase activity of BRCA1 and/or at least a 10% decrease in the binding affinity of BRCA1 for BARD1 and/or a E2 conjugating enzyme as compared to a wild type BRCA1 gene identifies a subject who would be predicted to benefit from the treatment of a topoisomerase inhibitor.

48. The method of paragraph 46, wherein at least one mutation in the RING domain and/or BRCT domain of the BRCA1 results in a statistically significant decrease the binding affinity of the BRCA1 protein for the phosphorylated serine 10 topoisomerase protein or results in a statistically significant decrease in the E3 ligase activity of BRCA1 and/or results in a statistically significant decrease in the binding affinity of BRCA1 for BARD1 and/or a E2 conjugating enzyme as compared to a wildtype BRCA1 gene identifies a subject who would be predicted to benefit from the treatment of a topoisomerase inhibitor.

49. The method of paragraph 48, wherein the statistically significant decrease is a decrease of at least one standard deviation.

50. The method of paragraph 48, wherein the statistically significant decrease is a decrease of at least two standard deviations.

51. The method of paragraph any of 46-50, further comprising the step of treating a subject with the selected therapy.

52. The method of paragraph any of 46-51, wherein the mutation in the RING domain is selected from any one or a combination of the following mutations: M18, C24R, I26A, T37, C39A, C39Y, C44F/G, C44F, I31M, L51A, C61G, C64A, C64Y, T73R, C44F or C47F/G.

53. The method of paragraph any of 46-51, wherein the mutation in the BRCT domain results in G1656D, T1700A, R1699Q, R1699W, M1775R, M1775K, R1835P or E1836K amino acid change in the BRCA1 protein.

54. The method of paragraph any of 46-53, wherein the topoisomerase I inhibitor is as camptothecin (CPT), or CPT analogues such as topotecan and irinotecan and derivatives thereof.

EXAMPLES

The examples presented herein relate to the methods, kits, machines and computer systems and media to identify the presence of mutations in BRCA1 which interfere with the degradation of phosphorylated topoisomerase I polypeptide in a biological sample, and where a mutation is present in the BRAC1 gene which interferes or inhibits the BRCA1 interaction (via the BRCT domain) with the phospho-topo I protein, it indicates the subject from whom the sample was obtained is likely to be responsive to topo I inhibitors such as, for example but not limited to camptothecin (CPT), or CPT analogues such as topotecan and irinotecan and derivatives thereof. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Example 1

BRCA1 Mutations in RING and BRCT Domain Effecting E3 Ligase Activity Will Determine Response to Topoisomerase I (TopoI) Inhibitors-Camptothecin and their Analogues (CPTs) Used for Cancer Therapy.

Mechanism:

Topo I is ubiquitinated and degraded in the response to CPTs by UPP. The rate of topo I degradation determines the CPT response. The inventors have previously discovered that BRCA1 is the E3 ligase for topo I and plays critical role in topo I degradation in the response to CPTs. Additionally, the inventors have previously discovered that that BRCA1 binds directly to topo I by BRCA1-BRCT domain and ubiquitinates by RING domain.

Several mutations have been reported both in RING and BRCT domain (Serena L Clark et al, Comput. Struct. Biotechnol. J: Jun. 21, 2012). The inventors have determined that any mutation in RING domain (e.g., any mutation located within amino acids 1-109 of BRCA1 protein, e.g., SEQ ID NO: 6) that impairs or inhibits or interrupts the BRCA1 E3 ligase function will sensitize the tumor for CPT. In some embodiments, the mutation include, but are not limited to, C39A and C64A (Peter S Brzovic; J. Biol. Chem. 2001:276 (44) 41399-41406.

Similarly, the inventors have determined that any mutation in the BRCT domain (e.g., any mutation located within amino acids 1650-1863 of the BRCA1 protein, e.g., SEQ ID NO: 6) that disrupts or impairs the binding of BRAC1 to phosphorylated topo I will reduce the topo I degradation and identify the subject whom carries the mutation to be tumor sensitive to cancer treatment with topo I inhibitors, e.g., CPTs. In some embodiments, such mutations include, but are not limited to R1699W, G1656D (Nicholas Coquelle et al; Biochemistry 2011, 50: 4579-4589).

Example 2

Figure 1C:
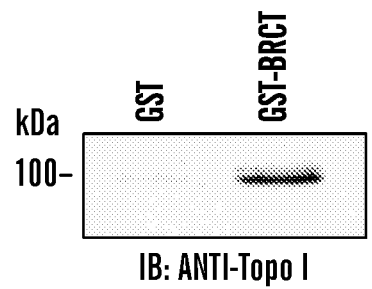
Figure 8:
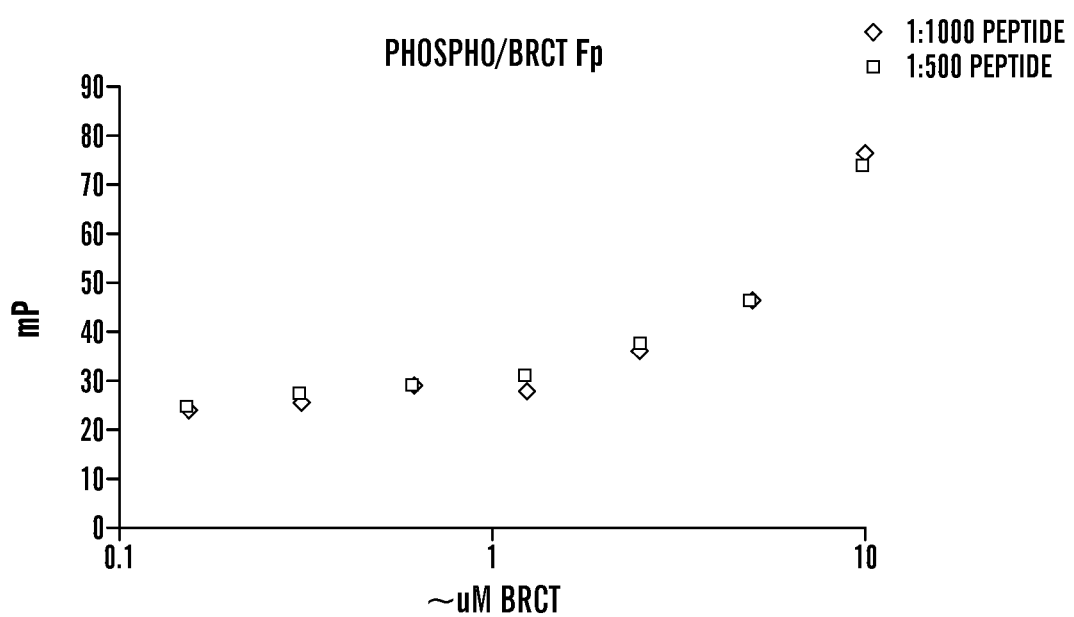
FIG. 8 shows fluorescence polarization (FP) of Topo I phosphopeptide interaction with GST-BRCT. Phosphopeptide labeled with Alexa Fluor 532 was incubated at a final dilution of either 1:1000 or 1:500 with varying concentrations of GST-BRCT or buffer alone. Polarization of the light emitted by the labeled peptide was detected on a Tecan Infinite M1000 pro and is plotted as a function of protein concentration. The increased polarization at higher concentrations indicates a direct interaction between protein and peptide, and appears to occur at concentrations consistent with those reported in the literature for other BRCT-interacting phosphopeptides. Further studies must be performed to demonstrate the specificity of this interaction.
Figure 9:
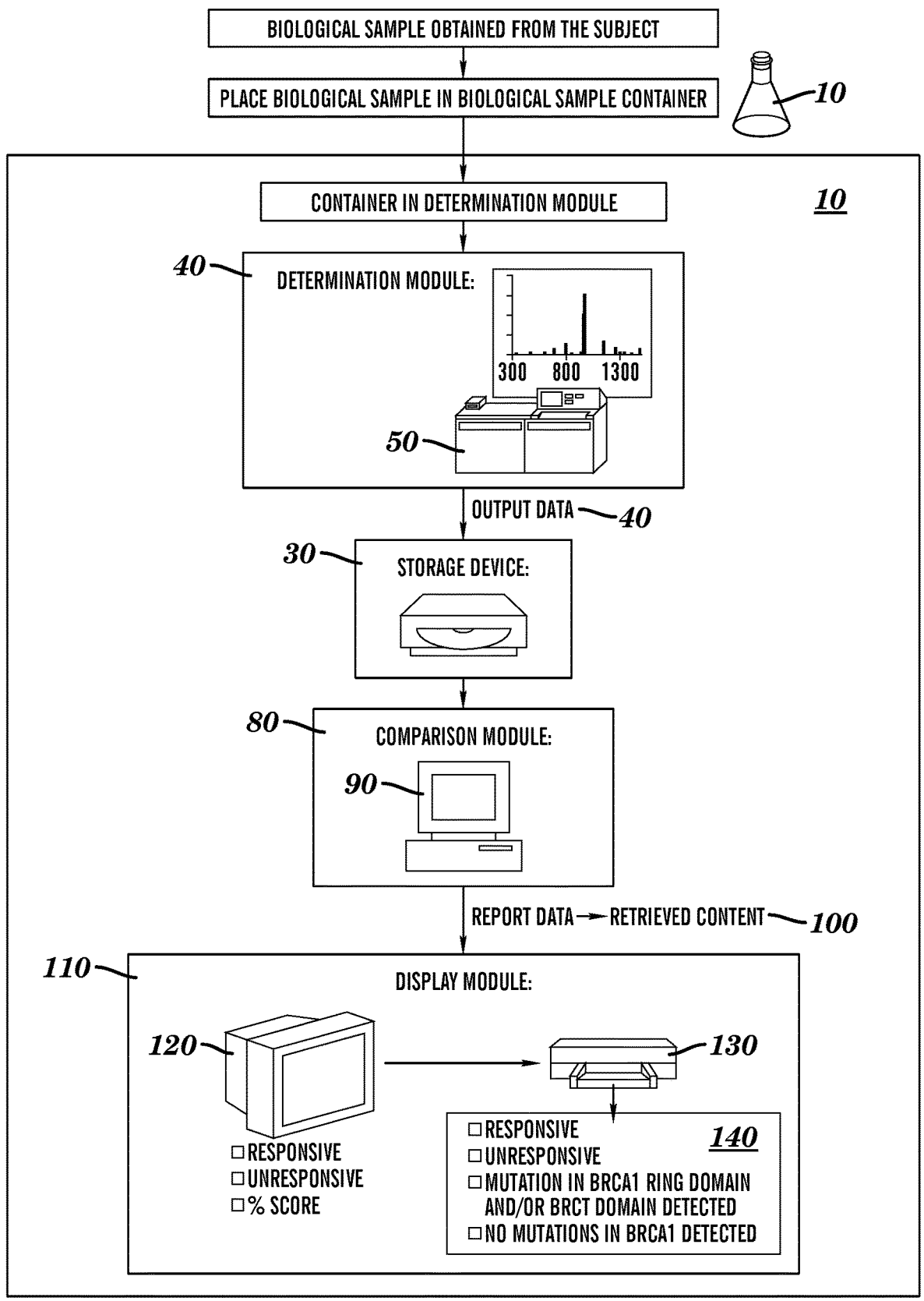
FIG. 9 shows a simplified block diagram of an embodiment of the present invention which relates to a machine for determining if a subject is responsive to a topo I inhibitor.
Figure 10:
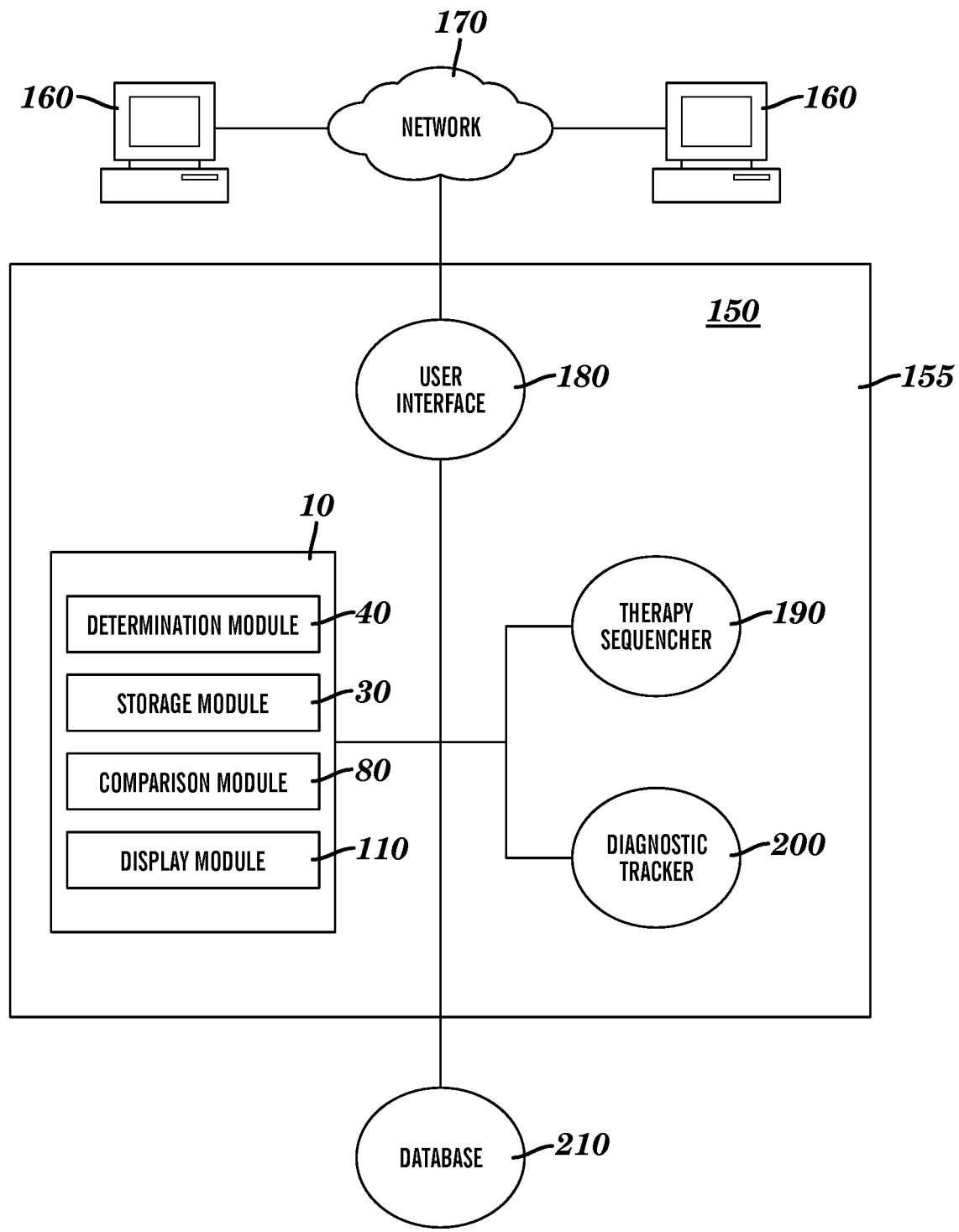
FIG. 10 of a machine 10 for determining if a subject is responsive to a topo I inhibitor according to an embodiment of the invention.
Figure 11:
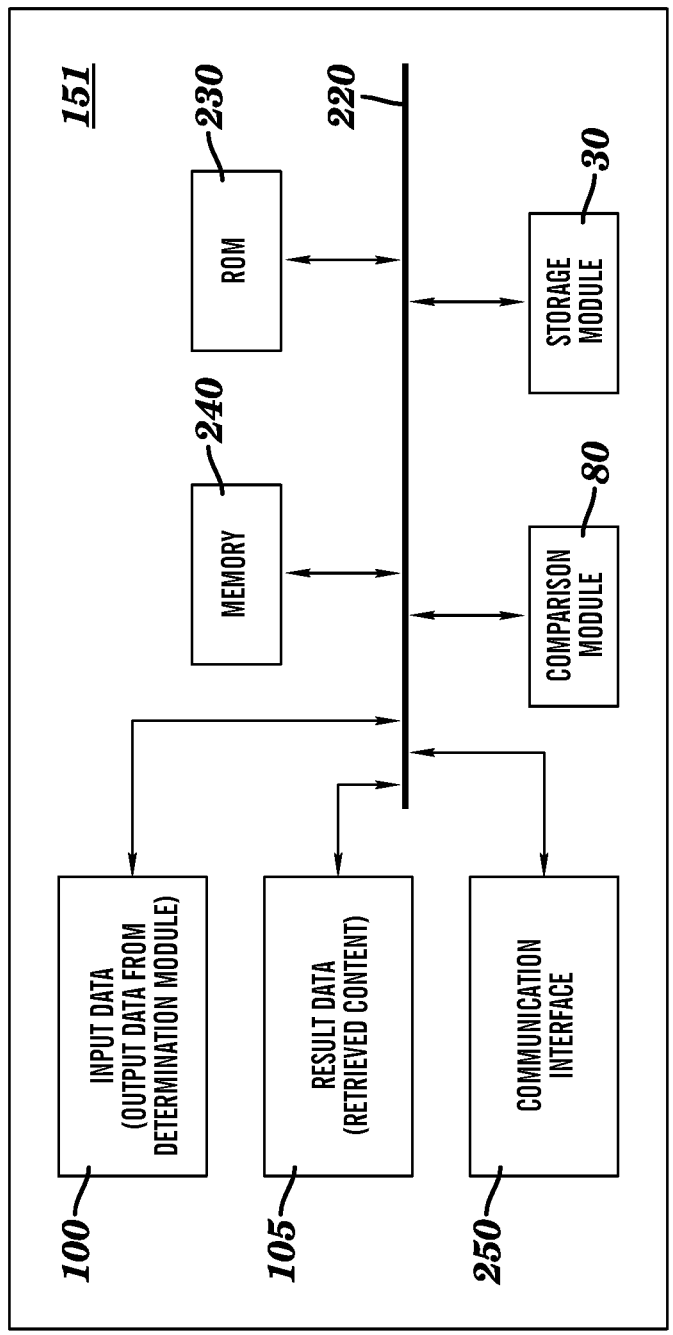
FIG. 11 depicts an exemplary block diagram of a computer system 151 that may be configured to execute the prognostic application 155 illustrated in FIG. 12.
Figure 12:
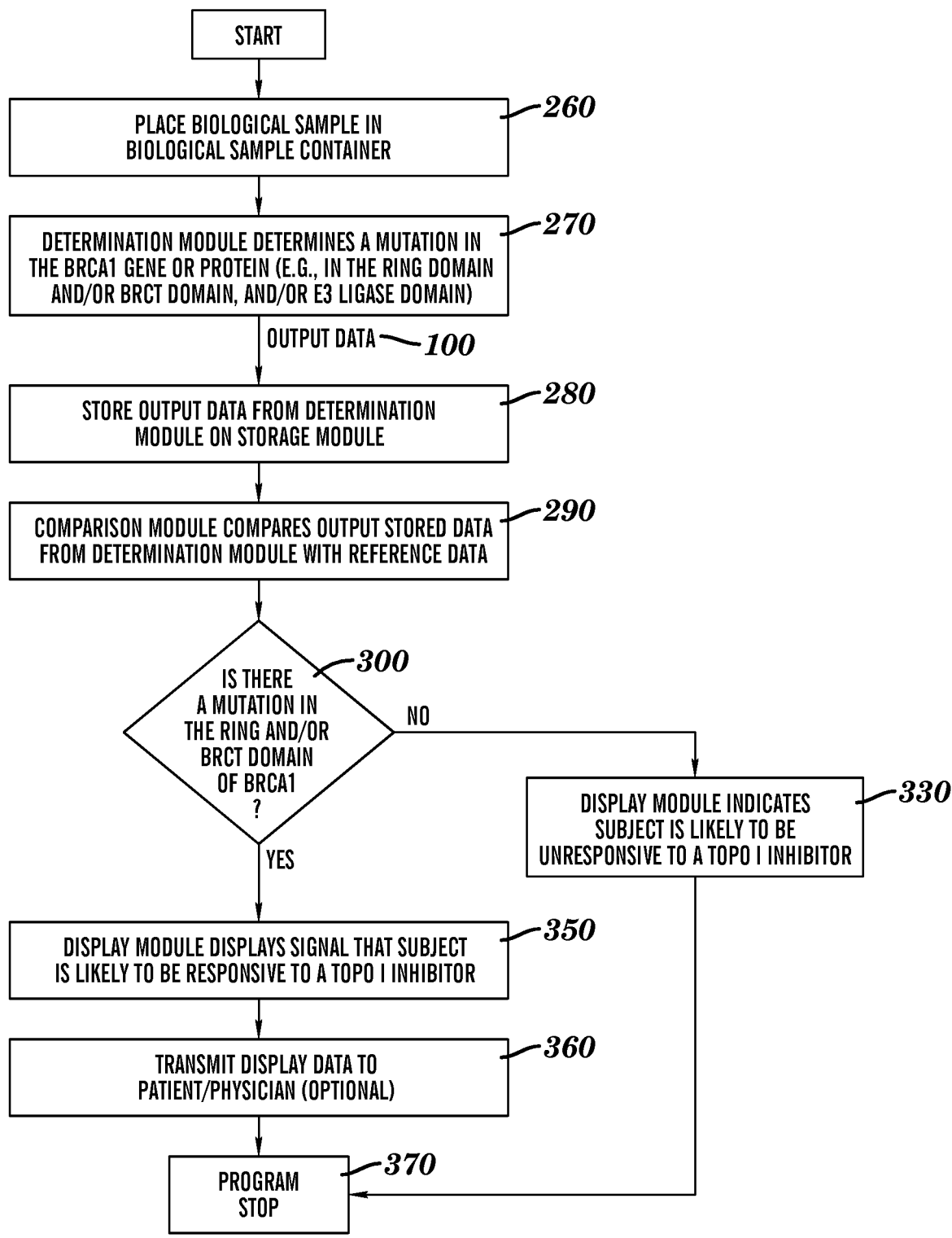
FIG. 12 shows a flow chart of a instructions for analyzing if a subject is responsive to a topo I inhibitor.

Topo I associates with BRCA1: Among the other topoI-associated proteins, the inventors identified the BRCT domain of BRCA1. BRCA1 is an E3 ligase, and binds to its substrates directly. To understand BRCA1 mediated ubiquitination of topoI, the inventors first determined if BRCA1 associates with topoI. Nuclei were isolated from HCT15 cells and nuclear extracts were prepared with high salt buffer (350 mM NaCl), salt concentration was then normalized to 150 mM. The nuclear extract was subjected to immunoprecipitation with anti-BRCA1 and immunoprecipitates were analyzed by immunoblot analysis with anti-topoI. Immunoblot analysis with topo I demonstrated that anti-BRCA1 immunoprecipitates contain topo I (FIG. 1A). In a reciprocal experiment, nuclear extract HCT cells were subjected to immunoprecipitation with anti-topoI. The immunoprecipitates were analyzed by immunoblot with anti-BRCA1 (FIG. 1B). The results demonstrate that BRCA1 immunoprecipitates with topoI, indicating an association between these two proteins. Mouse (FIG. 1A) and Rabbit IgG (FIG. 1B) were also subjected to immunoprecipitation as control. The immunoprecipitation experiments determined that topoI- BRCA1 associates in a complex. Several BRCA1 E3 ligase substrates have been identified. The studies have also shown that BRCA1 binds directly to its E3 ligase. To determine whether topo I directly bind to BRCA1, GST-BRCT domain was incubated with purified topoI. After extensive wash the adsorbates were analyzed by immunoblot analysis with anti-topoI. GST sepharose beads were also incubated with purified topoI. The results demonstrate that topo I bind directly with BRCA1-BRCT domain (FIG. 1C). The inventors demonstrate with florescence polarization data that topo I phosphopeptide with phosphorylates S10 binds directly to BRCA1-BRCT domain (see FIG. 8).

Figure 2A:
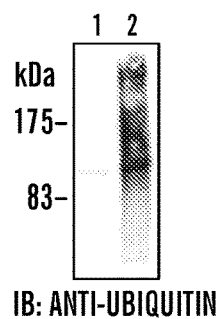
FIG. 2A-2D shows BRCA1 ubiquitinates topo I in vitro and in cells

BRCA1 ubiquitinates topo I in vitro in cells: BRCA1 is an enzyme with E3 ubiquitin ligase activity. To determine if topo I is ubiquitinated by BRCA1 in the response to CPT induced DNA-DSB, the inventors first used highly purified assay to determine if BRCA1 ubiquitinates topoI. GST-topo I attached to glutathione sepharose was incubated with BRCA1 heterodimer in the presence of ubiquitination buffer and ATP. The reaction was carried out at 37° C. for one hour. After extensive wash, glutathione sepharose beads were re-suspended in SDS-PAGE loading buffer and analyzed by immunoblot analysis with anti-ubiquitin. In the control reaction, no BRCA1 was added. The inventors demonstrated that topo I is ubiquitinated by BRCA1 (FIG. 2A).

Figure 2B:
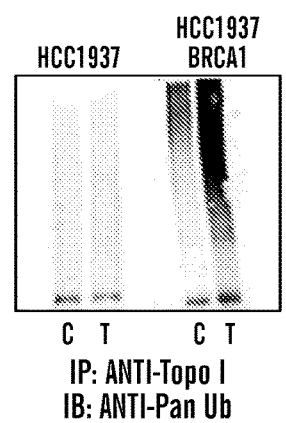
Figure 2C:
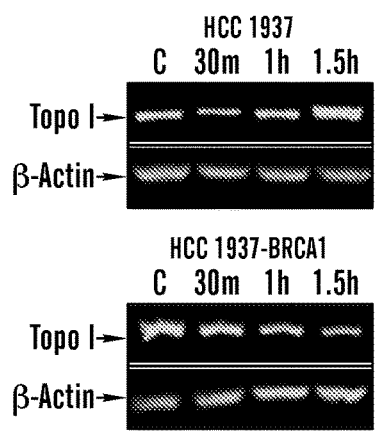
Figure 2D:
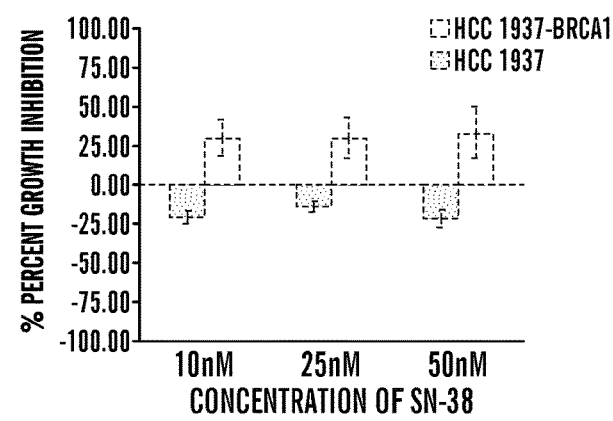

To further validate the findings in cells the inventors used BRCA1 E3 ligase deficient HCC1937 cells. The cells are sensitive to DNA-damaging agents and have impaired BRCA1 E3 ligase function. The inventors have used HCC1937 cells and stably expressed BRCA1 (HCC1937-BRCA1) to restore E3 ligase function. Both, HCC1937 and HCC1937-BRCA1 cells were treated with CPT for 60 minutes and drug free for 30 minutes in the presence of MG132. Control and CPT treated cells were lysed and subjected to immunoprecipitation with anti-topoI. The immunoprecipitates were analyzed by immunoblot analysis with anti-ubiquitin. No ubiquitination was observed in HCC1937 cells while pronounced topo I ubiquitination was observed in HCC1937-BRCA1 cells, particularly in cells treated with SN-38 (FIG. 2B). Topo I is degraded in the response to CPT by ubiquitin proteosomal pathways, and the rate of degradation at least in part determines anti neoplastic activity of the drug. To determine the correlation between topo I degradation and CPT efficacy in HCC1937 and HCC1937-BRCA cells, were treated with N-38 and topo I degradation (FIG. 2C) and cell growth inhibition assays were performed (FIG. 2D). Herein, the inventors have demonstrated that HCC1937-BRCA1 cells degrade topo I in the response to SN-38 and these cells are sensitive to the drug. In contrast, HCC1937 do not degrade topo I by UPP and these cells are sensitive to SN38 (FIG. 2D).

Figure 13A:
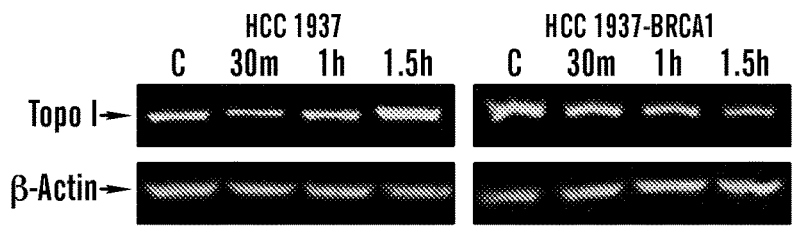
FIG. 13A-13C shows cancer cells with deficient BRCA1-E3 ligase function due to mutation in BRCA1 gene, fails to ubiquitinate and degrade topo I in the response to CPT and these cells are sensitive to CPT.
Figure 13B:
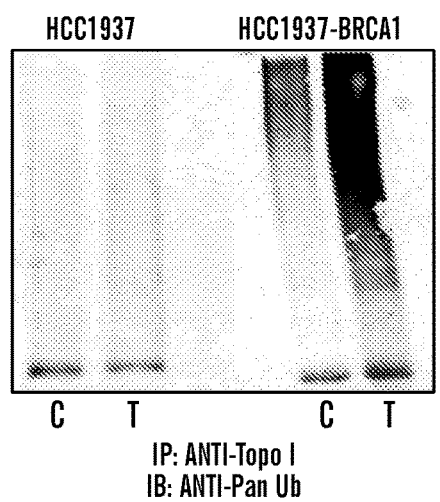
Figure 13C:
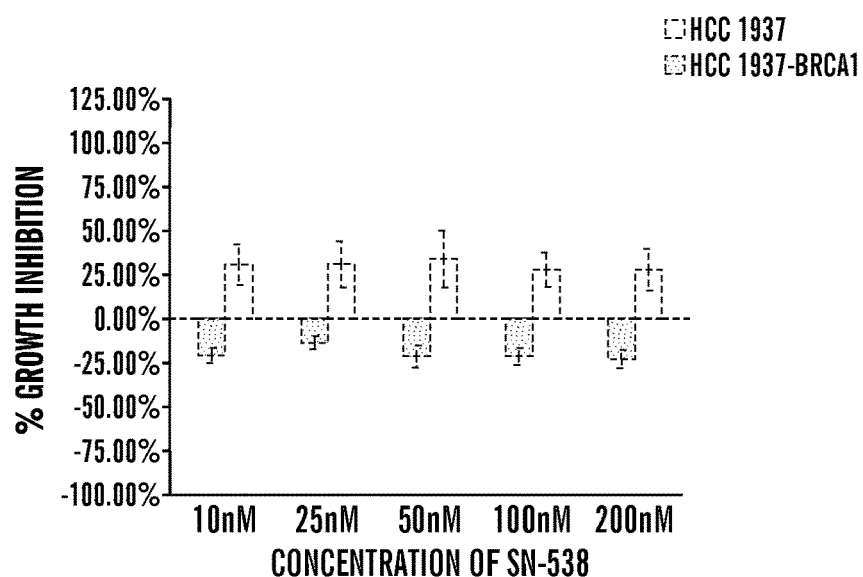

Additionally, as shown in FIGS. 13A-13D, the BRCA1 E3 ligase function is essential to ubiquitinate and degrade topo I in the response to CPT. Accordingly, any mutation that impairs BRCA1 E3 ligase function and thus results in the failure of BRCA1 to ubiquitinate and degrade topoI. Furthermore, BRCA1 E3 ligase deficient cells that fail to ubiquitinate topo I are highly sensitive to CPT, in contrast cells with WT BRCA1 that degrades topo I in the response to CPT are resistant to this drug (FIG. 13C).

Ubiquitination Mediated Topo I Degradation Determines CPT Response in TNBC Cells.

Figure 3C:
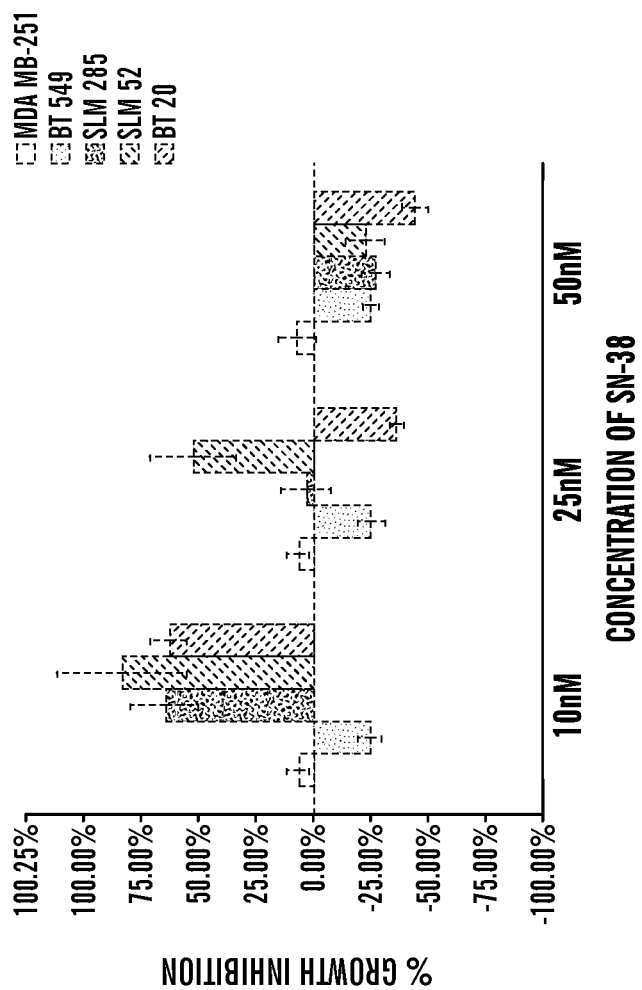
Figure 4B:
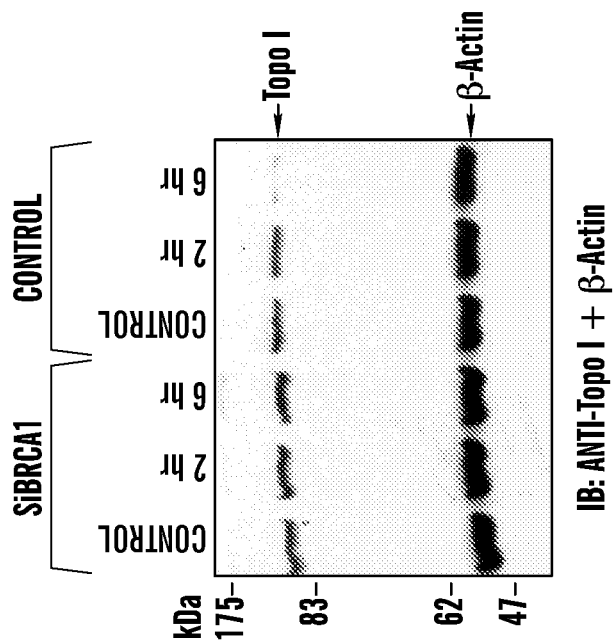
FIGS. 4A-4C shows BRCA1 dependent ubiquitination and proteosomal degradation of topo I in BT 474 cells.
Figure 4A:
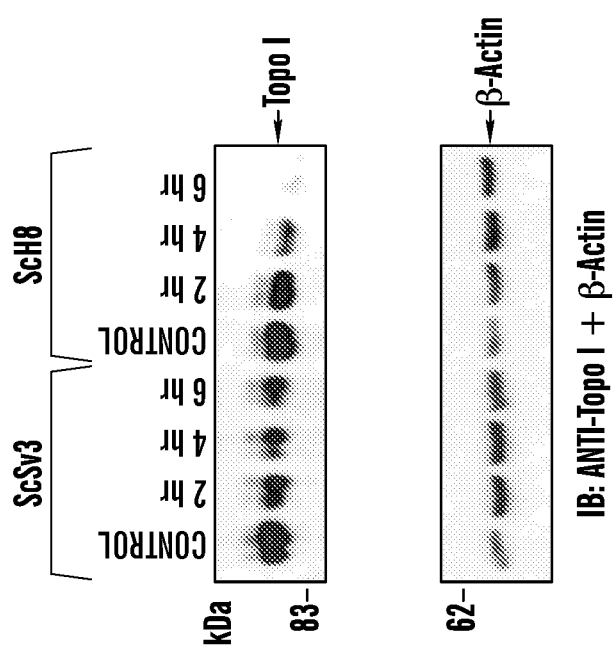
Figure 4C:
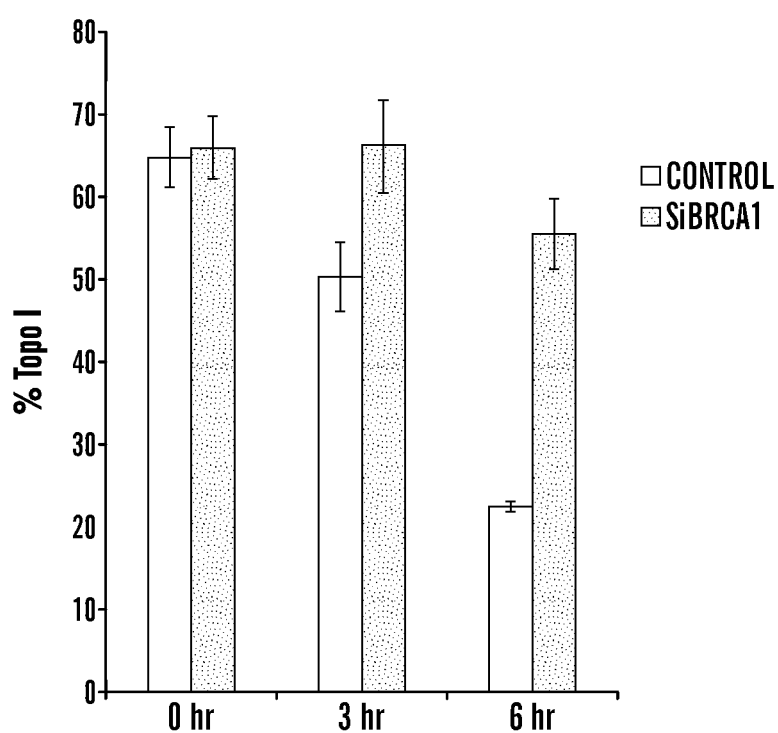
Figure 5B:
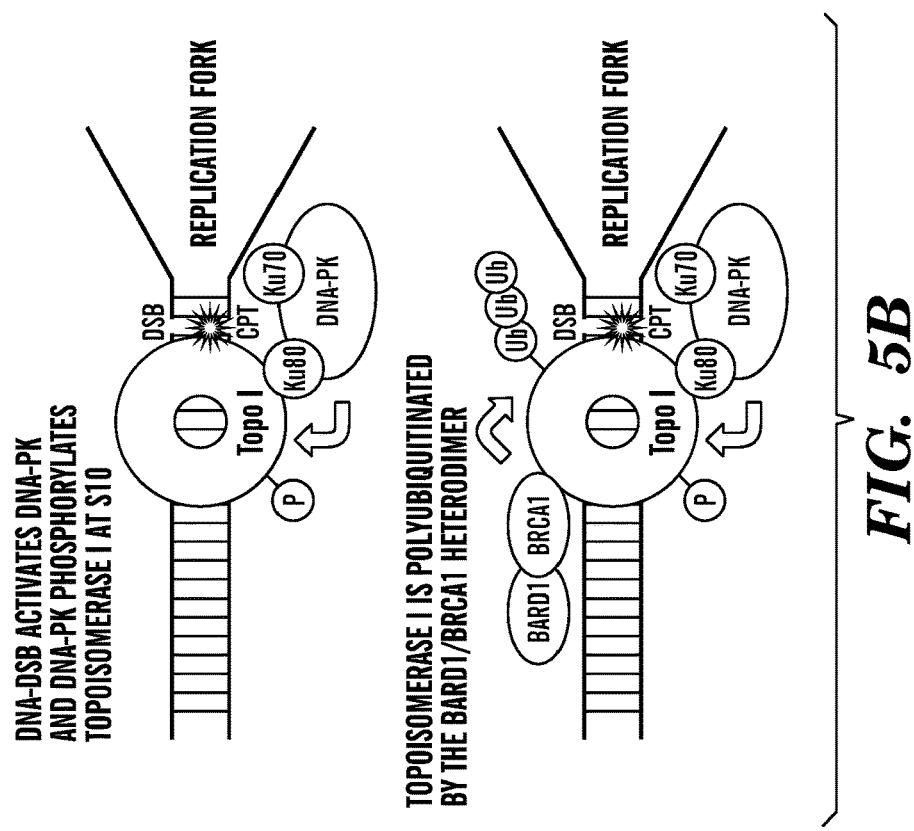
FIGS. 5A-5C show a schematic diagram showing the fate of cellular topo I in the response to anti cancer drug (CPT) treatment. It has been established that topo I is degraded by ubiquitination in the response to CPT. DNA-TopoI-CPT makes cleavage complex during S phase.
Figure 5A:
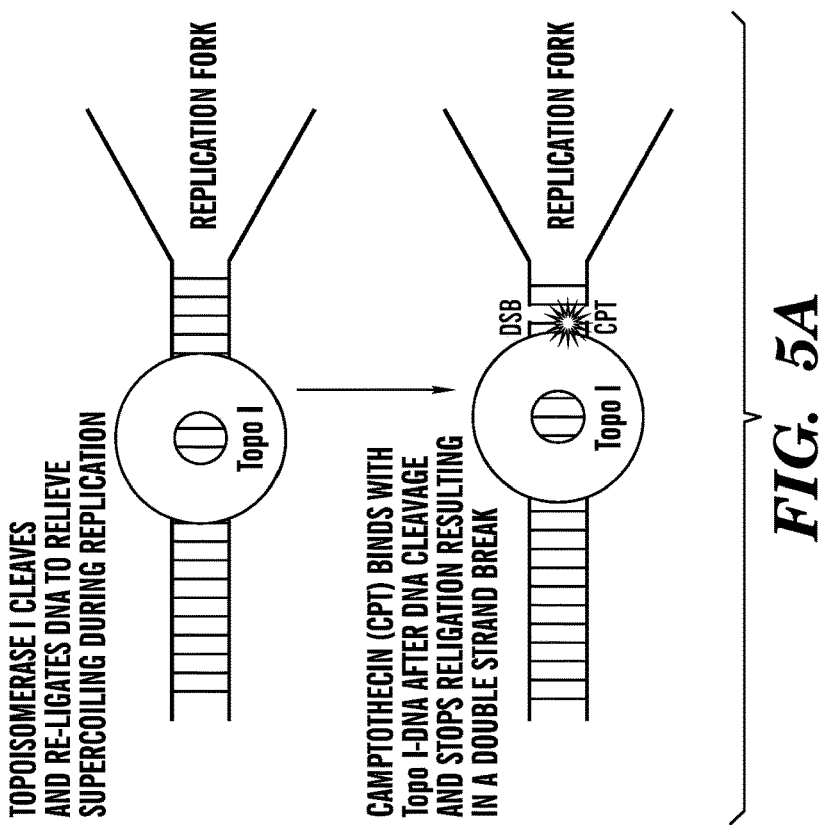
Figure 5C:
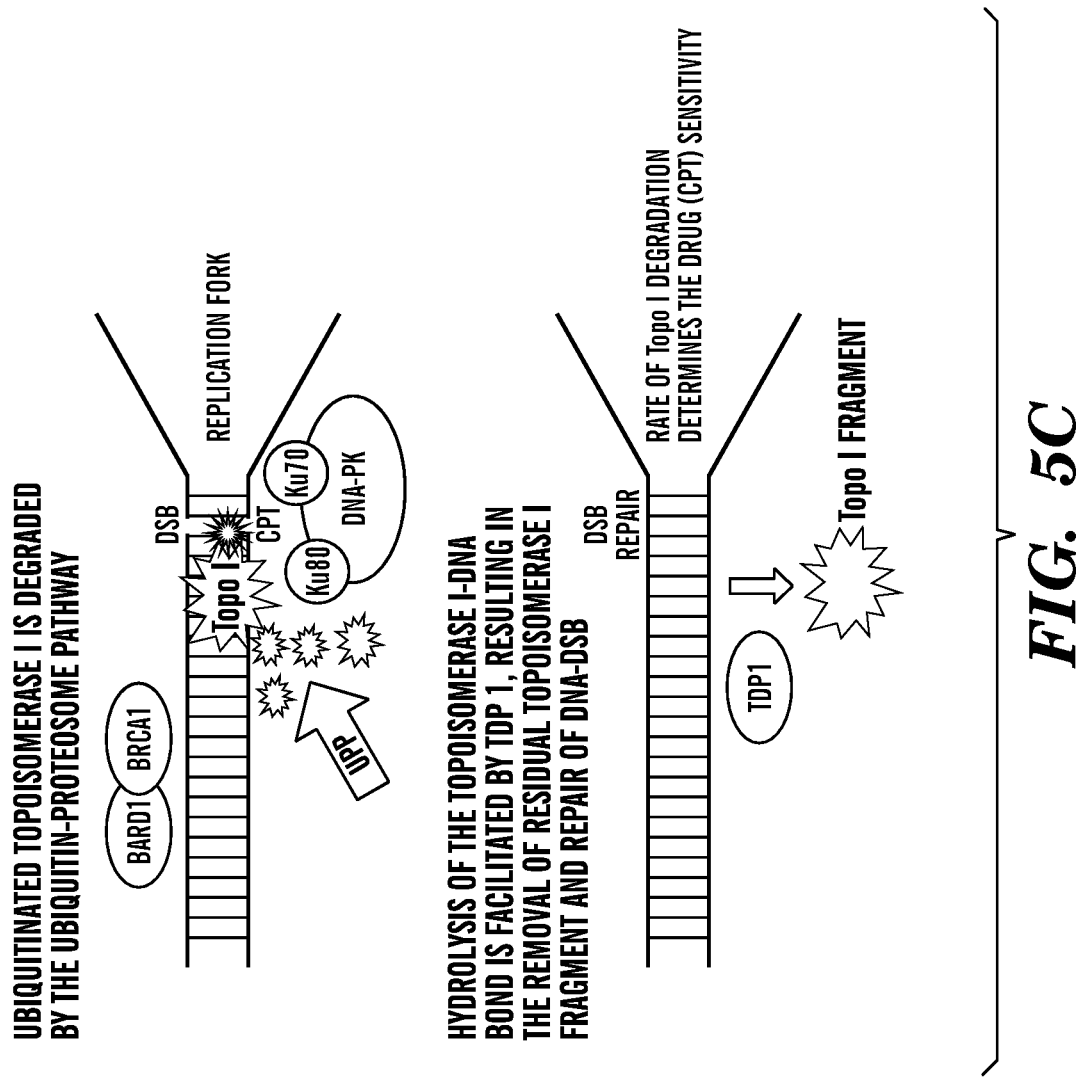

To understand the topo I ubiquitination and CPT response, based on the inventors previous early screen, the inventors selected four triple negative breast cancer cell lines with differential rate of UPP mediated topo I degradation. Topo I was degraded within 2 hours in response to CPT in MDAMB231 and SUM52 cells while in BT20 and BT549 topo I was not appreciably degraded in 2 hours (FIG. 3A). To determine the level of CPT induced ubiquitination, control and treated cells were lysed and cell lysates were subjected to immunoprecipitation with anti-topoI. The immunoprecipitates were analyzed by immunoblot analysis with anti-ubiquitin. The results demonstrate that topo I is ubiquitinated only on MDAMB231 and SUM52 cell, in contrast no ubiquitination was observed in BT20 and BT549 cells in the response to CPT (FIG. 3B). To understand the possible correlation between ubiquitination dependent topo I degradation and CPT response, cells were treated with different concentration of SN-38 and analyzed for percent growth inhibition. SUM52 cells degrade topo I rapidly and growth inhibition was least in these cells at 10 and 25 nM concentration. MDAMB231 remained resistant to the drug and cells were growing even at 50 nM concentration. Contrary to these two cell lines BT2020 and BT549 were very sensitive to the drug. The highest percent of growth inhibition was detected in BT20 (FIG. 3C). Taken together, rate of topo I degradation by UPP determines the drug sensitivity in triple negative breast cancer cells.

Example 3

Drug Screening Protocol to Disrupt topoisomeraseI-BRCA1 Interaction for CPT Sensitization: Two Distinctly Different Methods have been Developed GST-Fusion Protein Based Method:

The inventors have developed a high throughput-screen to identify agents and candidate test compounds which interrupt the binding of BRCA1 protein with the phosphor-ser10-topoisomerase I protein. In some embodiments, the high throughput-screen to identifies agents and candidate test compounds which decrease the binding affinity the BRCT domain of BRCA1 protein for the phospho-ser10-topoisomerase I protein.

The inventors have demonstrated herein an assay and method for high-throughput screening (HTS) of candidate molecules to identify compounds which interfere with the BRCA1-phospho-ser10 topo I polypeptide interaction. In some embodiments, an assay comprises a topo I polypeptide or a functional fragment thereof, which is phosphorylated on serine 10 (S10) by DNA-PK kinase, then incubated with a ubiquitin mixture comprising a BRCT domain of BRCA1, or a functional fragment thereof, pre-incubated with at least one test compound, where a decrease in fluorescence as compared to a negative control or absence of a test compound indicates that the test compound decreases the interaction of BRCT domain with the phosphor-S10-topo I protein. Such a compound is thus useful to be used in conjunction or in combination with a topo I inhibitor, e.g., CPT or analogues thereof to increase the efficacy of the topo I inhibitor in the treatment of cancer.

Figure 6:
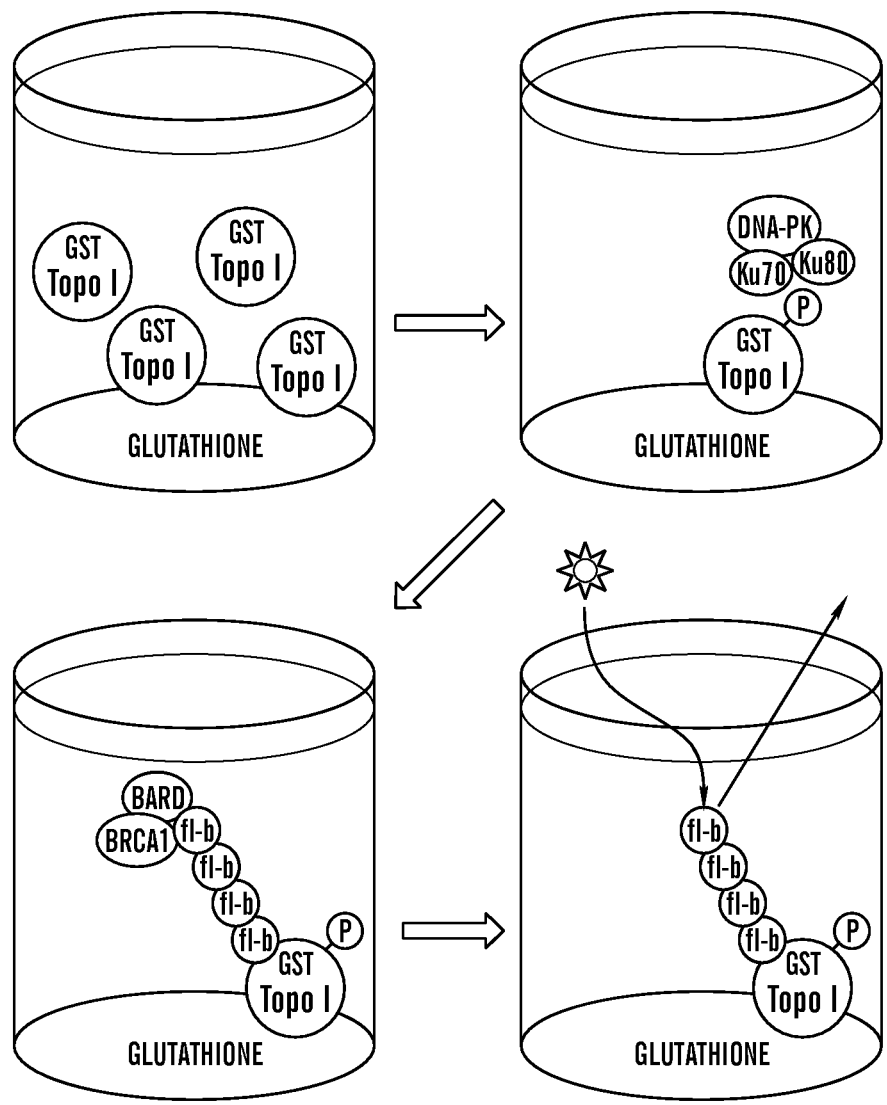
FIG. 6 is a schematic of in-vitro ubiquitination High through-put (HTS) assay. GST (control) and GST-Topo I are immobilized in 96-well format at saturating concentrations. DNA-PK is used to phosphorylate the protein in the well. Next, a fluorescein-tagged ubiquitin mixture, which has been pre-incubated with library compounds or DMSO control, is added to the wells and allowed to react. Finally, the plate is washed thoroughly and ubiquitination of the protein is detected by a fluorescence plate reader.
Figure 7:
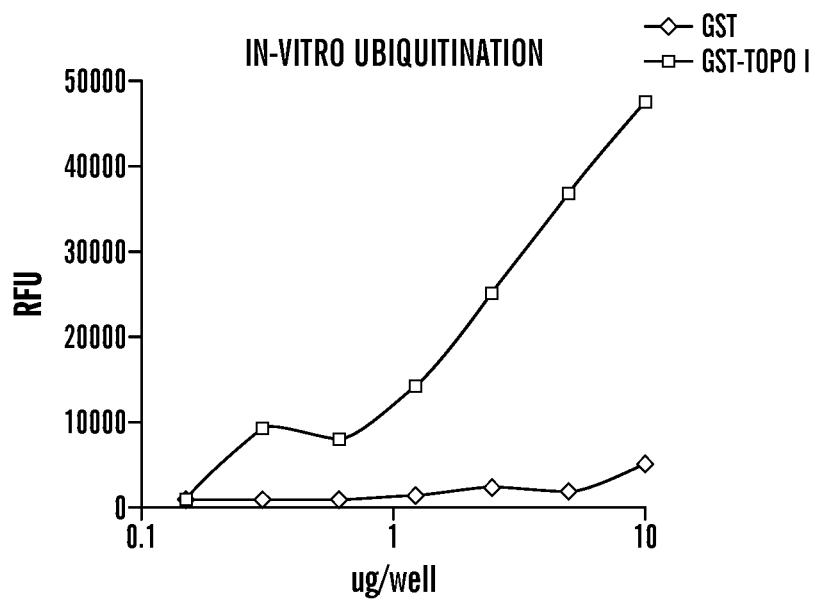
FIG. 7 shows the results of the in vitro ubiquitination HTS assay.

An exemplary method and assay is shown in FIG. 6 and was performed as follows; GST and GST-Topo I were expressed in Rosetta (DE3) pLysS competent *E. Coli* (Novagen) and purified by standard methods. Protein was eluted from the beads, dialyzed against TBS containing 1 mM DTT and 5% glycerol, and stored at −80° at a concentration of 2 mg/ml. The day prior to screening, both proteins were diluted to 40 μM in TBS containing 0.05% Tween20, 1 mM DTT, and protease inhibitor tablets (Roche), and plated at 50 μl/well in black 96-well glutathione coated plates (Pierce), which were then incubated overnight at 4° with gentle shaking. The protein dilution was aspirated from the plates, and the plates were washed 3 times in TBST. A phosphorylation mixture (20 mM Tris 7.4, 10 mM MgCl2, 10 mM MnCl2, 0.5 µg/ml DNA-PK (Invitrogen), 50 µg/ml Salmon Sperm DNA (Agilent), and 30 µM ATP) was added at 50 µl/well and incubated at 37° for 1 hour. During this incubation period, the ubiquitination reaction was prepared for pre-incubation with screening compounds by transferring 16.5 µl of 26% S-100 extract from HeLa cells in Hepes 7.4 containing 2 µM Ubiquitin aldehyde and 2 µM MG-132 (R&D Systems) to each well of a 96-well polypropylene plate, then supplementing with 11 ul of 100 µM library compound or 10% DMSO for control wells. The compounds were pre-incubated for 15 minutes at room temperature before completion of the reaction mixture with an equal volume of 2 µM fluorescein-tagged ubiquitin (R&D Systems), 3.75 mM MgCl2, and 1.5 mM ATP. The ubiquitin reaction was mixed and then transferred to the assay plate at 50 µl/well after removal of the phosphorylation reaction. The plates were incubated for another 2 hours at 37° before being washed 4 times in TBST, and ubiquitination of the proteins was detected by reading the fluorescence signal on a Tecan Infinite M1000 pro (EX 490 nm, EM 515 nm). The effect of the test compound on ubiquitination can be assessed where a decrease in florescence indicates the decrease in binding of the BRCT domain with the phospho-ser10-topo I protein (see FIG. 7).

Screening data were analyzed and archived by the Collaborative Drug Discovery database (Burlingame, Calif. www.collaborativedrug.com).

Example 4

Fluorescence Polarization

The inventors herein have used a fluorescent polarization assay to identify mutations in the BRCT domain and/or RING domain of BRCA1 gene which decrease the binding affinity of the BRCA1 protein for the phosphor-ser10-topo I protein and/or decrease ubiquitination of the phosphor-ser10-topo I protein. The inventors incubated a fluorescent phosphopeptide of topo I (e.g., SEQ ID NO: 1 or SEQ ID NO:4) with a BRCT domain or fragment thereof which comprises the mutation, and assessed the binding affinity of the BRCT domain with the mutation in comparison with the binding affinity of the wild-type BRCT domain. In some embodiments the binding affinity of different protein concentrations of the BRCT domain (e.g., from 20 nM to 500 microM) is evaluated with a constant concentration of the topo I phosphopeptide (e.g., 1:1000, or 1:500, or 50 nM or 100 nM) in a reaction volume of 20 microliters. The fluorescence is recorded and a polarization change is plotted against the log of a protein concentration, and a Kd determined from the resulting curve. A mutation in the BRCT domain which decreases the fluorescence as compared to the fluorescence measured with the wild-type BRCT domain identifies a mutation in the BRCT domain which interferes with the BRCA1 protein interaction with the phosphor-ser10-topo I protein.

An exemplary assay to identify a mutation in the BRCT domain which decreases the binding affinity of the BRCT domain for the phospho-ser10-topo I polypeptide was performed as follows (see FIG. 8): Topo I phosphopeptide NDpSQIEADFRLNDC (SEQ ID NO: 4) was conjugated to Alexa Fluor 532 (Invitrogen) via maleimide reaction with the C-terminal cysteine, as per manufacturer's protocol. Labeled peptide was separated from the reaction mixture by RP-HPLC using C-18 media and eluted with 30% acetonitrile. The partially purified peptide was lyophilized and resuspended in TBS with 1 mM DTT. GST-BRCT was expressed in Rosetta (DE3) pLysS (Novagen) and purified by standard methods. The purified protein was eluted from the GS beads and dialyzed against TBS containing 1 mM DTT and 5% glycerol prior to storage at −80°. On the day of the assay, GST-BRCT aliquots were thawed on ice and serially diluted 1:1 in TBS-1 mM DTT-0.01% Tween20 for a total of 7 concentrations plus one buffer blank in 90 µl final. Labeled peptide was diluted at either 1:100 or 1:50 and then added to the protein dilutions at 10 µl/well (final peptide dilution of 1:1000 or 1:500, 50-100 nM). 20 µl from each dilution was then transferred to each of 4 wells in a 384-well black plate, and FP was read on a Tecan Infinite M1000 pro and plotted as mP as a function of protein concentration.

REFERENCES

All references cited herein in the specification and examples are incorporated herein in their entirety by reference.

Serena L Clark et al, Comput. Struct. Biotechnol. J: Jun. 21, 2012

Nicholas Coquelle et al; Biochemistry 2011, 50: 4579-4589

The invention claimed is:

1. A method for treating a subject with cancer comprising:
   a. using a set of primers to (i) amplify a portion of the nucleic acid of SEQ ID NO: 5 that encodes amino acids 1-109 of SEQ ID NO: 6 (the RING domain of BRCA1) and/or (ii) to amplify a portion of the nucleic acid of SEQ ID NO: 5 that encodes amino acids 1650-1863 of SEQ ID NO: 6 (BRCT domain of the BRCA1) from a biological sample obtained from a subject with cancer to produce amplified nucleic acids;
   b. sequencing the amplified nucleic acids and comparing said sequence with the nucleic acid of SEQ ID NO: 5 that encodes amino acids 1-109 of SEQ ID NO: 6 or the nucleic acid of SEQ ID NO: 5 that encodes amino acids 1650-1863 of SEQ ID NO: 6 and detecting if a mutation is present;
   c. selecting the subject with cancer to be treated with a topoisomerase I inhibitor where a mutation in nucleic acid of SEQ ID NO: 5 that encodes amino acids 1-109 of SEQ ID NO: 6 or a mutation in nucleic acid of SEQ ID NO: 5 that encodes amino acids 1650-1863 of SEQ ID NO: 6 is detected, and
   d. administering a topoisomerase I inhibitor to the subject with cancer selected in step c.

2. The method of claim 1, wherein the mutation in the RING domain of the BRCA1 gene is selected from any one or a combination of the following mutations: C24R, I26A, C39A, C39Y, C44F/G, C44F, I31M, L51A, C61G, C64A, T73R, C44F and C47F/G.

3. The method of claim 1, wherein the mutation in the BRCT domain of the BRCA1 gene is selected from any one or a combination of the following mutations:
   G1656D, T1700A, R1699Q, R1699W, M1775K, R1835P and E1836K.

4. The method of claim 1, wherein the topoisomerase I inhibitor is camptothecin (CPT), topotecan or irinotecan.

5. The method of claim 1, wherein the mutation in the nucleic acid of SEQ ID NO: 5 results in a change of any one or more amino acids of: 18, 24, 26, 37, 39, 44, 47, 31, 51, 61, 73, 1656, 1700, 1835 and 1836 of the amino acid sequence of SEQ ID NO:6.

* * * * *

SEQUENCE LISTING

```
<160> NUMBER OF SEQ ID NOS: 6

<210> SEQ ID NO 1
<211> LENGTH: 17
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated Ser

<400> SEQUENCE: 1

Met Ser Gly Asp His Leu His Asn Asp Ser Gln Ile Glu Ala Asp Phe
1               5                   10                  15

Arg

<210> SEQ ID NO 2
```

```
<211> LENGTH: 765
<212> TYPE: PRT
<213> ORGANISM: Homo sapiens

<400> SEQUENCE: 2
```

| | | | | | | | | | | | | | | |
|---|---|---|---|---|---|---|---|---|---|---|---|---|---|---|
|Met|Ser|Gly|Asp|His|Leu|His|Asn|Asp|Ser|Gln|Ile|Glu|Ala|Asp|Phe|
|1| | | |5| | | | |10| | | | |15| |

Arg Leu Asn Asp Ser His Lys His Lys Asp Lys His Lys Asp Arg Glu
            20                  25                  30

His Arg His Lys Glu His Lys Lys Glu Lys Asp Arg Lys Ser Lys
        35                  40                  45

His Ser Asn Ser Glu His Lys Asp Ser Glu Lys Lys His Lys Glu Lys
50                  55                  60

Glu Lys Thr Lys His Lys Asp Gly Ser Ser Glu Lys His Lys Asp Lys
65                  70                  75                  80

His Lys Asp Arg Asp Lys Glu Lys Arg Lys Glu Glu Lys Val Arg Ala
                85                  90                  95

Ser Gly Asp Ala Lys Ile Lys Lys Glu Lys Glu Asn Gly Phe Ser Ser
                100                 105                 110

Pro Pro Gln Ile Lys Asp Glu Pro Glu Asp Asp Gly Tyr Phe Val Pro
            115                 120                 125

Pro Lys Glu Asp Ile Lys Pro Leu Lys Arg Pro Arg Asp Glu Asp Asp
    130                 135                 140

Ala Asp Tyr Lys Pro Lys Lys Ile Lys Thr Glu Asp Thr Lys Lys Glu
145                 150                 155                 160

Lys Lys Arg Lys Leu Glu Glu Glu Asp Gly Lys Leu Lys Lys Pro
                165                 170                 175

Lys Asn Lys Asp Lys Asp Lys Val Pro Glu Pro Asp Asn Lys Lys
            180                 185                 190

Lys Lys Pro Lys Lys Glu Glu Glu Gln Lys Trp Lys Trp Trp Glu
        195                 200                 205

Glu Arg Tyr Pro Glu Gly Ile Lys Trp Lys Phe Leu Glu His Lys Gly
                210                 215                 220

Pro Val Phe Ala Pro Pro Tyr Glu Pro Leu Pro Glu Asn Val Lys Phe
225                 230                 235                 240

Tyr Tyr Asp Gly Lys Val Met Lys Leu Ser Pro Lys Ala Glu Glu Val
                    245                 250                 255

Ala Thr Phe Phe Ala Lys Met Leu Asp His Glu Tyr Thr Thr Lys Glu
                260                 265                 270

Ile Phe Arg Lys Asn Phe Phe Lys Asp Trp Arg Lys Glu Met Thr Asn
            275                 280                 285

Glu Glu Lys Asn Ile Ile Thr Asn Leu Ser Lys Cys Asp Phe Thr Gln
        290                 295                 300

Met Ser Gln Tyr Phe Lys Ala Gln Thr Glu Ala Arg Lys Gln Met Ser
305                 310                 315                 320

Lys Glu Glu Lys Leu Lys Ile Lys Glu Glu Asn Glu Lys Leu Leu Lys
                325                 330                 335

Glu Tyr Gly Phe Cys Ile Met Asp Asn His Lys Glu Arg Ile Ala Asn
                340                 345                 350

Phe Lys Ile Glu Pro Pro Gly Leu Phe Arg Gly Arg Gly Asn His Pro
            355                 360                 365

Lys Met Gly Met Leu Lys Arg Arg Ile Met Pro Glu Asp Ile Ile Ile
        370                 375                 380

Asn Cys Ser Lys Asp Ala Lys Val Pro Ser Pro Pro Gly His Lys

```
            385                 390                 395                 400
    Trp Lys Glu Val Arg His Asp Asn Lys Val Thr Trp Leu Val Ser Trp
                    405                 410                 415

Thr Glu Asn Ile Gln Gly Ser Ile Lys Tyr Ile Met Leu Asn Pro Ser
                420                 425                 430

Ser Arg Ile Lys Gly Glu Lys Asp Trp Gln Lys Tyr Glu Thr Ala Arg
            435                 440                 445

Arg Leu Lys Lys Cys Val Asp Lys Ile Arg Asn Gln Tyr Arg Glu Asp
        450                 455                 460

Trp Lys Ser Lys Glu Met Lys Val Arg Gln Arg Ala Val Ala Leu Tyr
    465                 470                 475                 480

Phe Ile Asp Lys Leu Ala Leu Arg Ala Gly Asn Glu Lys Glu Glu Gly
                    485                 490                 495

Glu Thr Ala Asp Thr Val Gly Cys Cys Ser Leu Arg Val Glu His Ile
                500                 505                 510

Asn Leu His Pro Glu Leu Asp Gly Gln Glu Tyr Val Val Glu Phe Asp
            515                 520                 525

Phe Leu Gly Lys Asp Ser Ile Arg Tyr Tyr Asn Lys Val Pro Val Glu
        530                 535                 540

Lys Arg Val Phe Lys Asn Leu Gln Leu Phe Met Glu Asn Lys Gln Pro
    545                 550                 555                 560

Glu Asp Asp Leu Phe Asp Arg Leu Asn Thr Gly Ile Leu Asn Lys His
                    565                 570                 575

Leu Gln Asp Leu Met Glu Gly Leu Thr Ala Lys Val Phe Arg Thr Tyr
                580                 585                 590

Asn Ala Ser Ile Thr Leu Gln Gln Gln Leu Lys Glu Leu Thr Ala Pro
            595                 600                 605

Asp Glu Asn Ile Pro Ala Lys Ile Leu Ser Tyr Asn Arg Ala Asn Arg
        610                 615                 620

Ala Val Ala Ile Leu Cys Asn His Gln Arg Ala Pro Pro Lys Thr Phe
    625                 630                 635                 640

Glu Lys Ser Met Met Asn Leu Gln Thr Lys Ile Asp Ala Lys Lys Glu
                    645                 650                 655

Gln Leu Ala Asp Ala Arg Arg Asp Leu Lys Ser Ala Lys Ala Asp Ala
                660                 665                 670

Lys Val Met Lys Asp Ala Lys Thr Lys Lys Val Val Glu Ser Lys Lys
            675                 680                 685

Lys Ala Val Gln Arg Leu Glu Glu Gln Leu Met Lys Leu Glu Val Gln
        690                 695                 700

Ala Thr Asp Arg Glu Glu Asn Lys Gln Ile Ala Leu Gly Thr Ser Lys
    705                 710                 715                 720

Leu Asn Tyr Leu Asp Pro Arg Ile Thr Val Ala Trp Cys Lys Lys Trp
                    725                 730                 735

Gly Val Pro Ile Glu Lys Ile Tyr Asn Lys Thr Gln Arg Glu Lys Phe
                740                 745                 750

Ala Trp Ala Ile Asp Met Ala Asp Glu Asp Tyr Glu Phe
            755                 760                 765

<210> SEQ ID NO 3
<211> LENGTH: 3600
<212> TYPE: DNA
<213> ORGANISM: Homo sapiens

<400> SEQUENCE: 3
```

```
caaatgcgaa cttaggctgt tacacaactg ctggggtctg ttctcgccgc ccgcccggca      60
gtcaggcagc gtcgccgccg tggtagcagc ctcagccgtt tctggagtct cgggcccaca     120
gtcaccgccg cttacctgcg cctcctcgag cctccggagt ccccgtccgc ccgcacaggc     180
cggttcgccg tctgcgtctc ccccacgccg cctcgcctgc cgccgcgctc gtccctccgg     240
gccgacatga gtggggacca cctccacaac gattcccaga tcgaagcgga tttccgattg     300
aatgattctc ataaacacaa agataaacac aaagatcgag aacaccggca caagaacac      360
aagaaggaga aggaccggga aaagtccaag catagcaaca gtgaacataa agattctgaa     420
aagaaacaca aagagaagga gaagaccaaa cacaaagatg gaagctcaga aaagcataaa     480
gacaaacata aagacagaga caaggaaaaa cgaaaagagg aaaaggttcg agcctctggg     540
gatgcaaaaa taagaaggaa gaaggaaaat ggcttctcta gtccaccaca aattaaagat     600
gaacctgaag atgatggcta ttttgttcct cctaaagagg atataaagcc attaaagaga     660
cctcgagatg aggatgatgc tgattataaa cctaagaaaa ttaaaacaga agataccaag     720
aaggagaaga aaagaaaact agaagaagaa gaggatggta aattgaaaaa acccaagaat     780
aaagataaag ataaaaaagt tcctgagcca gataacaaga aaaagaagcc gaagaaagaa     840
gaggaacaga agtggaaatg gtgggaagaa gagcgctatc ctgaaggcat caagtggaaa     900
ttcctagaac ataaaggtcc agtatttgcc ccaccatatg agcctcttcc agagaatgtc     960
aagtttatt atgatggtaa agtcatgaag ctgagcccca agcagagga agtagctacg    1020
ttctttgcaa aaatgctcga ccatgaatat actaccaagg aaatatttag gaaaaatttc    1080
tttaaagact ggagaaagga aatgactaat gaagagaaga atattatcac caacctaagc    1140
aaatgtgatt ttacccagat gagccagtat ttcaaagccc agacggaagc tcggaaacag    1200
atgagcaagg aagagaaact gaaaatcaaa gaggagaatg aaaaattact gaaagaatat    1260
ggattctgta ttatggataa ccacaaagag aggattgcta acttcaagat agagcctcct    1320
ggacttttcc gtggccgcgg caaccacccc aagatgggca tgctgaagag acgaatcatg    1380
cccgaggata taatcatcaa ctgtagcaaa gatgccaagg ttccttctcc tcctccagga    1440
cataagtgga agaagtccg gcatgataac aaggttactt ggctggtttc ctggacagag    1500
aacatccaag gttccattaa atacatcatg cttaacccta gttcacgaat caagggtgag    1560
aaggactggc agaaatacga gactgctcgg cggctgaaaa aatgtgtgga caagatccgg    1620
aaccagtatc gagaagactg gaagtccaaa gagatgaaag tccggcagag agctgtagcc    1680
ctgtacttca tcgacaagct tgctctgaga gcaggcaatg aaaaggagga aggagaaaca    1740
gcggacactg tgggctgctg ctcacttcgt gtggagcaca tcaatctaca cccagagttg    1800
gatggtcagg aatatgtggt agagtttgac ttcctcggga aggactccat cagatactat    1860
aacaaggtcc ctgttgagaa acgagttttt aagaacctac aactatttat ggagaacaag    1920
cagcccgagg atgatctttt tgatagactc aatactggta ttctgaataa gcatcttcag    1980
gatctcatgg agggcttgac agccaaggta ttccgtacat acaatgcctc catcacgcta    2040
cagcagcagc taaaagaact gacagccccg gatgagaaca tcccagcgaa gatcctttct    2100
tataaccgtg ccaatcgagc tgttgcaatt cttttgtaacc atcagagggc accaccaaaa    2160
acttttgaga agtctatgat gaacttgcaa actaagattg atgccaagaa ggaacagcta    2220
gcagatgccc ggagagacct gaaaagtgct aaggctgatg ccaaggtcat gaaggatgca    2280
aagacgaaga aggtagtaga gtcaaagaag aaggctgttc agagactgga ggaacagttg    2340
atgaagctgg aagttcaagc cacagaccga gaggaaaata aacagattgc cctgggaacc    2400
```

| | |
|---|---:|
| tccaaactca attatctgga ccctaggatc acagtggctt ggtgcaagaa gtggggtgtc | 2460 |
| ccaattgaga agatttacaa caaaacccag cgggagaagt ttgcctgggc cattgacatg | 2520 |
| gctgatgaag actatgagtt ttagccagtc tcaagaggca gagttctgtg aagaggaaca | 2580 |
| gtgtggtttg ggaaagatgg ataaactgag cctcacttgc cctcgtgcct ggggagaga | 2640 |
| ggcagcaagt cttaacaaac caacatcttt gcgaaaagat aaacctggag atattataag | 2700 |
| ggagagctga gccagttgtc ctatggacaa cttatttaaa aatatttcag atatcaaaat | 2760 |
| tctagctgta tgatttgttt tgaattttgt ttttattttc aagagggcaa gtggatggga | 2820 |
| atttgtcagc gttctaccag gcaaattcac tgtttcactg aaatgtttgg attctcttag | 2880 |
| ctactgtatg caaagtccga ttatattggt gcgttttac agttagggtt ttgcaataac | 2940 |
| ttctatattt taatagaaat aaattcctaa actcccttcc ctctctccca tttcaggaat | 3000 |
| ttaaaattaa gtagaacaaa aaacccagcg cacctgttag agtcgtcact ctctattgtc | 3060 |
| atggggatca attttcatta aacttgaagc agtcgtggct ttggcagtgt tttggttcag | 3120 |
| acacctgttc acagaaaaag catgatggga aaatatttcc tgacttgagt gttccttttt | 3180 |
| aaatgtgaat ttttatttct ttttaattat tttaaaatat ttaaacctttt ttcttgatct | 3240 |
| taaagatcgt gtagattggg gttggggagg gatgaagggc gagtgaatct aaggataatg | 3300 |
| aaataatcag tgactgaaac cattttccca tcatcctttg ttctgagcat tcgctgtacc | 3360 |
| ctttaagata tccatctttt tctttttaac cctaatcttt cacttgaaag attttattgt | 3420 |
| ataaaaagtt tcacaggtca ataaacttag aggaaaatga gtatttggtc caaaaaaagg | 3480 |
| aaaaataatc aagattttag ggcttttatt ttttcttttg taattgtgta aaaaatggaa | 3540 |
| aaaaacataa aaagcagaat tttaatgtga agacattttt tgctataatc attagttta | 3600 |

<210> SEQ ID NO 4
<211> LENGTH: 14
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated Ser

<400> SEQUENCE: 4

Asn Asp Ser Gln Ile Glu Ala Asp Phe Arg Leu Asn Asp Cys
1               5                   10

<210> SEQ ID NO 5
<211> LENGTH: 7224
<212> TYPE: DNA
<213> ORGANISM: Homo sapiens

<400> SEQUENCE: 5

| | |
|---|---:|
| gtaccttgat ttcgtattct gagaggctgc tgcttagcgg tagccccttg gtttccgtgg | 60 |
| caacggaaaa gcgcgggaat tacagataaa ttaaaactgc gactgcgcgg cgtgagctcg | 120 |
| ctgagacttc ctggacgggg acaggctgt ggggtttctc agataactgg gcccctgcgc | 180 |
| tcaggaggcc ttcaccctct gctctgggta aagttcattg gaacagaaag aaatggattt | 240 |
| atctgctctt cgcgttgaag aagtacaaaa tgtcattaat gctatgcaga aaatcttaga | 300 |
| gtgtcccatc tgtctggagt tgatcaagga acctgtctcc acaaagtgtg accacatatt | 360 |
| ttgcaaattt gcatgctga acttctcaa ccagaagaaa gggccttcac agtgtccttt | 420 |
| atgtaagaat gatataacca aaaggagcct acaagaaagt acgagattta gtcaacttgt | 480 |

```
tgaagagcta ttgaaaatca tttgtgcttt tcagcttgac acaggtttgg agtatgcaaa    540
cagctataat tttgcaaaaa aggaaaataa ctctcctgaa catctaaaag atgaagtttc    600
tatcatccaa agtatgggct acagaaaccg tgccaaaaga cttctacaga gtgaacccga    660
aaatccttcc ttgcaggaaa ccagtctcag tgtccaactc tctaaccttg aactgtgag    720 aactctgagg acaaagcagc ggatacaacc tcaaaagacg tctgtctaca ttgaattggg    780
atctgattct tctgaagata ccgttaataa ggcaacttat tgcagtgtgg agatcaaga    840 attgttacaa atcacccctc aaggaaccag ggatgaaatc agtttggatt ctgcaaaaaa    900
ggctgcttgt gaattttctg agacggatgt aacaaatact gaacatcatc aacccagtaa    960
taatgatttg aacaccactg agaagcgtgc agctgagagg catccagaaa agtatcaggg   1020
tagttctgtt tcaaacttgc atgtggagcc atgtggcaca aatactcatg ccagctcatt   1080
acagcatgag aacagcagtt tattactcac taaagacaga atgaatgtag aaaaggctga   1140
attctgtaat aaaagcaaac agcctggctt agcaaggagc caacataaca gatgggctgg   1200
aagtaaggaa acatgtaatg ataggcggac tcccagcaca gaaaaaaagg tagatctgaa   1260
tgctgatccc ctgtgtgaga gaaaagaatg gaataagcag aaactgccat gctcagagaa   1320
tcctagagat actgaagatg ttccttggat aacactaaat agcagcattc agaaagttaa   1380
tgagtggttt tccagaagtg atgaactgtt aggttctgat gactcacatg atggggagtc   1440
tgaatcaaat gccaaagtag ctgatgtatt ggacgttcta aatgaggtag atgaatattc   1500
tggttcttca gagaaaatag acttactggc cagtgatcct catgaggctt taatatgtaa   1560
aagtgaaaga gttcactcca aatcagtaga gagtaatatt gaagacaaaa tatttgggaa   1620
aacctatcgg aagaaggcaa gcctccccaa cttaagccat gtaactgaaa atctaattat   1680
aggagcattt gttactgagc cacagataat acaagagcgt cccctcacaa ataaattaaa   1740
gcgtaaaagg agacctacat caggccttca tcctgaggat tttatcaaga agcagattt   1800 ggcagttcaa aagactcctg aaatgataaa tcagggaact aaccaaacgg agcagaatgg   1860
tcaagtgatg aatattacta atagtggtca tgagaataaa acaaaaggtg attctattca   1920
gaatgagaaa atcctaacc caatagaatc actcgaaaaa gaatctgctt tcaaaacgaa   1980
agctgaacct ataagcagca gtataagcaa tatggaactc gaattaaata tccacaattc   2040
aaaagcacct aaaagaata ggctgaggag gaagtcttct accaggcata ttcatgcgct   2100
tgaactagta gtcagtagaa atctaagccc acctaattgt actgaattgc aaattgatag   2160
ttgttctagc agtgaagaga taagaaaaa aaagtacaac caaatgccag tcaggcacag   2220
cagaacccta caactcatgg aaggtaaaga acctgcaact ggagccaaga gagtaacaa   2280 gccaaatgaa cagacaagta aaagacatga cagcgatact ttcccagagc tgaagttaac   2340
aaatgcacct ggttcttta ctaagtgttc aaataccagt gaacttaaag aatttgtcaa   2400
tcctagcctt ccaagagaag aaaaagaaga gaaactagaa acagttaaag tgtctaataa   2460
tgctgaagac cccaaagatc tcatgttaag tggagaaagg gtttttgcaaa ctgaaagatc   2520 tgtagagagt agcagtattt cattggtacc tggtactgat tatggcactc aggaaagtat   2580
ctcgttactg gaagttagca ctctagggaa ggcaaaaaca gaaccaaata aatgtgtgag   2640
tcagtgtgca gcatttgaaa accccaaggg actaattcat ggttgttcca agataatag   2700 aaatgacaca gaaggctta agtatccatt gggacatgga gttaaccaca gtcgggaaac   2760
aagcatagaa atggaagaaa gtgaacttga tgctcagtat ttgcagaata cattcaaggt   2820
```

```
ttcaaagcgc cagtcatttg ctccgttttc aaatccagga aatgcagaag aggaatgtgc   2880
aacattctct gcccactctg ggtccttaaa gaaacaaagt ccaaaagtca cttttgaatg   2940
tgaacaaaag gaagaaaatc aaggaaagaa tgagtctaat atcaagcctg tacagacagt   3000
taatatcact gcaggctttc ctgtggttgg tcagaaagat aagccagttg ataatgccaa   3060
atgtagtatc aaaggaggct ctaggttttg tctatcatct cagttcagag gcaacgaaac   3120
tggactcatt actccaaata aacatggact tttacaaaac ccatatcgta taccaccact   3180
ttttcccatc aagtcatttg ttaaaactaa atgtaagaaa atctgctag aggaaaactt    3240 tgaggaacat tcaatgtcac ctgaaagaga atgggaaat gagaacattc caagtacagt    3300
gagcacaatt agccgtaata acattagaga aaatgttttt aaagaagcca gctcaagcaa   3360
tattaatgaa gtaggttcca gtactaatga agtgggctcc agtattaatg aaataggttc   3420
cagtgatgaa acattcaag cagaactagg tagaaacaga gggccaaaat tgaatgctat    3480
gcttagatta ggggttttgc aacctgaggt ctataaacaa agtcttcctg gaagtaattg   3540
taagcatcct gaaataaaaa agcaagaata tgaagaagta gttcagactg ttaatacaga   3600
tttctctcca tatctgattt cagataactt agaacagcct atgggaagta gtcatgcatc   3660
tcaggtttgt tctgagacac ctgatgacct gttagatgat ggtgaaataa aggaagatac   3720
tagttttgct gaaaatgaca ttaaggaaag ttctgctgtt tttagcaaaa gcgtccagaa   3780
aggagagctt agcaggagtc ctagccctt cacccataca catttggctc agggttaccg    3840
aagaggggcc aagaaattag agtcctcaga agagaactta tctagtgagg atgaagagct   3900
tccctgcttc caacacttgt tatttggtaa agtaaacaat ataccttctc agtctactag   3960
gcatagcacc gttgctaccg agtgtctgtc taagaacaca gaggagaatt tattatcatt   4020
gaagaatagc ttaaatgact gcagtaacca ggtaatattg gcaaaggcat ctcaggaaca   4080
tcaccttagt gaggaaacaa atgttctgc tagcttgttt tcttcacagt gcagtgaatt    4140
ggaagacttg actgcaaata caaacaccca ggatcctttc ttgattggtt cttccaaaca   4200
aatgaggcat cagtctgaaa gccagggagt tggtctgagt gacaaggaat tggtttcaga   4260
tgatgaagaa agaggaacgg gcttggaaga aaataatcaa gaagagcaaa gcatggattc   4320
aaacttaggt gaagcagcat ctgggtgtga gagtgaaaca agcgtctctg aagactgctc   4380
agggctatcc tctcagagtg acattttaac cactcagcag agggatacca tgcaacataa   4440
cctgataaag ctccagcagg aaatggctga actagaagct gtgttagaac agcatgggag   4500
ccagccttct aacagctacc cttccatcat aagtgactct tctgcccttg aggacctgcg   4560
aaatccagaa caaagcacat cagaaaaagc agtattaact tcacagaaaa gtagtgaata   4620
ccctataagc cagaatccag aaggcctttc tgctgacaag tttgaggtgt ctgcagatag   4680
ttctaccagt aaaaataaag aaccaggagt ggaaaggtca tccccttcta aatgcccatc   4740
attagatgat aggtggtaca tgcacagttg ctctgggagt cttcagaata gaaactaccc   4800
atctcaagag gagctcatta aggttgttga tgtggaggag caacagctgg aagagtctgg   4860
gccacacgat ttgacggaaa catcttactt gccaaggcaa gatctagagg gaacccctta   4920
cctggaatct ggaatcagcc tcttctctga tgacctgaa tctgatcctt ctgaagacag    4980
agccccagag tcagctcgtg ttggcaacat accatcttca acctctgcat tgaaagttcc   5040
ccaattgaaa gttgcagaat ctgcccagag tccagctgct gctcatacta ctgatactgc   5100
tgggtataat gcaatggaag aaagtgtgag cagggagaag ccagaattga cagcttcaac   5160
agaaagggtc aacaaaagaa tgtccatggt ggtgtctggc ctgaccccag aagaatttat   5220
```

```
gctcgtgtac aagtttgcca gaaaacacca catcacttta actaatctaa ttactgaaga    5280
gactactcat gttgttatga aaacagatgc tgagtttgtg tgtgaacgga cactgaaata    5340 tttttctagga attgcgggag gaaaatgggt agttagctat ttctgggtga cccagtctat    5400
taaagaaaga aaaatgctga atgagcatga ttttgaagtc agaggagatg tggtcaatgg    5460
aagaaaccac caaggtccaa agcgagcaag agaatcccag gacagaaaga tcttcagggg    5520
gctagaaatc tgttgctatg ggcccttcac caacatgccc acagatcaac tggaatggat    5580
ggtacagctg tgtggtgctt ctgtggtgaa ggagctttca tcattcaccc ttggcacagg    5640
tgtccaccca attgtggttg tgcagccaga tgcctggaca gaggacaatg gcttccatgc    5700
aattgggcag atgtgtgagg cacctgtggt gacccgagag tgggtgttgg acagtgtagc    5760
actctaccag tgccaggagc tggacaccta cctgataccc cagatccccc acagccacta    5820
ctgactgcag ccagccacag gtacagagcc acaggacccc aagaatgagc ttacaaagtg    5880
gcctttccag gccctgggag ctcctctcac tcttcagtcc ttctactgtc ctggctacta    5940 aatatttat gtacatcagc ctgaaaagga cttctggcta tgcaagggtc ccttaaagat    6000
tttctgcttg aagtctccct tggaaatctg ccatgagcac aaaattatgg taattttttca    6060 cctgagaaga ttttaaaacc atttaaacgc caccaattga gcaagatgct gattcattat    6120
ttatcagccc tattctttct attcaggctg ttgttggctt agggctggaa gcacagagtg    6180
gcttggcctc aagagaatag ctggtttccc taagtttact tctctaaaac cctgtgttca    6240
caaaggcaga gagtcagacc cttcaatgga aggagagtgc ttgggatcga ttatgtgact    6300
taaagtcaga atagtccttg ggcagttctc aaatgttgga gtggaacatt ggggaggaaa    6360
ttctgaggca ggtattagaa atgaaaagga aacttgaaac ctgggcatgg tggctcacgc    6420
ctgtaatccc agcactttgg gaggccaagg tgggcagatc actggaggtc aggagttcga    6480
aaccagcctg gccaacatgg tgaaacccca tctctactaa aaatacagaa attagccggt    6540
catggtggtg gacacctgta atcccagcta ctcaggtggc taaggcagga gaatcacttc    6600
agcccgggag gtggaggttg cagtgagcca agatcatacc acggcactcc agcctgggtg    6660
acagtgagac tgtggctcaa aaaaaaaaa aaaaaaagga aatgaaact agaagagatt    6720 tctaaaagtc tgagatatat ttgctagatt tctaaagaat gtgttctaaa acagcagaag    6780 atttcaaga accggtttcc aaagacagtc ttctaattcc tcattagtaa taagtaaaat    6840
gtttattgtt gtagctctgg tatataatcc attcctctta aaatataaga cctctggcat    6900
gaatatttca tatctataaa atgacagatc ccaccaggaa ggaagctgtt gctttctttg    6960 aggtgattt tttccttgc tccctgttgc tgaaaccata cagcttcata aataatttg    7020 cttgctgaag gaagaaaaag tgttttcat aaacccatta tccaggactg tttatagctg    7080
ttggaaggac taggtcttcc ctagccccc cagtgtgcaa gggcagtgaa gacttgattg    7140
tacaaaatac gttttgtaaa tgttgtgctg ttaacactgc aaataaactt ggtagcaaac    7200
acttccaaaa aaaaaaaaaa aaaa                                          7224
```

<210> SEQ ID NO 6
<211> LENGTH: 1863
<212> TYPE: PRT
<213> ORGANISM: Homo sapiens

<400> SEQUENCE: 6

```
Met Asp Leu Ser Ala Leu Arg Val Glu Glu Val Gln Asn Val Ile Asn
1               5                   10                  15
```

-continued

```
Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
            115                 120                 125

Gly Tyr Arg Asn Arg Ala Lys Arg Leu Leu Gln Ser Glu Pro Glu Asn
130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
            195                 200                 205

Pro Gln Gly Thr Arg Asp Glu Ile Ser Leu Asp Ser Ala Lys Lys Ala
            210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
            275                 280                 285

Ser Leu Leu Leu Thr Lys Asp Arg Met Asn Val Glu Lys Ala Glu Phe
290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
            355                 360                 365

Asp Val Pro Trp Ile Thr Leu Asn Ser Ser Ile Gln Lys Val Asn Glu
            370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
            420                 425                 430
```

```
Ala Ser Asp Pro His Glu Ala Leu Ile Cys Lys Ser Glu Arg Val His
            435                 440                 445
Ser Lys Ser Val Glu Ser Asn Ile Glu Asp Lys Ile Phe Gly Lys Thr
450                 455                 460
Tyr Arg Lys Lys Ala Ser Leu Pro Asn Leu Ser His Val Thr Glu Asn
465                 470                 475                 480
Leu Ile Ile Gly Ala Phe Val Thr Glu Pro Gln Ile Ile Gln Glu Arg
                    485                 490                 495
Pro Leu Thr Asn Lys Leu Lys Arg Lys Arg Arg Pro Thr Ser Gly Leu
            500                 505                 510
His Pro Glu Asp Phe Ile Lys Lys Ala Asp Leu Ala Val Gln Lys Thr
            515                 520                 525
Pro Glu Met Ile Asn Gln Gly Thr Asn Gln Thr Glu Gln Asn Gly Gln
530                 535                 540
Val Met Asn Ile Thr Asn Ser Gly His Glu Asn Lys Thr Lys Gly Asp
545                 550                 555                 560
Ser Ile Gln Asn Glu Lys Asn Pro Asn Pro Ile Glu Ser Leu Glu Lys
                    565                 570                 575
Glu Ser Ala Phe Lys Thr Lys Ala Glu Pro Ile Ser Ser Ser Ile Ser
                580                 585                 590
Asn Met Glu Leu Glu Leu Asn Ile His Asn Ser Lys Ala Pro Lys Lys
            595                 600                 605
Asn Arg Leu Arg Arg Lys Ser Ser Thr Arg His Ile His Ala Leu Glu
            610                 615                 620
Leu Val Val Ser Arg Asn Leu Ser Pro Pro Asn Cys Thr Glu Leu Gln
625                 630                 635                 640
Ile Asp Ser Cys Ser Ser Ser Glu Glu Ile Lys Lys Lys Lys Tyr Asn
                    645                 650                 655
Gln Met Pro Val Arg His Ser Arg Asn Leu Gln Leu Met Glu Gly Lys
                660                 665                 670
Glu Pro Ala Thr Gly Ala Lys Lys Ser Asn Lys Pro Asn Glu Gln Thr
            675                 680                 685
Ser Lys Arg His Asp Ser Asp Thr Phe Pro Glu Leu Lys Leu Thr Asn
690                 695                 700
Ala Pro Gly Ser Phe Thr Lys Cys Ser Asn Thr Ser Glu Leu Lys Glu
705                 710                 715                 720
Phe Val Asn Pro Ser Leu Pro Arg Glu Glu Lys Glu Glu Lys Leu Glu
                    725                 730                 735
Thr Val Lys Val Ser Asn Asn Ala Glu Asp Pro Lys Asp Leu Met Leu
                740                 745                 750
Ser Gly Glu Arg Val Leu Gln Thr Glu Arg Ser Val Glu Ser Ser Ser
            755                 760                 765
Ile Ser Leu Val Pro Gly Thr Asp Tyr Gly Thr Gln Glu Ser Ile Ser
770                 775                 780
Leu Leu Glu Val Ser Thr Leu Gly Lys Ala Lys Thr Glu Pro Asn Lys
785                 790                 795                 800
Cys Val Ser Gln Cys Ala Ala Phe Glu Asn Pro Lys Gly Leu Ile His
                    805                 810                 815
Gly Cys Ser Lys Asp Asn Arg Asn Asp Thr Glu Gly Phe Lys Tyr Pro
                820                 825                 830
Leu Gly His Glu Val Asn His Ser Arg Glu Thr Ser Ile Glu Met Glu
            835                 840                 845
Glu Ser Glu Leu Asp Ala Gln Tyr Leu Gln Asn Thr Phe Lys Val Ser
```

-continued

```
                850            855            860

Lys Arg Gln Ser Phe Ala Pro Phe Ser Asn Pro Gly Asn Ala Glu Glu
865            870            875            880

Glu Cys Ala Thr Phe Ser Ala His Ser Gly Ser Leu Lys Lys Gln Ser
                885            890            895

Pro Lys Val Thr Phe Glu Cys Glu Gln Lys Glu Asn Gln Gly Lys
                900            905            910

Asn Glu Ser Asn Ile Lys Pro Val Gln Thr Val Asn Ile Thr Ala Gly
            915            920            925

Phe Pro Val Val Gly Gln Lys Asp Lys Pro Val Asp Asn Ala Lys Cys
            930            935            940

Ser Ile Lys Gly Gly Ser Arg Phe Cys Leu Ser Ser Gln Phe Arg Gly
945            950            955            960

Asn Glu Thr Gly Leu Ile Thr Pro Asn Lys His Gly Leu Leu Gln Asn
                965            970            975

Pro Tyr Arg Ile Pro Pro Leu Phe Pro Ile Lys Ser Phe Val Lys Thr
            980            985            990

Lys Cys Lys Lys Asn Leu Leu Glu Glu Asn Phe Glu Glu His Ser Met
        995            1000           1005

Ser Pro Glu Arg Glu Met Gly Asn Glu Asn Ile Pro Ser Thr Val
    1010           1015           1020

Ser Thr Ile Ser Arg Asn Asn Ile Arg Glu Asn Val Phe Lys Glu
    1025           1030           1035

Ala Ser Ser Ser Asn Ile Asn Glu Val Gly Ser Ser Thr Asn Glu
    1040           1045           1050

Val Gly Ser Ser Ile Asn Glu Ile Gly Ser Ser Asp Glu Asn Ile
    1055           1060           1065

Gln Ala Glu Leu Gly Arg Asn Arg Gly Pro Lys Leu Asn Ala Met
    1070           1075           1080

Leu Arg Leu Gly Val Leu Gln Pro Glu Val Tyr Lys Gln Ser Leu
    1085           1090           1095

Pro Gly Ser Asn Cys Lys His Pro Glu Ile Lys Lys Gln Glu Tyr
    1100           1105           1110

Glu Glu Val Val Gln Thr Val Asn Thr Asp Phe Ser Pro Tyr Leu
    1115           1120           1125

Ile Ser Asp Asn Leu Glu Gln Pro Met Gly Ser Ser His Ala Ser
    1130           1135           1140

Gln Val Cys Ser Glu Thr Pro Asp Asp Leu Leu Asp Asp Gly Glu
    1145           1150           1155

Ile Lys Glu Asp Thr Ser Phe Ala Glu Asn Asp Ile Lys Glu Ser
    1160           1165           1170

Ser Ala Val Phe Ser Lys Ser Val Gln Lys Gly Glu Leu Ser Arg
    1175           1180           1185

Ser Pro Ser Pro Phe Thr His Thr His Leu Ala Gln Gly Tyr Arg
    1190           1195           1200

Arg Gly Ala Lys Lys Leu Glu Ser Ser Glu Glu Asn Leu Ser Ser
    1205           1210           1215

Glu Asp Glu Glu Leu Pro Cys Phe Gln His Leu Leu Phe Gly Lys
    1220           1225           1230

Val Asn Asn Ile Pro Ser Gln Ser Thr Arg His Ser Thr Val Ala
    1235           1240           1245

Thr Glu Cys Leu Ser Lys Asn Thr Glu Glu Asn Leu Leu Ser Leu
    1250           1255           1260
```

-continued

```
Lys Asn Ser Leu Asn Asp Cys Ser Asn Gln Val Ile Leu Ala Lys
    1265                1270                1275

Ala Ser Gln Glu His His Leu Ser Glu Thr Lys Cys Ser Ala
    1280                1285                1290

Ser Leu Phe Ser Ser Gln Cys Ser Glu Leu Glu Asp Leu Thr Ala
    1295                1300                1305

Asn Thr Asn Thr Gln Asp Pro Phe Leu Ile Gly Ser Ser Lys Gln
    1310                1315                1320

Met Arg His Gln Ser Glu Ser Gln Gly Val Gly Leu Ser Asp Lys
    1325                1330                1335

Glu Leu Val Ser Asp Asp Glu Arg Gly Thr Gly Leu Glu Glu
    1340                1345                1350

Asn Asn Gln Glu Glu Gln Ser Met Asp Ser Asn Leu Gly Glu Ala
    1355                1360                1365

Ala Ser Gly Cys Glu Ser Glu Thr Ser Val Ser Glu Asp Cys Ser
    1370                1375                1380

Gly Leu Ser Ser Gln Ser Asp Ile Leu Thr Thr Gln Gln Arg Asp
    1385                1390                1395

Thr Met Gln His Asn Leu Ile Lys Leu Gln Gln Glu Met Ala Glu
    1400                1405                1410

Leu Glu Ala Val Leu Glu Gln His Gly Ser Gln Pro Ser Asn Ser
    1415                1420                1425

Tyr Pro Ser Ile Ile Ser Asp Ser Ser Ala Leu Glu Asp Leu Arg
    1430                1435                1440

Asn Pro Glu Gln Ser Thr Ser Glu Lys Ala Val Leu Thr Ser Gln
    1445                1450                1455

Lys Ser Ser Glu Tyr Pro Ile Ser Gln Asn Pro Glu Gly Leu Ser
    1460                1465                1470

Ala Asp Lys Phe Glu Val Ser Ala Asp Ser Ser Thr Ser Lys Asn
    1475                1480                1485

Lys Glu Pro Gly Val Glu Arg Ser Ser Pro Ser Lys Cys Pro Ser
    1490                1495                1500

Leu Asp Asp Arg Trp Tyr Met His Ser Cys Ser Gly Ser Leu Gln
    1505                1510                1515

Asn Arg Asn Tyr Pro Ser Gln Glu Glu Leu Ile Lys Val Val Asp
    1520                1525                1530

Val Glu Glu Gln Gln Leu Glu Glu Ser Gly Pro His Asp Leu Thr
    1535                1540                1545

Glu Thr Ser Tyr Leu Pro Arg Gln Asp Leu Glu Gly Thr Pro Tyr
    1550                1555                1560

Leu Glu Ser Gly Ile Ser Leu Phe Ser Asp Asp Pro Glu Ser Asp
    1565                1570                1575

Pro Ser Glu Asp Arg Ala Pro Glu Ser Ala Arg Val Gly Asn Ile
    1580                1585                1590

Pro Ser Ser Thr Ser Ala Leu Lys Val Pro Gln Leu Lys Val Ala
    1595                1600                1605

Glu Ser Ala Gln Ser Pro Ala Ala Ala His Thr Thr Asp Thr Ala
    1610                1615                1620

Gly Tyr Asn Ala Met Glu Glu Ser Val Ser Arg Glu Lys Pro Glu
    1625                1630                1635

Leu Thr Ala Ser Thr Glu Arg Val Asn Lys Arg Met Ser Met Val
    1640                1645                1650
```

|     |     |     |     |     |     |     |     |     |     |     |     |
| --- | --- | --- | --- | --- | --- | --- | --- | --- | --- | --- | --- |
| Val | Ser 1655 | Gly | Leu | Thr | Pro | Glu 1660 | Glu | Phe | Met | Leu | Val 1665 | Tyr | Lys | Phe |
| Ala | Arg 1670 | Lys | His | His | Ile | Thr 1675 | Leu | Thr | Asn | Leu | Ile 1680 | Thr | Glu | Glu |
| Thr | Thr 1685 | His | Val | Val | Met | Lys 1690 | Thr | Asp | Ala | Glu | Phe 1695 | Val | Cys | Glu |
| Arg | Thr 1700 | Leu | Lys | Tyr | Phe | Leu 1705 | Gly | Ile | Ala | Gly | Gly 1710 | Lys | Trp | Val |
| Val | Ser 1715 | Tyr | Phe | Trp | Val | Thr 1720 | Gln | Ser | Ile | Lys | Glu 1725 | Arg | Lys | Met |
| Leu | Asn 1730 | Glu | His | Asp | Phe | Glu 1735 | Val | Arg | Gly | Asp | Val 1740 | Val | Asn | Gly |
| Arg | Asn 1745 | His | Gln | Gly | Pro | Lys 1750 | Arg | Ala | Arg | Glu | Ser 1755 | Gln | Asp | Arg |
| Lys | Ile 1760 | Phe | Arg | Gly | Leu | Glu 1765 | Ile | Cys | Cys | Tyr | Gly 1770 | Pro | Phe | Thr |
| Asn | Met 1775 | Pro | Thr | Asp | Gln | Leu 1780 | Glu | Trp | Met | Val | Gln 1785 | Leu | Cys | Gly |
| Ala | Ser 1790 | Val | Val | Lys | Glu | Leu 1795 | Ser | Ser | Phe | Thr | Leu 1800 | Gly | Thr | Gly |
| Val | His 1805 | Pro | Ile | Val | Val | Val 1810 | Gln | Pro | Asp | Ala | Trp 1815 | Thr | Glu | Asp |
| Asn | Gly 1820 | Phe | His | Ala | Ile | Gly 1825 | Gln | Met | Cys | Glu | Ala 1830 | Pro | Val | Val |
| Thr | Arg 1835 | Glu | Trp | Val | Leu | Asp 1840 | Ser | Val | Ala | Leu | Tyr 1845 | Gln | Cys | Gln |
| Glu | Leu 1850 | Asp | Thr | Tyr | Leu | Ile 1855 | Pro | Gln | Ile | Pro | His 1860 | Ser | His | Tyr |